US007972611B2

(12) United States Patent
Kita et al.

(10) Patent No.: US 7,972,611 B2
(45) Date of Patent: Jul. 5, 2011

(54) FUNGUS-INDUCED INFLAMMATION AND EOSINOPHIL DEGRANULATION

(75) Inventors: Hirohito Kita, Rochester, MN (US); Jens Ponikau, Amherst, NY (US); Christopher Lawrence, Blackburg, VA (US)

(73) Assignees: Mayo Foundation for Medical Education and Research, Rochester, MN (US); Virginia Tech Intellectual Properties, Inc., Blacksburg, VA (US)

( * ) Notice: Subject to any disclaimer, the term of this patent is extended or adjusted under 35 U.S.C. 154(b) by 0 days.

(21) Appl. No.: 12/973,100

(22) Filed: Dec. 20, 2010

(65) Prior Publication Data

US 2011/0092675 A1  Apr. 21, 2011

Related U.S. Application Data

(62) Division of application No. 12/835,592, filed on Jul. 13, 2010, now Pat. No. 7,887,820, which is a division of application No. 12/629,638, filed on Dec. 2, 2009, now Pat. No. 7,815,919, which is a division of application No. 11/580,454, filed on Oct. 13, 2006, now Pat. No. 7,662,400.

(60) Provisional application No. 60/726,553, filed on Oct. 14, 2005.

(51) Int. Cl.
*A61K 39/00* (2006.01)
(52) U.S. Cl. ............... 424/274.1; 424/185.1; 424/94.1; 435/183; 530/350
(58) Field of Classification Search ................. None
See application file for complete search history.

(56) References Cited

U.S. PATENT DOCUMENTS 5,538,897 A  7/1996  Yates, III et al.
6,017,693 A  1/2000  Yates, III et al.

OTHER PUBLICATIONS

Aalberse and Platts-Mills, "How do we avoid developing allergy: Modifications of the T$_H$2 response from a B-cell perspective," *J. Allergy Clin. Immunol.*, 2004, 113:983-986.
Akdis et al., "Skin Homing (Cutaneous Lymphocyte-Associated Antigen-Positive) CD8+T Cells Respond to Superantigen and Contribute to Eosinophilia and IgE Production in Atopic Dermatitis," *J. Immunol.*, 1999, 163:466-475.
Al-Ani et al., "Modified Proteinase-Activated Receptor-1 and -2 Derived Peptides Inhibit Proteinase-Activated Receptor-2 Activation by Trypsin," *J. Pharmacol. Exp. Ther.*, 2002, 300(2):702-708.
Alexander et al., "*Leishmania mexicana* Cysteine Proteinase-Deficient Mutants Have Attenuated Virulence for Mice and Potentiate a Th1 Response," *J. Immunol.*, 1998, 161:6794-6801.
Almeida et al., "The Capsular Polysaccharides of *Cryptococcus neoformans* Activate Normal CD4+ $^{T\ Cells\ in\ a\ Dominant\ Th2\ Pattern}$," *J. Immunol.*, 2001, 167:5845-5851.
Bachert et al., "Total and specific IgE in nasal polyps is related to local eosinophilic inflammation," *J. Allergy Clin. Immunol.*, 2001, 107:607-614.
Beaumont et al., "Volumetric Aerobiological Survey of Conidial Fungi in the North-East Netherlands. II. Comparison of Aerobiological Data and Skin Tests with Mould Extracts in an Asthmatic Population," *Allergy*, 1985, 40:181-186.
Benninger et al., "Adult chronic rhinosinusitis: Definitions, diagnosis, epidemiology, and pathophysiology," *Otolaryngol. Head Neck Surg.*, 2003, 129:S1-S32.
Benninger et al., "Diagnosis and treatment of uncomplicated acute bacterial rhinosinusitis: Summary of the Agency for Health Care Policy and Research evidence-based report," *Otolaryngol. Head Neck. Surg.*, 2000, 122:1-7.
Bousquet et al., "Allergic rhinitis: A disease remodeling the upper airways?" *J. Allergy Clin. Immunol.*, 2004, 113:43-49.
Braunstahl et al., "Segmental Bronchial Provocation Induces Nasal Inflammation in Allergic Rhinitis Patients," *Am. J. Respir. Crit. Care Med.*, 2000, 161:2051-2057.
Brescianai et al., "Rhinosinusitis in severe asthma," *J. Allergy Clin. Immunol.*, 2001, 107:73-80.
Bush and Prochnau, "*Alternaria*-induced asthma," *J. Allergy Clin. Immunol.*, 2004, 113:227-234.
Buzina et al., "Fungal biodiversity—as found in nasal mucus," *Medical Mycology*, 2003, 41:149-161.
Catten et al., "Detection of Fungi in the Nasal Mucosa Using Polymerase Chain Reaction," *Laryngoscope*, 2001, 111:399-403.
Cho et al., "A High Throughput Targeted Gene Disruption Method for *Alternaria brassicicola* Functional Genomics Using Linear Minimal Element (LME) Constructs," *Molecular Plant-Microbe Interact.*, 2006, 19:7-15.
Cody et al., "Allergic Fungal Sinusitis: The Mayo Clinic Experience," *Laryngoscope*, 1994, 104:1074-1079.
Compton, "Glycosylation and Proteinase-Activated Receptor Function," *Drug Dev Res.*, 2003, 59:350-354.
Conte, Jr. et al., "Intrapulmonary Pharmacokinetics and Pharmacodynamics of Itraconazole and 14-Hydroxyitraconazole at Steady State," *Antimicrobial Agents and Chemotherapy*, 2004, 48(10):3823-3827.
Corey et al., "Allergic fungal sinusitis: Allergic, infectious, or both?" *Otolaryngol. Head Neck Surg.*, 1995, 113:110-119.
Corren et al., "Changes in bronchial responsiveness following nasal provocation with allergen," *J. Allergy Clin. Immunol.*, 1992, 89:611-618.
Cramer and Lawrence, "Identification of *Alternaria brassicicola* genes expressed in planta during pathogenesis of *Arabidopsis thaliana*," *Fungal Genet. Biol.*, 2004, 41:115-128.
Cramer et al., "Bioinformatic analysis of expressed sequence tags derived from a compatible *Alternaria brassicicola-Brassica oleracea* interaction," *Mol. Plant Pathol.*, 2006, 7(2):113-124.

(Continued)

*Primary Examiner* — Jennifer E Graser
(74) *Attorney, Agent, or Firm* — Fish & Richardson P.C.

(57) ABSTRACT

This document relates to methods and materials involved in fungus-induced inflammation and eosinophil degranulation. For example, isolated nucleic acids encoding fungal polypeptides, fungal polypeptides, methods for assessing fungus-induced inflammation, methods for assessing eosinophil degranulation, and methods for identifying inhibitors of fungus-induced inflammation and/or eosinophil degranulation are provided.

1 Claim, 50 Drawing Sheets

OTHER PUBLICATIONS

Dash et al., "Structural and Mechanistic Insight into the Inhibition of Aspartic Proteases by a Slow-Tight Binding Inhibitor from an Extremophilic *Bacillus* sp.: Correlation of the Kinetic Parameters with the Inhibitor Induced Conformational Changes," *Biochemistry*, 2001, 40:11525-11532.

Davis and Kita, "Pathogenesis of chronic rhinosinusitis: role of airborne fungi and bacteria," *Immunol. Allergy Clin. N. Am.*, 2004, 24:59-73.

Denning et al., "The link between fungi and severe asthma: a summary of the evidence," *Eur. Respir. J.*, 2006, 27:615-626.

deShazo and Swain, "Diagnostic criteria for allergic fungal sinusitis," *J. Allergy Clin. Immunol.*, 1995, 96:24-35.

Eichel, "A Proposal for a Staging System for Hyperplastic Rhinosinusitis Based on the Presence or Absence of Intranasal Polyposis," *Ear Nose Throat J.*, 1999, 78:262-265.

Eisenbarth et al., "Lipopolysaccharide-enhanced, Toll-like Receptor 4-dependent T Helper Cell Type 2 Responses to Inhaled Antigen," *J. Exp. Med.*, 2002, 196(12):1645-1651.

Fadel et al., "Alternaria spore and mycelium sensitivity in allergic patients: in vivo and in vitro studies," *Ann. Allergy*, 1992, 69:329-335.

Faveeuw et al., "Schistosome N-glycans containing core α3-fucose and core β2-xylose epitopes are strong inducers of Th2 responses in mice," *Eur. J. Immunol.*, 2003, 33:1271-1281.

Flotow et al., "Development of a Plasmepsin II Fluorescence Polarization Assay Suitable for High Throughput Antimalarial Drug Discovery," *J. Biomol. Screen.*, 2002, 7(4):367-371.

Fokkens et al., "EAACI Position Paper on Rhinosinusitis and Nasal Polyps Executive Summary," Allergy, 2005, 60:583-601.

Galagan et al., "Sequencing of *Aspergillus nidulans* and comparative analysis with *A. fumigatus* and *A. oryzae*," *Nature*, 2005, 438:1105-1115.

Gliklich and Metson, "The health impact of chronic sinusitis in patients seeking otolaryngologic care," *Otolaryngol. Head Neck Surg.*, 1995, 113:104-109.

Godthelp et al., "Dynamics of nasal eosinophils in response to a nonnatural allergen challenge in patients with allergic rhinitis and control subjects: A biopsy and brush study," *J. Allergy Clin. Immunol.*, 1996, 97:800-811.

Gonzalo et al., "Eosinophil Recruitment to the Lung in a Murine Model of Allergic Inflammation. The Role of T Cells, Chemokines, and Adhesion Receptors," *J Clin Invest.*, 1996, 98(10):2332-2345.

Gottlieb, "Relation of intranasal disease in the production of bronchial asthma," *JAMA*, 1925, 85(2):105-108.

Green et al., "Allergen detection from 11 fungal species before and after germination," *J. Allergy Clin. Immunol.*, 2003, 111:285-289.

Hamilos et al., "Evidence for distinct cytokine expression in allergic versus nonallergic chronic sinusitis," *J. Allergy Clin. Immunol.*, 1995, 96:537-544.

Hamilos, "Chronic sinusitis," *J. Allergy Clin. Immunol.*, 2000, 106:213-227.

Hansen et al., "Allergen-specific Th1 cells fail to counterbalance Th2 cell-induced airway hyperreactivity but cause severe airway inflammation," *J. Clin. Invest.*, 1999, 103(20:175-183.

Harlin et al., "A clinical and pathologic study of chronic sinusitis: The role of the eosinophil," *J. Allergy Clin. Immunol.*, 1988, 81:867-875.

Heaton et al., "An immunoepidemiological approach to asthma: identification of in-vitro T-cell response patterns associated with different wheezing phenotypes in children," *Lancet*, 2005, 365:142-149.

Hoover et al., "Chronic sinusitis: Risk factors for extensive disease," *J. Allergy Clin. Immunol.*, 1997, 100:185-191.

Horst et al., "Double-blind, placebo-controlled rush immunotherapy with a standardized *Alternaria* extract," *J. Allergy Clin. Immunol.*, 1990, 85:460-472.

Hunt et al., "Treatment of asthma with nebulized lidocaine: A randomized, placebo-controlled study," *J. Allergy Clin. Immunol.*, 2004, 113:853-859.

Hyrup and Nielsen, "Peptide Nucleic Acids (PNA): Synthesis, Properties and Potential Applications," *Bioorgan. Med. Chem.*, 1996, 4:5-23.

Inoue et al., "Nonpathogenic, Environmental Fungi Induce Activation and Degranulation of Human Eosinophils," *J. Immunol.*, 2005, 175:5439-5447.

Jarjour et al., "The Immediate and Late Allergic Response to Segmental Bronchopulmonary Provocation in Asthma," *Am. J. Respir. Crit. Care Med.*, 1997, 155:1515-1521.

Katzenstein et al., "Allergic *Aspergillus* sinusitis: a newly recognized form of sinusitis," *J. Allergy Clin. Immunol.*, 1983, 72:89-93.

Kauffman and van der Heide, "Exposure, Sensitization, and Mechanisms of Fungus-induced Asthma," *Curr. Allergy Asthma Rep.*, 2003, 3:430-437.

Kheradmand et al., "A Protease-Activated Pathway Underlying Th Cell Type 2 Activation and Allergic Lung Disease," *J. Immunol.*, 2002, 169:5904-5911.

Kita et al., "Biology of Eosinophils," *Allergy: Principles and Practice*, 2003, 6th Ed., Mosby-Year Book, Inc., Chapter 19, pp. 305-332.

Kita et al., "Mechanism of topical glucocorticoid treatment of hay fever: IL-5 and eosinophil activation during natural allergen exposure are suppressed, but IL-4, IL-6, and IgE antibody production are unaffected," *J. Allergy Clin. Immunol.*, 2000, 106:521-529.

Ling et al., "Relation of CD4+CD25+ regulatory T-cell suppression of allergen-driven T-cell activation to atopic status and expression of allergic disease," *Lancet*, 2004, 363:608-615.

Littell et al., "Changes in Airway Resistance following Nasal Provocation," *Am. Rev. Respir. Dis.*, 1990, 141:580-583.

Liu et al., "Decreased Expression of Membrane IL-5 Receptor α on Human Eosinophils: I. Loss of Membrane IL-5 Receptor α on Airway Eosinophils and Increased Soluble IL-5 Receptor α in the Airway After Allergen Challenge," *J. Immunol.*, 2002, 169:6452-6458.

Liu et al., "Decreased Expression of Membrane IL-5 Receptor α on Human Eosinophils: II. IL-5 Down-Modulates Its Receptor Via a Proteinase-Mediated Process," *J. Immunol.*, 2002, 169:6459-6466.

Lourbakos et al., "Cleavage and activation of proteinase-activated receptor-2 on human neutrophils by gingipain-R from *Porphyromonas gingivalis*," *FEBS Lett.*, 1998, 435:45-48.

Lund and Mackay, "Staging in rhinosinusitis," *Rhinology*, 1993, 31:183-184.

Lund et al., "Functional endoscopic sinus surgery in the management of chronic rhinosinusitis. An objective assessment," *J. Laryngol. Otol.*, 1991, 105:832-835.

Machida et al., "Genome sequencing and analysis of *Aspergillus oryzae*," *Nature*, 2005, 438:1157-1161.

Mannering et al., "A sensitive method for detecting proliferation of rare autoantigen-specific human T cells," *J. Immunol. Meth.*, 2003, 283:173-183.

Matsuwaki Y., et al., "Recognition of Fungal Protease Activities Induces Cellular Activation and Eosinophil-Derived Neurotoxin Release in Human Eosinophils," *J. Immunology*, 183:6708-6716 (2009).

McDonald and Kuritzkes, "Human Immunodeficiency Virus Type 1 Protease Inhibitors," *Arch. Intern. Med.*, 1997, 157:951-959.

Meltzer et al., "Rhinosinusitis: Establishing definitions for clinical research and patient care," *J. Allergy Clin. Immunol.*, 2004, 114(6):S155-S212.

Miike and Kita, "Human eosinophils are activated by cysteine proteases and release inflammatory mediators," *J. Allergy Clin. Immunol.*, 2003, 111:704-713.

Miike et al., "Trypsin Induces Activation and Inflammatory Mediator Release from Human Eosinophils Through Protease-Activated Receptor-2," *J. Immunol.*, 2001, 167:6615-6622.

Mikayama et al., *Proc. Natl. Acad. Sci. USA*, 90:10056-10060 (1993).

Millar et al., "Allergic aspergillosis of the maxillary sinuses," *Thorax*, 1981, 36:710, Abstract.

Miller et al., "Accumulation of interferon gamma-producing TH1 helper T cells in nasal polyps," *Otolaryngol. Head Neck Surg.*, 1994, 111:51-58.

Mills, "Regulatory T cells: friend or foe in immunity to infection?" *Nat. Rev. Immunol.*, 2004, 4:841-855.

Minetoki et al., *Biosci. Biotechnol. Biochem.*, 59:1516-1521 (1995).

Mitakakis et al., "Spore germination increases allergen release from *Alternaria*," *J. Allergy Clin. Immunol.*, 2001, 107:388-390.

Morpeth et al., "Fungal sinusitis: an update," *Ann. Allergy Asthma Immunol.*, 1996, 76:128-140.

Murphy and Reiner, "The lineage decisions of helper T cells," *Nat. Rev. Immunol.*, 2002, 2:933-944.

Mygind et al., "Nasal polyposis, eosinophil dominated inflammation, and allergy," *Thorax*, 2000, 55(Suppl 2):S79-S83.

Newman et al., "Chronic Sinusitis. Relationship of Computed Tomographic Findings to Allergy, Asthma, and Eosinophilia," *JAMA*, 1994, 271:363-367.

Nolte and Berger, "On vagal bronchoconstriction in asthmatic patients by nasal irritation," *Eur. J. Respir. Dis.*, 1983, 64(suppl. 128):110-114.

Platts-Mills and Rosenwasser, "Chronic sinusitis consensus and the way forward," *J. Allergy Clin. Immunol.*, 2004, 114:1359-1361.

Platts-Mills et al., "Sensitisation, asthma, and a modified Th2 response in children exposed to cat allergen: a population-based cross-sectional study," *Lancet*, 2001, 357:752-756.

Ponikau et al., "Antifungal nasal washes for chronic rhinosinusitis: What's therapeutic—the wash or the antifungal?" *J. Allergy Clin. Immunol.*, 2003, 111:1137-1138.

Ponikau et al., "Striking deposition of toxic eosinophil major basic protein in mucus: Implications for chronic rhinosinusitis," *J. Allergy Clin. Immunol.*, 2005, 116:362-369.

Ponikau et al., "Features of airway remodeling and eosinophilic inflammation in chronic rhinosinusitis: Is the histopathology similar to asthma?" *J. Allergy Clin. Immunol.*, 2003, 112:877-882.

Ponikau et al., "Intranasal antifungal treatment in 51 patients with chronic rhinosinusitis," *J. Allergy Clin. Immunol.*, 2002, 110:862-866.

Ponikau et al., "Striking deposition of toxic eosinophil major basic protein in mucus: Implications for chronic rhinosinusitis," *J. Allergy Clin. Immunol.*, 2005, 116:362-369.

Ponikau et al., "The Diagnosis and Incidence of Allergic Fungal Sinusitis," *Mayo Clin. Proc.*, 1999, 74:877-884.

Ponikau et al., "Treatment of chronic rhinosinusitis with intranasal amphotericin B: A randomized, placebo-controlled, double-blind pilot trial," *J. Allergy Clin. Immunol.*, 2005, 115:125-131.

Prussin and Metcalfe, "Detection of intracytoplasmic cytokine using flow cytometry and directly conjugated anti-cytokine antibodies," *J. Immunol. Meth.*, 1995, 188:117-128.

Pulendran et al., "Lipopolysaccharides from Distinct Pathogens Induce Different Classes of Immune Responses In Vivo," *J. Immunol.*, 2001, 167:5067-5076.

Rachelefsky et al., "Chronic Sinus Disease with Associated Reactive Airway Disease in Children," *Pediatrics*, 1984, 73(4):526-529.

Radhakrishnan et al., "Dendritic cells activated by cross-linking B7-DC (PD-L2) block inflammatory airway disease," *J. Allergy Clin. Immunol.*, 2005, 116:668-674.

Radharkrishnan et al., "Blockade of Allergic Airway Inflammation Following Systemic Treatment with a B7-Dendritic Cell (PD-L2) Cross-Linking Human Antibody," *J. Immunol.*, 2004, 173:1360-1365.

Rains and Mineck, "Treatment of Allergic Fungal Sinusitis with High-Dose Itraconazole," *Am. J. Rhinol.*, 2003, 17:1-8.

Rajagopalan et al., "Intranasal Exposure to Bacterial Superantigens Induces Airway Inflammation in HLA Class II Transgenic Mice," *Infect. Immun.*, 2006, 74(2):1284-1296.

Randolph et al., "Modulation of Airway Inflammation by Passive Transfer of Allergen-Specific Th1 and Th2 Cells in a Mouse Model of Asthma," *J. Immunol.*, 1999, 162:2375-2383.

Ray et al., "Healthcare expenditures for sinusitis in 1996: Contributions of asthma, rhinitis, and other airway disorders," *J. Allergy Clin. Immunol.*, 1999, 103:408-414.

Reed and Kita, "The role of protease activation of inflammation in allergic respiratory diseases," *J. Allergy Clin. Immunol.*, 2004, 114:997-1008.

Reichard et al., "Sedolisins, a New Class of Secreted Proteases from *Aspergillus fumigatus* with Endoprotease or Tripeptidyl-Peptidase Activity at Acidic pHs," *Appl. Environ. Microbiol.*, 2006, 72(3):1739-1748..

Romani, "Immunity to fungal infections," *Nat. Rev. Immunol.*, 2004, 4:1-23.

Rudinger et al., Peptide Hormones. Biol. Council, pp. 5-7 (1976).

Sánchez-Segura et al., "T lymphocytes that infiltrate nasal polyps have a specialized phenotype and produce a mixed $T_{H1}/T_{H2}$ pattern of cytokines," *J. Allergy Clin. Immunol.*, 1998, 102:953-960.

Sansonetti, "War and peace at mucosal surfaces," *Nat. Rev. Immunol.*, 2004, 4:953-964.

Sasama et al., "New paradigm for the roles of fungi and eosinophils in chronic rhinosinusitis," *Curr. Opin. Otolaryngol. Head Neck Surg.*, 2005, 13:2-8.

Schubert et al., "HLA-DQB1 *03 in allergic fungal sinusitis and other chronic hypertrophic rhinosinusitis disorders," *J. Allergy Clin. Immunol.*, 2004, 114:1376-1383.

Schubert, "A superantigen hypothesis for the pathogenesis of chronic hypertrophic rhinosinusitis, allergic fungal sinusitis, and related disorders," *Ann. Allergy Asthma Immunol.*, 2001, 87:181-188.

Schumacher et al., "Pulmonary response to nasal-challenge testing of atopic subjects with stable asthma," *J. Allergy Clin. Immunol.*, 1986, 78:30-35.

Sedgwick et al, "Immediate and Late Airway Response of Allergic Rhinitis Patients to Segmental Antigen Challenge. Characterization of Eosinophil and Mast Cell Mediators," *Am. Rev. Respir. Dis.*, 1991, 144:1274-1281.

Sedgwick et al., "Oxidized Low-Density Lipoprotein Activates Migration and Degranulation of Human Granulocytes," *Am. J. Respir. Cell Mol. Biol.*, 2003, 29:702-709.

Sedgwick et al., "Peripheral blood eosinophils from patients with allergic asthma contain increased intracellular eosinophil-derived neurotoxin," *J. Allergy Clin. Immunol.*, 2004, 114:568-574.

Seiberling et al., "Superantigens and Chronic Rhinosinusitis: Detection of Staphylococcal Exotoxins in Nasal Polyps," *Laryngoscope*, 2005, 115:1580-1585.

Settipane, "Epidemiology of Nasal Polyps," *Allergy Asthma Proc.*, 1996, 17:231-236.

Shin et al., "Chronic rhinosinusitis: An enhanced immune response to ubiquitous airborne fungi," *J. Allergy Clin. Immunol.*, 2004, 114:1369-1375.

Shin et al., "Degranulation of human eosinophils induced by *Paragonismus westermani*-secreted protease," *Korean J. Parasitol.*, 2005, 43:33-37.

Shin et al., "Excretory-Secretory Products Secreted by *Paragonimus westermani* Delay the Spontaneous Cell Death of Human Eosinophils through Autocrine Production of GM-CSF," *Int. Arch. Allergy Immunol.*, 2003, 132:48-57.

Shin et al., "The Effect of Nasal Polyp Epithelial Cells on Eosinophil Activation," *Laryngoscope*, 2003, 113:1374-1377.

Shinkai et al., "Helper T cells regulate type-2 innate immunity in vivo," *Nature*, 2002, 420:825-829.

Slavin, "Sinusitis in adults and its relation to allergic rhinitis, asthma, and nasal polyps," *J. Allergy. Clin. Immunol.*, 1988, 82:950-956.

Slavin, "The 10th annual Clemens von Pirquet lectureship. Clinical disorders of the nose and their relationship to allergy," *Ann. Allergy*, 1982, 49(3):123-126.

Steinhoff et al., "Proteinase-Activated Receptors: Transducers of Proteinase-Mediated Signaling in Inflammation and Immune Response," *Endocr. Rev.*, 2005, 26:1-43.

Stevens et al., "A Randomized Trial of Itraconazole in Allergic Bronchopulmonary Aspergillosis," *N. Engl. J. Med.*, 2000, 342:756-762.

Stoop et al., "Eosinophils in nasal polyps and nasal mucosa: An immunohistochemical study," *J. Allergy Clin. Immunol.*, 1993, 91:616-622.

Stringer and Ryan, "Chronic invasive fungal rhinosinusitis," *Otolaryngol. Clin. N. Am.*, 2000, 33(2):375-387.

Summerton and Weller, "Morpholino Antisense Oligomers: Design, Preparation, and Properties," *Antisense Nucleic Acid Drug Dev.*, 1997, 7:187-195.

Takahashi et al., "Immunologic Self-Tolerance Maintained by $CD25^+CD4^+$ Regulatory T Cells Constitutively Expressing Cytotoxic T Lymphocyte-associated Antigen 4," *J. Exp. Med.*, 2000, 192(2):303-309.

Taylor et al., "Detection of fungal organisms in eosinophilic mucin using a fluorescein-labeled chitin-specific binding protein," *J. Otolaryngol. Head Neck Surg,*, 2002, 127:377-383.

Ten Brinke et al., "Chronic sinusitis in severe asthma is related to sputum eosinophilia," *J. Allergy. Clin. Immunol.*, 2002, 109:621-626.

Till et al., "IL-5 secretion by allergen-stimulated CD4+ T cells in primary culture: Relationship to expression of allergic disease," *J. Allergy Clin. Immunol.*, 1997, 99:563-569.

Tripathi et al., "Staphylococcal Exotoxins and Nasal Polyposis: Analysis of Systemic and Local Responses," *Am. J. Rhinol.*, 2005, 19:327-333.

Umezawa et al., "Pepstatin, a new pepsin inhibitor produced by Actinomycetes," *J. Antibiot.*, 1970, 23(5):259-262.

Van Keulen et al , "Immunomodulation using the recombinant monoclonal human B7-DC cross-linking antibody rHIgM12," *Clin. Exp. Immunol.*, 2005, 143:314-321.

Van Loon and Weinshilboum, "Thiopurine methyltransferase isozymes in human renal tissue," *Drug Metab. Dispos.*, 1990, 18(5):632-638.

Van Loon et al., "Human kidney thiopurine methyltransferase. Photoaffinity labeling with S-adenosyl-L-methionine," *Biochem. Pharmacol.*, 1992, 44(4):775-785.

Van Zele et al., "*Staphylococcus aureus* colonization and IgE antibody formation to enterotoxins is increased in nasal polyposis," *J. Allergy Clin. Immunol.*, 2006, 114(4):981-983.

Vennewald et al., "Fungal colonization of the paranasal sinuses," *Mycoses*, 1999, 42(Suppl 2):33-36.

Vercelli, "Novel insights into class switch recombination," *Curr. Opin. Allergy Clin. Immunol.*, 2002, 2:147-151.

Walker et al., "IL-5 Production by NK Cells Contributes to Eosinophil Infiltration in a Mouse Model of Allergic Inflammation," *J. Immunol.*, 1998, 161:1962-1969.

Wei et al., "The Chemotactic Behavior of Eosinophils in Patients with Chronic Rhinosinusitis," *Laryngoscope*, 2003, 113:303-306.

Wong et al., "Human GM-CSF: Molecular Cloning of the Complementary DNA and Purification of the Natural and Recombinant Proteins," *Science*, 1985, 228:810-815.

Wu et al., "Inhibition of S-Adenosyl-L-Homocysteine Hydrolase Induces Immunosuppression," *J. Pharmacol. Exp. Therap.*, 2005, 313(2):705-711.

Yamazaki et al., "Allergen-Specific In Vitro Cytokine Production in Adult Patients with Eosinophilic Esophagitis," *Dig. Dis. Sci.*, 2006, 51:1934-1941.

Zhu et al., "Acidic Mammalian Chitinase in Asthmatic Th2 Inflammation and IL-13 Pathway Activation," *Science*, 2004, 304:1678-1682.

Zureik et al., "Sensitisation to airborne moulds and severity of asthma: cross sectional study from European Community respiratory health survey," *BMJ*, 2002, 325:411-414.

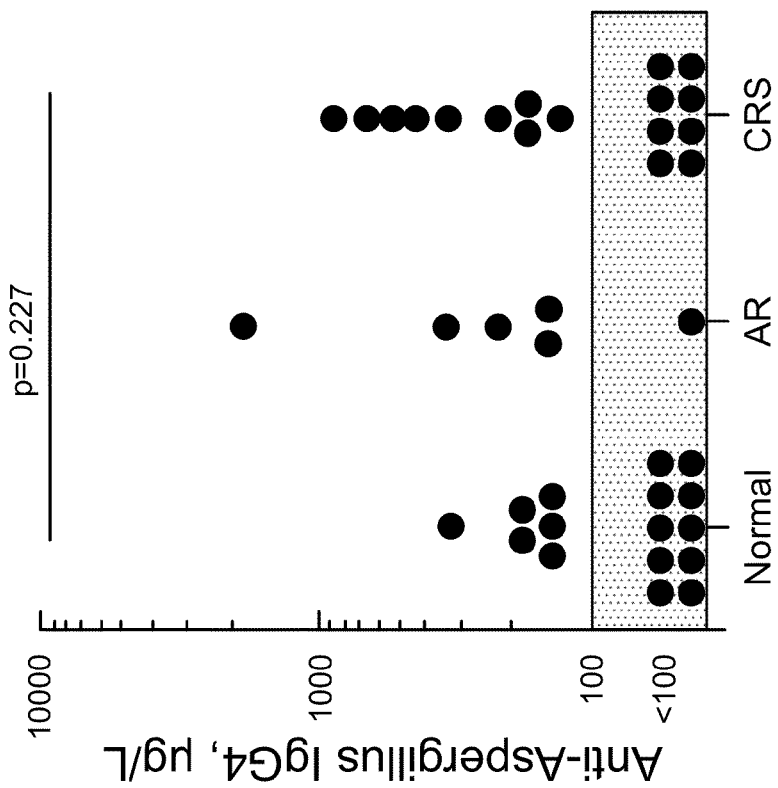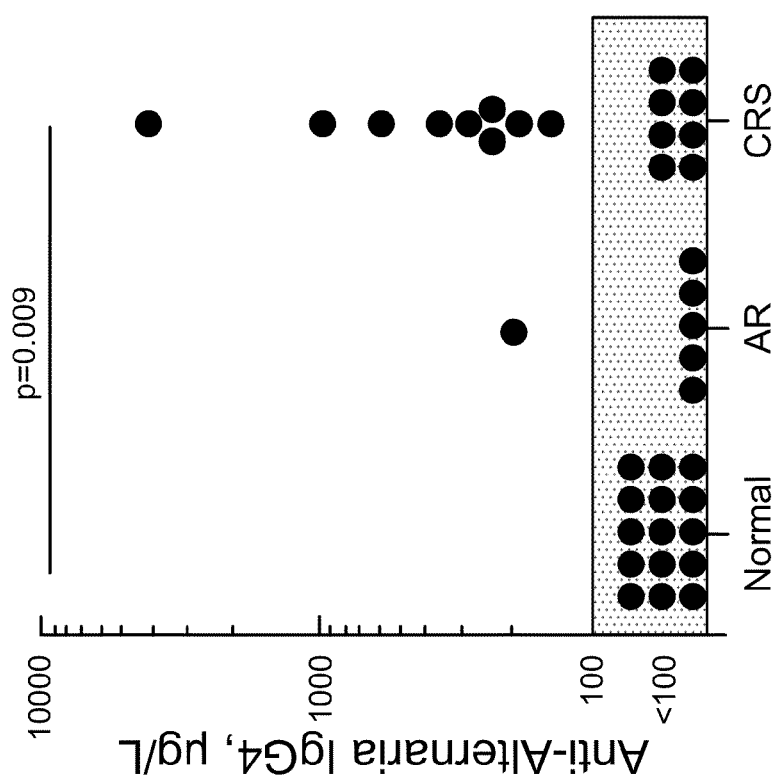
FIG. 3

FIGURE 27

ATGCATTTCCGCGGATCCTCCATCTACTTCGGCATCGTTGCCCTCTCCTCGACT
TCAGCTGTCCTTGGAGCCGTCGCTCCCTACGGACAATGCGGTGGTAACGGCTT
CCAGGGCGAGACCGAGTGCGCTCAAGGCTGGTCTTGCGTCAAGAGCAACGAC
TGGTACAGCCAGTGCATCAACGGTGGTGGAAACGCCCCGGCTCCTCCTGCTG
CTACTGGCGTCGCGCCGGCACCCGTCATTCCTTCTGCCGCCCTGTACCGTCG
ATGAACGCTAGCGAGCCCGTCGCCGCCCTGTTGCGGTTGCTCAGCCTGCTGC
CACCGGCGGTGCCAACGGCTCTGCTCCTGATGTTGCCGGAACCGGTGCCAAC
GGTGCCAAGTGCTCGCTCGATGCTGCATTCAAGTCGCACGGCAAGAAGTACA
TCGGTGTTGCTACCGACCAGGGCGCACTCAGCAAGGGAAAGAACAAGGAGA
TCATCGTCGCAAACTTCGGCCAGGTTACTCCTGAGAACAGCATGAAGTGGGA
TGCCACCGAGGGTACCGAGGGCAAGTTCACTCTCGACGGTGCCAACGCGCTC
GTCAGCTTTGCCACGGAGAACAAGAAGCTCGTCCGCGGTCACACCACCGTCT
GGCACTCTCAGCTTCCCACCTGGGTCTCTTCCATCACCGACAAGACTAAGCTC
GAGGAAGTCATGGTTGCTCACATCAAGAAGCTCATGAGCACCTACGCCGGCA
AGGTCTATGCTTGGGACGTAGTCAACGAGATCTTCAACGAAGACGGTTCTTTC
CGCTCTTCCGTCTTCTACAACGTTCTCGGTGAGAACTTTGTCGCTACCGCTTTC
GCTACTGCCAAGGCCGCCGACCCAGAGGCCAAGCTCTACATCAACGACTACA
ACCTCGACAGCCCCAGTTACGCTAAGACCAAGGCCATGGCTAGCAACGTCAA
GAAGTGGGTTGCCGCCGGTGTTCCCATTGACGGTATTGGTTCCCAGTCCCACT
TGTCCGGCAGCTGGCCCATCTCCGACTACCCCGCTGCTCTCAAGCTTCTCTGC
GAGTCTGCTTCCGAGTGCGCCATGACTGAGCTTGACATCAAGGGTGGTGCTG
CCGCTGACTACAAGACTGCTGTCACTGCTTGCTTGGATGTCGAGAACTGTGTT
GGTGTTACCGTCTGGGGTGTTAGCGACACTGACTCTTGGATCGGCGCTGCTGC
CACTCCTCTGCTTTTCGACGGCAGCTTCCAGGCCAAGGAGTCTTACAACGGTC
TCTGCTCCGCTCTTGCTTAAATGCACAGGGTGAGAACGAGGGCATCCGATTA
GATCTATCAGCTTAAGACAGACAATTTGGTGCTTGAAAAAGGTGTTTGTTTCT
TGTAGGAGATGGGATGAAATTCTACCGTATATATATCTACTTTGGTAAGATGG
TAAACTCCATCTTCCAATTGATCATTTTATTGAAAAAAAAAA (SEQ ID NO:1)

MHFRGSSIYFGIVALSSTSAVLGAVAPYGQCGGNGFQGETECAQGWSCVKSND
WYSQCINGGGNAPAPPAATGVAPAPVIPSAAPVPSMNASEPVAAPVAVAQPAAT
GGANGSAPDVAGTGANGAKCSLDAAFKSHGKKYIGVATDQGALSKGKNKEIIV
ANFGQVTPENSMKWDATEGTEGKFTLDGANALVSFATENKKLVRGHTTVWHS
QLPTWVSSITDKTKLEEVMVAHIKKLMSTYAGKVYAWDVVNEIFNEDGSFRSSV
FYNVLGENFVATAFATAKAADPEAKLYINDYNLDSPSYAKTKAMASNVKKWV
AAGVPIDGIGSQSHLSGSWPISDYPAALKLLCESASECAMTELDIKGGAAADYKT
AVTACLDVENCVGVTVWGVSDTDSWIGAAATPLLFDGSFQAKESYNGLCSALA
(SEQ ID NO:2)

FIGURE 28

ATGTCTGCCCCCGCCCACAAGTTCAAGGTTGCCGACATCAGTCTTGCGGCGTT
CGGTCGCCGCGAGATTGAGCTCGCCGAGAATGAGATGCCTGGTCTGATGGAG
ACTCGCCGCAAGTATGCTGAGGACCAGCCATTGAAGGGCGCCCGCATTGCTG
GATGTCTGCACATGACCATCCAGACTGCCGTTCTCATCGAGACGCTCAAGTCC
CTCGGTGCTGAGCTCACCTGGACATCCTGCAACATCTTCTCCACCCAGGACCA
CGCTGCCGCTGCCATTGCCGCTGCCGGCGTACCTGTCTTCGCCTGGAAGGGCG
AGACCGAGGAGGAGTACGAGTGGTGCCTTGAGCAGCAACTCACAGCTTTCAA
GGACGGCAAGAGCCTGAACTTGATCCTTGACGACGGTGGCGACCTCACTGCC
CTTGTCCACAAGAAGTACCCTGAGATGCTCAAGGACTGCTACGGTGTCTCGG
AAGAGACCACCACTGGTGTCCACCACCTCTACCGCATGTTGAAGGGCAAGGG
TCTCCTCGTCCCCGCCATCAACGTCAACGACTCCGTCACCAAGTCCAAGTTCG
ACAACTTGTACGGTTGCCGTGAGTCGCTCGTCGACGGCATCAAGCGTGCGAC
CGACGTCATGATTGCTGGCAAGGTCGCCGTCGTCGCTGGTTTCGGTGATGTCG
GCAAGGGTTGCGCCCAGGCTCTCCACAGCATGGGTGCCCGTGTCATCGTCAC
CGAGATTGACCCCATCAACGCCCTCCAGGCTGCCGTTTCCGGCTTCCAGGTTA
CCACCATGGAGAAGGCCGCTCCTCAGGGTCAGATCTTCGTCACCACCACTGG
TTGCCGTGACATCCTGACTGGCGTCCACTTCGAGGCTATGCCCAACGATGCCA
TCGTCTGCAACATCGGTCACTTCGACATCGAAATCGACGTTGCGTGGCTCAAG
AAGAACGCCAAGTCCGTCACCAGCATCAAGCCCCAGGTCGACCGCTACCTGA
TGAACAATGGCCGCTACATCATCCTCCTCGCTGAGGGCCGTCTCGTCAACTTG
GGATGCGCCACTGGCCACTCTTCCTTCGTCATGTCCTGCTCTTTCACCAACCA
GGTCCTTGCCCAGATTATGCTGTACAAGGCCTCTGACGAGGAGTTTGGCAAC
AAGTACGTCGAGTTCGGCAAGACCGGTAAGCTCGATGTCGGTGTCTACGTTC
TGCCCAAGATTCTCGACGAGCAAGTCGCTCTTCTCCACTTGGCACACGTCAAC
GTTGAGCTCTCCAAGCTCAGCGATGTCCAGGCCGAGTACCTTGGTCTCCCTGT
TGAGGGTCCTTTCAAGAGCGACATCTACCGTTACTAG (SEQ ID NO:3)

MSAPAHKFKVADISLAAFGRREIELAENEMPGLMETRRKYAEDQPLKGARIAGC
LHMTIQTAVLIETLKSLGAELTWTSCNIFSTQDHAAAAIAAAGVPVFAWKGETEE
EYEWCLEQQLTAFKDGKSLNLILDDGGDLTALVHKKYPEMLKDCYGVSEETTT
GVHHLYRMLKGKGLLVPAINVNDSVTKSKFDNLYGCRESLVDGIKRATDVMIA
GKVAVVAGFGDVGKGCAQALHSMGARVIVTEIDPINALQAAVSGFQVTTMEKA
APQGQIFVTTTGCRDILTGVHFEAMPNDAIVCNIGHFDIEIDVAWLKKNAKSVTSI
KPQVDRYLMNNGRYIILLAEGRLVNLGCATGHSSFVMSCSFTNQVLAQIMLYKA
SDEEFGNKYVEFGKTGKLDVGVYVLPKILDEQVALLHLAHVNVELSKLSDVQAE
YLGLPVEGPFKSDIYRY (SEQ ID NO:4)

FIGURE 29

ATGAAGTCTGTAGCTGTCCTCCCCGCCATCTTGGCCCTGGCCCACGCCCACGC
CACTTTCCAACAACTCTGGAAGAACGGAAAGGATCTGGAGAGCACCTGTGCC
AGGTTGCCACCGTCCAACAGCCCTGTTGAGGACTACACCAGCAACGCTCTGC
AATGCAACGTCAGCCCTGCTCCTGCCGAGGGAAAGTGCGCTTTCGAGGCCGG
TGACACGGTAACCATCGAGATGCACCAGCACAACACCCGTGACTGCAAGGA
GGAAGGTATTGGTGGTGCCCACTGGGGCCCTGTCCTCGCATACATGTCCAAG
GTTGAGGACGCAGCCACCGCAGATGGCTCCAGCGAGTTCTTCAAGGTTTACC
AGAACACCTGGGCTAAGAACCCAGACGCCACTCAGGGCGACAACGACTTTTG
GGGTACCAAGGACCTCAACTACAACTGCGGAAAGCTCGACTTTGCCATTCCC
AAGAACATTGCTCCTGGTGACTACCTCCTCCGTGCCGAGGCCATCGCCCTCCA
CGCTGCAAGCGCAGGAGGAGGAGCGCAACATTATATGACGTGCTTCCAACTT
ACTGTCACCGGCAGCGGAACTCTGGAGCCCAAGGGTGTCACCTTCCCTGAGG
CGTACTCCAAGACTGGTCTCGGTCTTGGTTTCTCCATCCACGCCGACCTCGAC
TCATACCCTGCTCCTGGTCCCGAGCTCATCCAAGCGGTACTGAGGTCACCCCT
CAGCTCCTCACCTTTGGCGAGCTCGCTGGTGCCCCTGCTGCCACCGCCACCGG
TGGTGCCGCCGAGACCCCGGCTGCTTCCACCCCGCTTCGTCGCTGTCTTCTTC
ACC (SEQ ID NO:5)

MHQHNTRDCKEEGIGGAHWGPVLAYMSKVEDAATADGSSEFFKVYQNTWAKN
PDATQGDNDFWGTKDLNYNCGKLDFAIPKNIAPGDYLLRAEAIALHAASAGGG
AQHYMTCFQLTVTGSGTLEPKGVTFPEAYSKTGLGLGFSIHADLDSYPAPGPELI
QGGTEVTPQLLTFGELAGAPAATATGGAAETPAASTPASVAVSSTVAPATSSAA
AEAEPSSVAPVEVSTAVESSVAASSVAASSVVASSVAASSVAASSAASSAAASSA
AAPAESEVAPTPTPEVSSVVAPYPVANSTSSMLPGTASPIVTSSIVAAPTTMLTAV
RPTQTAEASGPIKEYYQCSGQGFKGTGECAEGLECREWNSWYSQCVKPEATKLG
PSKGPMPSSATASKPTATAVAPKPTVEAPKPTAETPKPSPAEPTSAAAAAAEAEP
TSVEPVAVEPSKPATSSAPAAGAGEKTYTLETFIAFLEQEAGSESAAKIRRMIEAL
Q (SEQ ID NO:6)

FIGURE 30

ATGGCACCAAATACAGGTGCCGTTGACAGCACCACAGTGAGGTATAAAAGG
ACCAAGTCGCAATGGGTCCCCGAGGATGTCCAGGCAGCACTTGACTGGTTCA
GCACAACTATCATGTCGCGCTCAAGCTTTCTACAAGTTTCAACACTGCTCTCC
TCCTTTCTGGCACTGACAGCAGGCCAGACACCTGTCAGTTCATCCGATGGCG
GTTGGAGCACCACTCTGGCTGGCACACCTACCGCGTTTCGCTCCGTCTTTACT
CTCCCTCCCTCAGTGGACCAGGGCGTTGAGCAGATCCCCAACATCTACGATC
CGCAAGCTGTCAACGCGCAGGATGTCTGCCCAGGCTACAGGGCATCCGGTCT
TGAACAAGGCCATCGTGGGCTGAGCGCTACCTTGACGCTGGCTGGAGCTGCC
TGCAATGCTTACGGCACCGATATTGAAGAGCTGGACCTGAAGGTTGAATATC
AATCAAAGGGAAGGCTGGCTGTCAGCATTGTACCCAAACATCTTGATGCTAG
CAACCAGTCCCAATGGATTGTGCCCGAGGATCTCATCCCGCGGCCGCAAGCC
GAAGACTCGTCTGAGGGCACAGACCTCAAATTTGACTGGGGCAACGAACCAT
CCTTCTGGTTCAGTGTCGGCCGTCGCTCTACGGGAGATGTCATCTTCACCACC
CAAGGCACGAAGCTCATTTATGAGAACCAATTTGTTGAGTTTGTCAATAACCT
GCCCGAGGACTACAACCTTTACGGTCTCGGAGAACGTATTCACGGACTTCGT
CTGAATAACAACTTCACTGCCACCATCTATGCTGCCGATGTTGGTGACCCAAT
CGACCGCAATCTGTACGGTAGTCACCCCTTCTACCTAGAAACACGCTACTTTG
AAAAAGGCAGCAATGGTAGCAAGACGCCTCTGAAGCAGTCTGAGCTCCAAC
AGCCCAACCTTGGCTATGAAAGCAAACCAGCTGGTTCGCCGTACGAGTCGCG
CTCTCACGGTGTGTACTACCGCAACACGCACGGCATGGATGTCGTTATGAAG
CCTGACCATCTCACATGGAGAACATTGGGAGGTGCAATCGATCTATTCTTCTA
CGAAGGACCCTCTCAACCAGAAGTGACCAAGGAGTACCAGAAGTCGGCGAT
TGGACTGCCTGCCATGCAACAGTACTGGACATTGGGCTTCCATCAATGCCGAT
GGGGATACCGTAATTGGACAGAGACGAGAGAGATTGTTGAGACTATGAGGG
CCTTCAACATTCCCATGGAAACAATTTGGCTCGACATCGATTACATGGATCAA
TACCGAGACTTCACGCTTGATCCCGTGTCGTTTCCTCCATCAGATGTCAAGGA
CTTCTTTGACTGGCTCCATGGGAACAACCAGCACTTCGTACCTATCGTGGATG
CCGCCATCTACATCCCGAACCCACAGAACGCTAGTGACGCTTATGATACCTA
CGCTCGCGGAAATGAATCTGATGTATTCCTGAGGAATCCTGATGGTAGTCAG
TACATTGGCGCTGTGTGGCCTGGATACACCGTCTTCCCAGACTGGCTGTCTTC
CAACGGTGTAGCATGGTGGGTTAAGGAGATGGTTGAGTGGTACAAGGAAGTG
CCGTACAGCGGTTTCTGGGTCGATATGACTGAAGTCTCCTCGTTCTGCGTCGG
TTCCTGCGGTTCCGGTAATGTTACCTTGAACCCTGCTCATCCACCCTTCTCCCT
CCCTGGCGAGGTGGGCAACGTCATTTTCGACTATCCAGAAGGCTTCAACATC
ACCAACGCAACTGAGGCCGCTTCGGCTTCAGCCGGCGCTTCGAGCCAGGCCG
CACCGGCAGCGCCTACGGAGGAGGCTGCTACGACCACTAGCTACTTCCGATC
AACGCCTACACCTGGTGTGCGCAACGTCAACTACCCTCCATACGTCATCAAC
CATGTCCAATCCGGAGCTGATCTTGCTGTCCACGCAGTCAGTCCTAATGCAAC
ACATCAGAATGGCGTTGAAGAGTACGATGTACACAACCTTTATGGTCACCAG
ATCATCAATGCCACCTACCAGGGTCTTCTTCAAGTCTTTCCTGGAAAGCGCCC
GTTTATCATCGGACGTTCCACCTTTGCTGGTAGCGGAAAGTGGGCCGGTCACT
GGGGTGGTGACAACGCGTCCAAGTGGGCTTATATGTTCTTTTCGATCCCTCAG
GCTCTGTCGTTCTCGCTTTTCGGTATTCCCATGTTCGGGGCCGACACTTGCGG

FIGURE 30 (CONTINUED)

ATTCAACGGCAACACTAATATGGAACTTTGCGCTCGCTGGATGCAGCTTTCCG
CCTTCTTCCCCTTCTACCGCAACCACAACGTGCTTTCTGCCATCCCGCAGGAG
CCCTACCGCTGGGACGCCGTAGCTTCTGCATCCAGGACCGCGATGCACATCC
GATACTCGCTACTACCATACATGTACACCCTCTTCAACGACGCCCACACCACC
GGCTCGACCGTCATGCGTGCGCTAGCGTGGGAATTTCCCAATGAGCCTCAGC
TCGCAGGTGTTGACACACAGTTCATGCTGGGTCCTAACATCCTAATTACTCCT
GTTCTTGAGCCCCAGGTCGACACTGTTAATGGAGTATTCCCTGGTATCATCGA
CGGCGAAAGCTGGTTCGACTGGTACTCTGGTGAGCGCGTCGAGGCCGAGGCT
GGCGTCAACACCACCATCTCTGCTCCTCTGGGTCACATCCCCGTGTACATTCG
CGGTGGCTCAGTACTACCGATCCAAGAACCTGGTTACACCACGACTGAGTCC
CGCAAGAACCCATGGGGTCTCATCGTTGCGCTTTCAGCGGATGGTACTGCTTC
CGGTAACCTGTACGTCGATGACGGCGAGTCTCTCGAGCCAGAATCGTGCTTG
GATGTTACGTTCGCTGCTATGAATGGACAACTGAAGGCCGATGTTGAGGGAA
AGTTCAAGGACACGAACGCGCTTGCCAACGTGACCATTCTGGGTGCTCCTTC
AGTTGGACAGGTCAAGTTGAATGGCGAGACAATCGATGCAAGCAAGGTGAG
CTACAACTCTACTAGCAGCGTCCTGAAGCTGTCAGGCTTGAACGACTTGACTA
GTGGAGGAGCTTGGCAGGGAAGCTGGACTCTAAGCTGGGAGTAA (SEQ ID
NO:7)

MAPNTGAVDSTTVRYKRTKSQWVPEDVQAALDWFSTTIMSRSSFLQVSTLLSSF
LALTAGQTPVSSSDGGWSTTLAGTPTAFRSVFTLPPSVDQGVEQIPNIYDPQAVN
AQDVCPGYRASGLEQGHRGLSATLTLAGAACNAYGTDIFELDLKVEYQSKGRL
AVSIVPKHLDASNQSQWIVPEDLIPRPQAEDSSEGTDLKFDWGNEPSFWFSVGRR
STGDVIFTTQGTKLIYENQFVEFVNNLPEDYNLYGLGERIHGLRLNNNFTATIYAA
DVGDPIDRNLYGSHPFYLETRYFEKGSNGSKTPLKQSELQQPNLGYESKPAGSPY
ESRSHGVYYRNTHGMDVVMKPDHLTWRTLGGAIDLFFYEGPSQPEVTKEYQKS
AIGLPAMQQYWTLGFHQCRWGYRNWTETREIVETMRAFNIPMETIWLDIDYMD
QYRDFTLDPVSFPPSDVKDFFDWLHGNNQHFVPIVDAAIYIPNPQNASDAYDTYA
RGNESDVFLRNPDGSQYIGAVWPGYTVFPDWLSSNGVAWWVKEMVEWYKEVP
YSGFWVDMTEVSSFCVGSCGSGNVTLNPAHPPFSLPGEVGNVIFDYPEGFNITNA
TEAASASAGASSQAAPAAPTEEAATTTSYFRSTPTPGVRNVNYPPYVINHVQSGA
DLAVHAVSPNATHQNGVEEYDVHNLYGHQIINATYQGLLQVFPGKRPFIIGRSTF
AGSGKWAGHWGGDNASKWAYMFFSIPQALSFSLFGIPMFGADTCGFNGNTNME
LCARWMQLSAFFPFYRNHNVLSAIPQEPYRWDAVASASRTAMHIRYSLLPYMYT
LFNDAHTTGSTVMRALAWEFPNEPQLAGVDTQFMLGPNILITPVLEPQVDTVNG
VFPGIIDGESWFDWYSGERVEAEAGVNTTISAPLGHIPVYIRGGSVLPIQEPGYTTT
ESRKNPWGLIVALSADGTASGNLYVDDGESLEPESCLDVTFAAMNGQLKADVE
GKFKDTNALANVTILGAPSVGQVKLNGETIDASKVSYNSTSSVLKLSGLNDLTSG
GAWQGSWTLSWE (SEQ ID NO:8)

FIGURE 31

ATGAGGTACACTGCCACCTTCACAGGTGTACTAGCCATCGCCGGTGTCAGCG
CGTGGTCAGTATCCAGTCCTTTCCATATTGAGGGCAACGAGGTTGTCGAGCAT
CTCCATACGGTACCAGAGGGATGGAGAGAGGTTGGTGCTCCAGCGCCTGAGC
ATAAGCTGCATTTCCGCATTGCAGTGCGCTCGGCCAACCGCGATGTATTTGAA
AGGACGCTCATGGAGGTTTCGACTCCTAGCCACCCTCGCTACGGTCAGCACC
TAAAGCGAGACGAACTGAAGCATCTCATCAAGCCTAGAGCCGACTCGACTGC
AAGTGTGCTTACCTGGCTCGAGCAATCCGGTATCGAAGCGCGAGACATCCAG
AACGACGGCGAGTGGATCAACTTTCTCGCACCCGTGAAGCGCGCCGAGCAGA
TGATGGGTACCACGTTCAAGACCTACCAGAGTCAAGCGCGTCCAGCGCTCAA
GAGAACTCGCTCGTTGGGGTACTCTGTGCCCTTGGACGTCCGCAGTCATATTG
ATATGATCCAGCCTACCACTCGCTTCGGTGAAATCCGCCCCGAGTTCAGCCA
AGTCCTTACGCAAAAGACCGCTCCCTTCTCGGTGCTTGCTGTCAATGCCACGT
GCAACACAAGGATCACGCCCGATTGTCTCGCAGATCTGTACAACTTCAAGGA
TTACAACGTTAGTGACAAAGCCGATGTGACAATCGGGGTGAGCGGCTTCCTC
GAGCAGTACGCCCGGTTCAACGATCTCGACCAGTTCATCCAAAGATTTGCTC
CCAGCCTTGCGGGTAAAACGTTCAAAGTCCAGTCTATCAATGGTAAGATGCA
GTCATTGTTACCTCGCTATCTTCAGCTAACGTTCGTAGACGGGCCGTTCCCTC
AAAACTCAACGGCCAACAGCGTTGAGGCTAACCTCGACATCCAGTATACAGC
TGGTCTGGTGTCGCCTAAGATTTCAACCACTTTCTACACTGTTCCAGGACGAG
GACTGTTGGTCCCCGACCTTGACCAACCTGATCTCGAGGACGAGGAGCTGCC
TGAAGTACTGACGACGTCGTACGGTGAGACGGAGCAGAGCGTTCCTGCGGAG
TATGCCAAGAAGGTTTGTGACATGATCGGCCAGCTCGGTACTCGTGGTGTCTC
GGTCATCTTCGAGGATGAATCCACCACAGCCAGCGGTGATACTGGTCCAGGC
TCTGCCTGTCAGAGCAATGACGGCAAGAACGCTACCCGTCTTCAACCAATCT
TCCCAGCTTCATGCCCTACGTTACTTCAGTCGGTGGCACGTTTGGAGTGGAA
CCCGAACGTGCTGTTGAGTTCTCTTCTGGTGGCTTCTCTGATCTCTGGTCTCGC
CCGGCGTACCAAGAGAAGGCAGTGACTGACTACCTTGGCAAACTGGGCTCGC
AATGGCAAGGTTTGTACAACGCCAACGGACGAGGTTTTCCAGATGTCGCGGC
TCAAGGAAAGGGATTTCAGGTCATTGATAAGCTTGGCTTGTCGTCTGTTGGAG
GAACCAGCGCCTCAGCGCCTGTCTTCGCTTCGGTCATTGCGCTTCTGAACAAC
GCTCGTTTGGCGGCTGGTATGCCTTCGCTGGGCTTCTTGAACCCTTGGATCTA
CGAGCAAGGCTACAAGGGCATGAATGATATTGTCGAGGGAGGCTCGCGCGG
ATGCACTGGTCGCTCTATCTATTCCGGGCTTCCCACGCGACTCGTGCCTTACG
CCTCCTGGAATGCGACCGAGGCTGGGATCCCGTCACCGGTTACGGTACACC
CGACTTTGAGCAGATGCTTCGCCTCTCGACTACGCCGCAATACGGTGCGCGTC
GCGTTCGGCGTGGTAGCCTCCGTGGAGAGGCTTAG (SEQ ID NO:9)

FIGURE 31 (CONTINUED)

MRYTATFTGVLAIAGVSAWSVSSPFHIEGNEVVEHLHTVPEGWREVGAPAPEHK
LHFRIAVRSANRDVFERTLMEVSTPSHPRYGQHLKRDELKHLIKPRADSTASVLT
WLEQSGIEARDIQNDGEWINFLAPVKRAEQMMGTTFKTYQSQARPALKRTRSLG
YSVPLDVRSHIDMIQPTTRFGEIRPEFSQVLTQKTAPFSVLAVNATCNTRITPDCL
ADLYNFKDYNVSDKADVTIGVSGFLEQYARFNDLDQFIQRFAPSLAGKTFKVQSI
NGKMQSLLPRYLQLTFVDGPFPQNSTANSVEANLDIQYTAGLVSPKISTTFYTVP
GRGLLVPDLDQPDLEDEELPEVLTTSYGETEQSVPAEYAKKVCDMIGQLGTRGV
SVIFEDESTTASGDTGPGSACQSNDGKNATRLQPIFPASCPYVTSVGGTFGVEPER
AVEFSSGGFSDLWSRPAYQEKAVTDYLGKLGSQWQGLYNANGRGFPDVAAQG
KGFQVIDKLGLSSVGGTSASAPVFASVIALLNNARLAAGMPSLGFLNPWIYEQGY
KGMNDIVEGGSRGCTGRSIYSGLPTRLVPYASWNATEGWDPVTGYGTPDFEQM
LRLSTTPQYGARRVRRGSLRGEA (SEQ ID NO:10)

FIGURE 32

ATGGCTCCTGTGCTCTCGTTCATCGTTGGCTCGCTGTTGGCCTTGCAGGCCTTC
GCCGAGCCATTCGAAAAGCTTTTCGATGTCCCAGAGGGATGGAAGCTCCAAG
GCCCTGCATCGGCTGCGCACACGCTCAAGCTCCAGGTCGCGCTCCAGCAAGG
CGATACCGCCGGCTTTGAGCAGACCGTCATGGAAATGTCCACCCCCTCCAAT
GCAAAGTACGGGCAGCACTTTGAGTCCCACGAGCAAATGAAGCGCATGCTCA
TGCCCAGTGAGGAGACCGTTTCCTCCGTCTCTTCCTGGCTCAAGGCTGCCGGT
ATCAAGAACTTTGAGATTGACGCCGATTGGGTGACCTTCAAGACAACCGTTG
GTGTTGCCAACGAGCTCCTCAGAACCAAGTTCTCCTGGTTTGTCAGCGAGGA
GAGTACGCCTCGCAAAGTTCTCCGCACGCTCGAGTACTCTGTGCCCGACGAC
ATTGCCGACCACATCAACCTCGTTCAGCCGACCACTCGATTCGCTGCTATCCG
TGCGAACCACGAGACAGAGCGCGAGATCTTCGGTATTGCGCTAGCCTCTTCC
CCCAACGTCACTGTCAACTGTGATGCGTCCATCACTCCCCAGTGCTTGAAGCA
GCTCTACAAGATTGACTACACTCCCGACCCCAAGAGTGGCAGTAAGGCAGCT
TTCGCTTCCTATCTCGAGGAGTACGCGCGCTACAGCGACCTCGCCCTCTTCGA
GGAGAACGTCCTCCCCGAGGCTGTGGGCCAGAACTTCTCCGTTGTTCAATTCA
ACGGCGGCTTGAACGACCAAGCCTCTGCCGACGACAGTGGCGAGGCCAACTT
GGATTTGCAGTACATGCTCGGTCTTGCCCAGCCCTGCCTGTTATTGAGTATA
GCACTGGTGGACGTGGCCCATGGATCGCTGACCTCGACCAGCCTGACGAGGC
TGACAGCGCCAACGAGCCCTACCTCGAGTTCCTTCAGTCGGTGCTCAAGCTCC
CACAGAGCGATCTTCCCCAGGTCATCTCCACGTCTTACGGCGAGAACGAACA
AAGCGTACCCAAGTCTTACGCTCTCAGCGTCTGCAACCTCTTCGCTCAACTTG
GTAGCCGTGGTGTCTCTGTCATCTTCTCATCTGGTGATTCCGGTACCGGATCC
GCCTGCCTTTCCAACGACGGCAAGAACACTACCAAGTTCCAGCCTCAGTACC
CCGCTGCCTGCCCATTCGTCACCTCCGTCGGGTCAACTCGCTACCTCAACGAG
ACTGCCACTTTCTTCTCCTCTGGTGGTTTCTCCGACTACTGGAAGCGCCCCAG
CTACCAGGATGATGCCGTCAAGGCATACTTGCATCAACTCGGCCAGAAGAAC
AAGCCCTACTTCAACCGCCACGGGCGCGGATTCCCGGACGTCTCGGCCCAGG
GCTCCGGTTACAGGGTCTACGACAAGGGTTCTCAAGGGGTACCAGGGTAC
TTCATGCTCCGCTCCCGCTTTCGGCGGTATCGTCGCTCTCCTCAATGACGCGC
GTCTGAGGGCCAAGAAGCCTGCTCTTGGTTTCCTGAACCCCCTGCTTTACTCC
AACCCGGATGCGCTCAACGATATCGTTCTTGGTGGCAGCACAGGATGTGATG
GCCACGCGCGCTTCAATGGCAAGCCGAACGGTAGCCCTGTTATCCCGTACGC
GAGCTGGAACGCCACTGCGGGATGGGACCCAGTTTCCGGATTGGGCACGCCA
AACTTCCCCAAGTTGCTCAAGGCTGCTCTTCCCGCTAGGTACAAGGCTTAG
(SEQ ID NO:11)

FIGURE 32 (CONTINUED)

MAPVLSFIVGSLLALQAFAEPFEKLFDVPEGWKLQGPASAAHTLKLQVALQQGD
TAGFEQTVMEMSTPSNAKYGQHFESHEQMKRMLMPSEETVSSVSSWLKAAGIK
NFEIDADWVTFKTTVGVANELLRTKFSWFVSEESTPRKVLRTLEYSVPDDIADHI
NLVQPTTRFAAIRANHETEREIFGIALASSPNVTVNCDASITPQCLKQLYKIDYTP
DPKSGSKAAFASYLEEYARYSDLALFEENVLPEAVGQNFSVVQFNGGLNDQASA
DDSGEANLDLQYMLGLAQPLPVIEYSTGGRGPWIADLDQPDEADSANEPYLEFL
QSVLKLPQSDLPQVISTSYGENEQSVPKSYALSVCNLFAQLGSRGVSVIFSSGDSG
TGSACLSNDGKNTTKFQPQYPAACPFVTSVGSTRYLNETATFFSSGGFSDYWKRP
SYQDDAVKAYLHQLGQKNKPYFNRHGRGFPDVSAQGSGYRVYDKGSLKGYQG
TSCSAPAFGGIVALLNDARLRAKKPALGFLNPLLYSNPDALNDIVLGGSTGCDGH
ARFNGKPNGSPVIPYASWNATAGWDPVSGLGTPNFPKLLKAALPARYKA (SEQ
ID NO:12)

FIGURE 33

ATGTTTGCCAAAACTACTCTCATGAGCGCGCTGCTCAGCGCTGCACTGCCGA
GGTCATCTGGGACGGTCGCTTCAACGACATGACCTCCTCTACCGAACTCTCCG
ACTGGTCCTTCTCCAACCCCGTCGGCAGCTACCAATACTACATCCACGGTCCT
GGCTCCGTAACTGACTACGTAAACCTCGGCGCCACCTTCAAGAACCCCGCCG
ACACAGCTTCCAAGCAAGGTGTCAAGATCACCATCGACGAGACTGCGAAATG
GAACGGCCAAACCATGCTGCGCACCGAACTCATCCCAGAGACCAAGGCCGCC
ATCAACAAGGGCAAAGTCTACTACCACTTCTCCGTCAAGACAACGGCTGAGA
ACGCGCCGACCGCCACCAACGAACACCAAGTCGCTTTCTTCGAGAGCCACTT
CACCGAGTTGAAGTATGGCGCTTCTGGTTCTTCGAACACCAACCTACAATGGC
ACGTTGGTGGCGTCTCCAAGTGGGACGTTGAGCTCGTAGCCGATGAGTGGCA
CAACGTTGCCTACGAAATCGACTTTGATGCCGGTTCCGTCGCATTCTGGCACT
CCACCGGTGCTGATGAGCTCAAGCAGACAGCTGGTCCGTTCGATGCTAGCAC
CTCTTCTAACGGTGCGGACTGGCATCTTGGTGTGCTGAGGCTGCCGGGTAACG
CCGACAAGGATGGTGCTGAGGATTGGTTCTTCAGCGGTGTTGGTAGTGGAGC
TGCTGGTGCGGCCCCAGAAAAGCCTGTTGCCAGTGCTGCTGCACCTTCCAAT
GTCGTTTCTTCTGCTGCTCCTGCTGCTACTACTTCCAAGGCTGCTGTCGCCCCG
GTCTCCTCCAGCGCTGCGGCTGTCGAGACTTCTGTCGTATCCTCCACTGCTGC
TGCTTCTTCCACTGCAGTCCCTGCTGAGACCCCGGCTGTCTCTTCTGCTGCTGC
TATTTCCAGCGCTGCTCCCGTCGAGACTCCCGCCGCCTCTTCTACCTCTGCTGT
CACTCCCGTTGCTACACCTACTGCTGTGGCCGGCTCTGACGCCAAGCTCCCCG
AGGAGTTCACCATCAGCCAATTCGTCGCTTGGCTCAAGGCTAAGACTGGCAA
GAACTAA (SEQ ID NO:13)

MFAKTTLMSALLSAASAEVIWDGRFNDMTSSTELSDWSFSNPVGSYQYYIHGPG
SVTDYVNLGATFKNPADTASKQGVKITIDETAKWNGQTMLRTELIPETKAAINK
GKVYYHFSVKTTAENAPTATNEHQVAFFESHFTELKYGASGSSNTNLQWHVGG
VSKWDVELVADEWHNVAYEIDFDAGSVAFWHSTGADELKQTAGPFDASTSSNG
ADWHLGVLRLPGNADKDGAEDWFFSGVGSGAAGAAPEKPVASAAAPSNVVSS
AAPAATTSKAAVAPVSSSAAAVETSVVSSTAAASSTAVPAETPAVSSAAAISSAA
PVETPAASSTSAVTPVATPTAVAGSDAKLPEEFTISQFVAWLKAKTGKN (SEQ ID
NO:14)

FIGURE 34

ATGTCTACCTCCGAGCTCGCCACCTCTTACGCCGCTCTCATCCTCGCTGATGA
CGGTGTCGACATCACTGCCGACAAGCTCCAGTCTCTCATCAAGGCCGCAAAG
ATCGAGGAGGTCGAGCCCATCTGGACGACCCTGTTCGCCAAGGCTCTTGAGG
GCAAGGATGTCAAGGACCTGCTACTGAACGTCGGCTCAGGCGGCGGCGCTGC
CCCTGCTGCCGGAGGCGCTGCCCCTGCTGCTGGCGGTGCTGCTGAGGCCGCA
CCAGCTGCCGAGGAGAAGAAGGAGGAGGAGAAGGAGGAGTCAGACGAGGA
CATGGGCTTCGGTCTCTTCGACTAA (SEQ ID NO:15)

MSTSELATSYAALILADDGVDITADKLQSLIKAAKIEEVEPIWTTLFAKALEGKDV
KDLLLNVGSGGGAAPAAGGAAPAAGGAAEAAPAAEEKKEEEKEESDEDMGFGL
FD (SEQ ID NO:16)

FIGURE 35

ATGGCTGCACCTCAGTACACCCTGCCTCCGCTGCCATATGCATACAATGCATT
GGAGCCGCACATCTCAGCACAGATCATGGAGCTGCACCACAGCAAGCACCAC
CAGACGTATATCACCAACTTGAATGGTCTTCTCAAGACTCAAGCCGAAGCCG
TTTCTACCTCCGACATCACTTCACAGGTTTCGATACAGCAAGGCATCAAGTTC
AACGCTGGCGGCCACATCAACCACTCTCTCTTCTGGCAAAACCTCGCTCCTGC
CAGCTCGGGTGAGGCTCAGAGCTCCGCTGCTCCTGAGCTACTCAAACAGATC
AAGGCGACTTGGGGAGACGAGGATAAGTTCAAGGAAGCCTTCAACACAGCTT
TGCTAGGCATCCAAGGAAGTGGTTGGGGATGGTTGGTCAAGACCGATATAGG
CAAGGAGCAGAGATTGTCTATCGTGACGACCAAGGACCAGGATCCTGTTGTT
GGTAAAGGCGAAGTTCCGATCTTCGGTGTTGACATGTGGGAGCATGCGTACT
ATCTCCAGTACCAGAATGGTAAGGCTGCTTACGTCAAGAATATCTGGAATGT
CATTAACTGGAAGACGGCGGAGGAGCGTTATCTGGGATCGCGCGCAGATGCT
TTCAGTGTGCTGAGGGCATCCATCTAA (SEQ ID NO:17)

MAAPQYTLPPLPYAYNALEPHISAQIMELHHSKHHQTYITNLNGLLKTQAEAVST
SDITSQVSIQQGIKFNAGGHINHSLFWQNLAPASSGEAQSSAAPELLKQIKATWG
DEDKFKEAFNTALLGIQGSGWGWLVKTDIGKEQRLSIVTTKDQDPVVGKGEVPI
FGVDMWEHAYYLQYQNGKAAYVKNIWNVINWKTAEERYLGSRADAFSVLRAS
I (SEQ ID NO:18)

FIGURE 36

ATGGGCGTGATGAGTGAAAAGGTTGCCAGCTGTATCGACGAGATTGAGGAAT
CCACTCTCAGCACCGAGGGCAAGGTCCAAGCCCAGACTGTTATTACGGAAGA
GCTTAAAAAGCTGCTCAAGCACTGTGCGAATGCAACAGATTGCGTCTATACG
GCTCTCGACTTGCTTCGTAACTCGCTGCATATCAATGAGTCTAATCAGGGCCC
TGACATGAGCATCATTAAAGAGCTGATCGCGGAGAACGCGGTCCGGTTGAGC
ACGCCACGCAAGAGCTGGTTATGGGGTGTCGCAAAAGTCGTGCTTGGAGCAG
TAACGAGTGCAACTATCGCTATCGCGGCGGCGTACCTTTATGGTACCAACGA
TTTTGGTTTGGCACCGCAGACTAACACCAACAGCATGCACCCCAGGTCATTT
CCCTCGTCCAGCGCGCCCAAGCGGTGACCAACCTCACAGGCGAAATCCACTC
CATCAAACTTGAGCATCTAGACCGCCGCTACCAGGAGCTCGAAGGCGCCTCT
GAATCTCACGGTCTCCGAATCGACAACCTGGTCGAAGCACTGGGTGCTCCCA
ATGCAGACGGCACCTACTATTCATCTATGCCGAAACCTGACTGCCAACCTCCT
AGCGATATCCCGATGATCTACGCAAACCCCGATCGCCAGATTGAACGACTGC
GCAGCGAGCTGCAGACCATGCGTAAGAATATTCATCGCATGGACATTCGCCT
CATGAAGCGTCTCAATAAGATCGACCAACGTGGTCTGTGA (SEQ ID NO:19)

MGVMSEKVASCIDEIEESTLSTEGKVQAQTVITEELKKLLKHCANATDCVYTAL
DLLRNSLHINESNQGPDMSIIKELIAENAVRLSTPRKSWLWGVAKVVLGAVTSAT
IAIAAAYLYGTNDFGLAPQTNTNSMHPQVISLVQRAQAVTNLTGEIHSIKLEHLD
RRYQELEGASESHGLRIDNLVEALGAPNADGTYYSSMPKPDCQPPSDIPMIYANP
DRQIERLRSELQTMRKNIHRMDIRLMKRLNKIDQRGL (SEQ ID NO:20)

FIGURE 37

ATGACAACCTTCCTCCTCCGCGATATCCGCATCTTTACCGGCGAGGGGACCAT
CGACAAAGGGTATATTCACGTTCAAAATGGCAAGATAAAGGCTATCGGCCAG
ATAAGCGAGGCTCCGCTGGACTCAGTAAAGACATACTCTAAACCAGGTCATA
CGATTCTTCCAGGGTTGATTGACTGTCACATCCATGCCGACAGGGCCGATCCT
GAAGCTCTACCCCAAGCCCTGCGCTTTGGTGTGACTACCGTTTGCGAGATGCA
CAACGAGCTGGAGAACGTACAAAAGCTGAAGAAGCAGACCATGGAGCCCGA
TACTGCTTCATACAAGACAGCAGGCCAGGCCGCTACTATTGAGAATGGGTGG
CCTATACCCGTCATCACGGCCCACGACAAGACTCCAGAGACTGCAGCGGCGA
TTGCGAAATGGCCAAAACTGACGGATCGGGATAGCGTGGTGGAGTTCCTGGA
ATGGACTGGGAGAGAGATGCAACCAAATTACATCAAACTCATGCACGAAAG
CGGAACTATCATGGGACGCAATTTTAGCTATCCTTCGTTCGAACTGCAAAGTA
CGATCATTGCAGAAGCCAAAAAACGGGGATACTTGACCGTCGCGCACGCTCT
AAGTATGCGTGACACGCTCGAGGTTCTGAATGCAGGTGTCGACGGCCTTACG
CATACGTTTTTCGACCAGCCGCCAACCCAGGAACTAGTAGATGCGTACAAAA
AGAACAACGCATGGGTCAACCCGACACTTGTTGCGATAGGCAGCCTGACGAC
CGAGGGAAAAGAGCTGCAGCATCAATTTGCACACGATCCCAGGGTGAAAGG
GTTGATCAAGGAAGATCGTGTAGGCAACATGTGCAAGTGCATGGGCTTTGCT
GCAGAGGGAGGGAAAGTAGAATACGCATATCAAGGCGTGAAAGGGCTGAGA
GAAGCGGGCATCGACATCCTGTGTGGGAGCGACTCCGCGGGTCCGGCAGTAG
GGACGGCATTTGGTCTATCGATGCATCACGAATTGTATCTCCTCGTAAATAAG
GTGGGAATGACACCTATAGAGGCTTTACGCTCAGCCACAAGCCTGACCGCGA
AGCGCTTCCAATTTAGGGATCGTGGTCGTCTGGCGGAAGGGCTCAACGCCGA
TTTGTTACTGGTAGAAGGAAATCCGCTTGAAGACATTGATGCGACGCTAAAT
ATCCGCGGCGTTTGGCGGGATGGCAACCTTTGTAGCACGTTGTTGAAAAGCTT
GGAGCTGGTGTTGAGCCTCTATTGAGTTGA (SEQ ID NO:21)

MTTFLLRDIRIFTGEGTIDKGYIHVQNGKIKAIGQISEAPLDSVKTYSKPGHTILPG
LIDCHIHADRADPEALPQALRFGVTTVCEMHNELENVQKLKKQTMEPDTASYKT
AGQAATIENGWPIPVITAHDKTPETAAAIAKWPKLTDRDSVVEFLEWTGREMQP
NYIKLMHESGTIMGRNFSYPSFELQSTIIAEAKKRGYLTVAHALSMRDTLEVLNA
GVDGLTHTFFDQPPTQELVDAYKKNNAWVNPTLVAIGSLTTEGKELQHQFAHDP
RVKGLIKEDRVGNMCKCMGFAAEGGKVEYAYQGVKGLREAGIDILCGSDSAGP
AVGTAFGLSMHHELYLLVNKVGMTPIEALRSATSLTAKRFQFRDRGRLAEGLNA
DLLLVEGNPLEDIDATLNIRGVWRDGNLCSTYVEKLGAGVEPLLS (SEQ ID
NO:22)

FIGURE 38

ATGGGCTCCGGATCGTCTGATAGCACCGAGTTCTTCCAGAGCTGGGACTTGTG
GCAGAAGATGACTTTTGTACTGGCTTGCGGAATTGTCGTCACCATCTTCGTTG
GCCTGCTCAAACTCTGGTATGACAAGAACAAGGTTCGCAAGTACAGCAAGGT
CGACAAGGGCAAACGGGCGTCGACGCCCGAAATGCTCGAGGCGCAGCCAGT
AACCCAGGTTCAAGAAGACACCAAAGATGAGATTCCCTTTGGTATCCGCGCA
ATCCAAAGCGGCATCGAGGTTGATGGCGTCTGGATCTCGCGTACCAACACTC
CTGTTGGCAGTAGCCGTGCTTCCATCATGAGCGAACAGCTTCCCCGCAACTTC
AACAACTCCCAGCTCGAGCTGCCCCAGCCAGTCGCCCAGGGTTCAAGCCGCA
ACAGCTCGCGCGCTCCTAGCTCGTTTGACCGTGCCGTCTCCGCCGAGCCTCTT
CCAAGCTACGACTCCCGCGCATCTTCGCCTGGCCGCGGGCACAACCATGAGG
GCCCTCGCTGCAGCAACTGCAACCACCACGTCTCCCGCAACGCTGCGGCCCT
CAGCGCCCTCGAGTCTCCCAACTCTACCCGCAACTCTGCTGCTCCTTCGCCTC
CTCTTCAAGCCAAACACAGCCAGTCTGCAAGCTCCTCGAGCCGACGCACGAG
TGACGAGTCCGACTACATGGCCATTGGGCAAGAC (SEQ ID NO:23)

MGSGSSDSTEFFQSWDLWQKMTFVLACGIVVTIFVGLLKLWYDKNKVRKYSKV
DKGKRASTPEMLEAQPVTQVQEDTKDEIPFGIRAIQSGIEVDGVWISRTNTPVGSS
RASIMSEQLPRNFNNSQLELPQPVAQGSSRNSSRAPSSFDRAVSAEPLPSYDSRAS
SPGRGHNHEGPRCSNCNHHVSRNAAALSALESPNSTRNSAAPSPPLQAKHSQSAS
SSSRRTSDESDYMAIGQD (SEQ ID NO:24)

FIGURE 39

ATGTGCGTGGATGTGTGGGTATGGGAATGGTCGGTGGCCGATGGTGTCGTTC
GCGTGGTGAAGCTCCAACGCGGCGGCCATGGACGCCCGGAACTAGCCGTCGC
CTCGACTGGCCGGACCCTGGGTATGACGCGCTGGCCCCATGCCCATCAGATG
CCTCAAGAGGAGCCCGGAGACGGCAGCACCCACGAAACCGAATCCCAAACG
CGAATGCCGCCCCACAACCAGAGCAGCCAGAGCAAGCGCAAGCACAATCAA
CACAGCCGTCACAAAGAGGTGGCGGACGAGGTGGCAGGGGACGAGGGCAAG
GGCAAGGGCGAGGGCGAGGGCGAGGGCGAGGGGGGCAAGCAGACAGTGAA
AGGCCTTCGCAACCAAATGCTGCCGCTCTCGAATTTGTGCCTTCATCTGTACA
AGAAGCAGCGCATCGAGGAGGAAGACGTGGACGTGGGGG (SEQ ID NO:25)

MCVDVWVWEWSVADGVVRVVKLQRGGHGRPELAVASTGRTLGMTRWPHAH
QMPQEEPGDGSTHETESQTRMPPHNQSSQSKRKHNQHSRHKEVADEVAGDEGK
GKGEGEGEGEGGKQTVKGLRNQMLPLSNLCLHLYKKQRIEEEDVDVG (SEQ ID
NO:26)

FIGURE 40

ATGGCCGCCACCACTACAAATCATGGCACTAACACGCCTCCTAGCACAATGA
CATCCGCACCCACAATACAGCCCAAGTTCCTGCCAAACAGGCATGACCTAGG
CATCGTCGCAGTCGGCTTCAGCGGCGGCCAGCCCAAAGCCGGCGTCGACGCC
GCGCCCATGGCCCTCATCGAAAATGGCCTCATCAAGCAATTAGAAGAAGATC
TAGAATTCTCCGTCACCTACGACGGCCAAGTGCACAACTACACCGAGCTCCA
GCCCTCCGACGACCCAGACTACCGGGGCATGAAGCGCCCCAAGTTCGCCTCG
GCCGTCACAAAGCAAGTCTCTGACCAAGTCTACGAGCACGCCAAGTCGGGCA
AGCTGGTCCTCACCCTCGGCGGCGACCACTCCATCGCCATTGGCACTGTTTCC
GGCACCGCAAAGGCTATTCGCGAGCGGCTGGGCAAGGACATGGCCGTCATCT
GGGTCGATGCGCATGCTGATATTAATACGCCCGAGACGAGCGATTCGGGCAA
CATCCACGGCATGCCCGTGTCTTTCTTGACGGGGCTGGCGACCGAGGAGCGG
GAAGATGTGTTTGGCTGGATTAAAGAGGATCAGAGGATTAGCACGAAGAAG
CTAGTATACATTGGATTGAGGGACATTGATAGTGGAGAGAAGAAGATTCTGA
GGCAGCACGGGATCAAGGCGTTTAGCATGCATGATATTGACAGGCACGGTAT
TGGCAAAATCATGGACATGGCGCTGGGTTGGATCGGAAGCGACACGCCCATC
CATCTCTCCTTCGACGTCGACGCTCTCGACCCCATGTGGGCGCCTAGCACCGG
TACGCCTGTTCGCGGCGGCCTGACGCTGCGCGAGGGCGACTTCATCGCCGAG
TGCGTTGCCGAGACTGGTCAGCTCATTGCCTTGGATCTGGTCGAGGTGAATCC
TAGCCTTGATGCCGAGGGTGCTGGCGACACGGTCCGCGCTGGTGTTTCGATTG
TGAGGTGCGCGCTTGGTGACACGCTTTTGTAG (SEQ ID NO:27)

MAATTTNHGTNTPPSTMTSAPTIQPKFLPNRHDLGIVAVGFSGGQPKAGVDAAP
MALIENGLIKQLEEDLEFSVTYDGQVHNYTELQPSDDPDYRGMKRPKFASAVTK
QVSDQVYEHAKSGKLVLTLGGDHSIAIGTVSGTAKAIRERLGKDMAVIWVDAH
ADINTPETSDSGNIHGMPVSFLTGLATEEREDVFGWIKEDQRISTKKLVYIGLRDI
DSGEKKILRQHGIKAFSMHDIDRHGIGKIMDMALGWIGSDTPIHLSFDVDALDPM
WAPSTGTPVRGGLTLREGDFIAECVAETGQLIALDLVEVNPSLDAEGAGDTVRA
GVSIVRCALGDTLL (SEQ ID NO:28)

FIGURE 41

ATGTACAGGACACTCGCTCTCGCTTCCCTCTCGCTCTTCGGAGCCGCCCGCGC
TCAGCAGGTTGGCAAAGAGACAACGGAGACACACCCCAAGATGACATGGCA
GACTTGCACTGGCACCGGTGGAAAGAGCTGCACCAATAAGCAGGGTTCCATC
GTGCTCGACTCCAACTGGCGATGGTCCCACGTCACCAGCGGATACACCAACT
GCTTCGACGGCAACTCTTGGAACACGACCGCTTGCCCTGATGGCAGCACTTG
CACCAAGAACTGCGCCATCGACGGTGCCGATTACTCTGGCACTTACGGCATC
ACCACCAGCAGCAATGCTCTGACTCTCAAGTTCGTCACCAAGGGCTCTTACTC
TGCCAACATTGGTTCACGTACCTACCTCATGGAGAGTGACACCAAGTACCAA
ATGTTCAATCTCATCGGCAAGGAGTTCACCTTCGATGTCGATGTCTCCAAGCT
GCCTTGCGGTCTGAACGGTGCTCTCTACTTTGTTGAAATGGCCGCCGACGGTG
GCATGAACAAGGGCAACAACAAGGCCGGTGCCAAGTACGGAACCGGATACT
GCGACTCCCAGTGCCCTCACGACATCAAGTTTATCAACGGTGTAGCCAACGT
AGAGGGCTGGAACCCGTCCGACAATGACCCCAACGCCGGCGCTGGTAAGATT
GGTGCTTGCTGCCCCGAAATGGATATCTGGGAGGCCAACTCCATCTCTACTGC
CTACACTCCCCATCCCTGCAAGGGCACTGGTCTTCAGGAGTGCACTGACGAG
GTCAGCTGCGGTGATGGCGACAACCGTTACGGCGGTATCTGCGACAAGGACG
GTTGCGATTTCAACAGCTACCGCATGGGTGTCCGTGACTTCTACGGTCCAGGC
ATGACCCTCGATACCACCAAGAAGATGACTGTCGTCACTCAGTTCCTCGGTTC
CGGTTCCAGCCTCTCGGAGATCAAGCGCTTCTACATCCAGGGAGGAACCGTC
TTCAAGAACTCCGACTCCGCCGTCGAAGGCGTCACTGGTAACTCCATCACTG
AGGAATTCTGTGACCAGCAAAAGACCGTCTTCGGTGACACATCTTCTTTCAAG
ACTCTTGGTGGACTTGATGAGATGGGTGCCTCGCTTGCTCGCGGTCACGTCCT
TGTCATGTCCCTTTGGGACGACCATGCGGTCAACATGCTTTGGCTCGACTCCA
CCTACCCTACCGACGCTGACCCAGAGAAGCCTGGTATCGCCCGTGGTACCTG
CGCTACCGACTCTGGCAAGCCCGAGGACGTCGAGGCCAACTCGCCCGACGCG
ACTGTCATCTTCTCCAACATCAAGTTCGGTCCCATCGGCTCCACCTTTTCCGC
ACCCGCATAA (SEQ ID NO:29)

MYRTLALASLSLFGAARAQQVGKETTETHPKMTWQTCTGTGGKSCTNKQGSIV
LDSNWRWSHVTSGYTNCFDGNSWNTTACPDGSTCTKNCAIDGADYSGTYGITT
SSNALTLKFVTKGSYSANIGSRTYLMESDTKYQMFNLIGKEFTFDVDVSKLPCGL
NGALYFVEMAADGGMNKGNNKAGAKYGTGYCDSQCPHDIKFINGVANVEGW
NPSDNDPNAGAGKIGACCPEMDIWEANSISTAYTPHPCKGTGLQECTDEVSCGD
GDNRYGGICDKDGCDFNSYRMGVRDFYGPGMTLDTTKKMTVVTQFLGSGSSLS
EIKRFYIQGGTVFKNSDSAVEGVTGNSITEEFCDQQKTVFGDTSSFKTLGGLDEM
GASLARGHVLVMSLWDDHAVNMLWLDSTYPTDADPEKPGIARGTCATDSGKPE
DVEANSPDATVIFSNIKFGPIGSTFSAPA (SEQ ID NO:30)

FIGURE 42

ATGCTCTCCAACCTCCTTCTCACTGCTGCGCTTGCAGTAGGCGTGGCTCAGGC
CCTGCCTCAAGCGACAAGTGTCTCGAGGACTACATCTACCGCCCGTGCAACG
ACCACTGCCCCATCAGCAACTGGAAACCCCTTCGCTGGCAAGGATTTCTATG
CCAACCCATACTACTCGTCCGAGGTTTACACCCTAGCCATGCCCTCGCTTGCT
GCGTCTCTGAAGCCCGCTGCTTCTGCCGTGGCCAAAGTCGGTTCATTCGTATG
GATGGACACAATGGCCAAGGTGCCCACCATGGACACGTATCTGGCAGACATC
AAAGCCAAGAATGCCGCAGGTGCAAAGCTGATGGGTACCTTTGTCGTCTACG
ACCTGCCCGACCGCGACTGCGCTGCCCTTGCCTCCAACGGCGAGCTCAAGAT
CGACGACGGTGGTGTAGAGAAGTACAAGACCCAGTACATCGACAAGATTGCC
GCTATTATTAAGGCGTACCCTGACATTAAGATCAACCTCGCCATTGAGCCCGA
CTCGTTGGCCAACATGGTCACCAACATGGGCGTACAAAAGTGCTCGCGCGCC
GCTCCCTACTACAAAGAGCTTACCGCGTACGCTCTCAAGACGCTCAATTTCCC
CAACGTCGACATGTACCTCGACGGTGGCCACGCTGGCTGGCTTGGCTGGGAC
GCCAACATTGGTCCAGCCGCAAAACTCTACGCCGAAGTCTACAAGGCCGCTG
GCTCGCCCCGCGCCGTCCGTGGTATCGTCACCAACGTCAGCAACTACAACGC
CTTCCGCATCGGCACTTGCCCTGCCATCACCCAAGGAAACAAGAACTGCGAC
GAAGAGCGCTTCATCGACGCTTTCGCTCCTCTTCTCCGCGCCGAAGGCTTCCC
TGCCCACTTCATCGTCGACACTGGACGTAGCGGTAAGCAGCCTACTGACCAG
CAGGCCTGGGGAGACTGGTGCAACGTTTCGGGTGCTGGCTTTGGTATTCGTCC
TACTACCAACACCAACAATGCGCTTGTCGATGCTTTTGTCTGGGTCAAGCCTG
GTGGCGAGTCTGATGGTACTTCTGACCAATCTGCTGCTCGCTACGACGGCTTC
TGCGGCAAGGCCTCCGCTTTGAAGCCTGCGCCCGAGGCTGGTACTTGGTTCC
AGGCATACTTTGAGATGTTGTTAAAGAACGCCAACCCCGCTCTTGCATAA
(SEQ ID NO:31)

MLSNLLLTAALAVGVAQALPQATSVSRTTSTARATTTAPSATGNPFAGKDFYAN
PYYSSEVYTLAMPSLAASLKPAASAVAKVGSFVWMDTMAKVPTMDTYLADIKA
KNAAGAKLMGTFVVYDLPDRDCAALASNGELKIDDGGVEKYKTQYIDKIAAIIK
AYPDIKINLAIEPDSLANMVTNMGVQKCSRAAPYYKELTAYALKTLNFPNVDMY
LDGGHAGWLGWDANIGPAAKLYAEVYKAAGSPRAVRGIVTNVSNYNAFRIGTC
PAITQGNKNCDEERFIDAFAPLLRAEGFPAHFIVDTGRSGKQPTDQQAWGDWCN
VSGAGFGIRPTTNTNNALVDAFVWVKPGGESDGTSDQSAARYDGFCGKASALK
PAPEAGTWFQAYFEMLLKNANPALA (SEQ ID NO:32)

FIGURE 43

ATGAAGACAACTTCTTTCGTTCAAGCGGCTTCGCTGCTATCCACTCTTTTCGCT
CCTCTCGCTCTTGCGCAGGAGAAGTTTACCCACGAAGGTACCGGGATTGAGT
TCTGGCGCCAGGTAGTCAGTGACTCCCAGACTGCAGGAGGCTTCGAGTGGGG
CTGGGTATTGCCAGCAGAGCCCACTGGAGCCAACGACGAATACATCGGTTAC
ATTAAAGGTTCGCTGGAAGCGAACAGACAGGGATGGTCCGGTGTCAGCCACG
CTGGTGGCATGGCTAACTCTCTTTTGCTCGTTGCATGGCCGGAAACTGATGCT
GTCAAGACCAAGTTTGTCTGGGCAGGTGGCTATATTGCTCCTGAAGACTACA
CTGGCAACGCGACTTTGAGCCAGATCTTTCACTCAGTCACCGACACACACTTC
GAGATCGTGTACCGATGCGAGCACTGCTGGGTCTGGAATCAGGGTGGTGCTG
AAGGCTCCCAACTCCCCACCAGCGAAGTCAATGTTATCGGCTGGGCCCAGCA
TAACAAAATCTACGACGGCACTTGGGTCTTCCACAACAAGGGACAGTCCCTG
TTTGGTGCTCCTACGGTGGATGCAAGGAACGCGAAGTACTCCGACTATGTCA
AACTGGCAGGAGGCCAGCCATCTGGTGCACCTACACCAACCTTGTCCGGCCA
GCCGTCAGCCACACCCACTCCCACTGCACCGGTAAAGTGCACCGGATCCCCA
GCCCCTTCAGGTTCCTTTGACTACATCGTCATTGGTGGTGGTGCTGGAGGTAT
CCCCATGGCGGACAGGCTTTCCGAGTCTGGCAAGAGCGTTCTCATGCTCGAG
AAGGGCCCGCCGTCCCTCGCTCGTTTGGCGGAAAGATGGGCCCTGAATGGG
CTACCACCAACAATTTGACTCGGTTCGACATCCCTGGTCTCTGCAACCAGATC
TGGGTTGACTCTGCAGGTGTTGCTTGCACCGATATCGACCAAATGGCTGGCTG
TGTCCTTGGTGGAGGTACTGCCGTCAATGCTGCGCTTTGGTGGAAGCCGGTAG
ACATCGATTTCGACTACCAATTCCCCGCTGGCTGGAAATCAGCGGACGTGAA
GGGCGCGATCGACCGTGTGTTCAAGCGCATCCCTGGTACTGATACCCCTTCCG
TGGACGGCAAGCGTTACAAGCAGGAAGGCTTTGATGTCCTATCCGGTGCGCT
TGGTGCGGATGGCTGGAAGAGCGTCGTCGCGAACGACCAACAGAACCAGAA
GAATCGCACATACTCTCACTCTCCGTTCATGTATGACAACGGTCAAAGGCAA
GGACCTCTCGGTACTTACATGGTTTCTGCGCTGGAAAGGAAGAACTTCAAGC
TCTGGACGAACACCATGGCTCGACGCATCGTCCGCACTGGCGGAACGGCTAC
CGGTGTTGAGCTTGAGAGCGGTGTCGGTGGTACTGGTTACTGCGGTACCGTC
AACCTCAACCCTGGAGGCCGTGTTATTGTCTCCGGTGGAGCTTTCGGATCGTC
AAAGGTTCTCTTCCGCAGCGGCATTGGACCAAAGGATCAGCTGAACATCGTG
AAGAACAGCGCTCTCGATGGCTCGACAATGATTGGAGAGTCTGACTGGATTA
ACCTCCCCGTCGGCCAAAACTTGAACGACCACGTCAACACCGATCTTGTTATC
AGGCACCCCAACATCTCTTCCTACAACTTTTACGAGGCGTGGGATGCCCCCAT
CGAGGCTGACAAAGACCTGTACCTTGGCAAGCGTTCTGGTATCCTTGCCCAGT
CTGCACCCAACATCGGCCCCCTTGCTTGGGAAGTGATTACTGGAAGTGACGG
CATTGACCGATCGATCCAGTGGACTGCTCGTGTTGAAGGCCCCGGCGCCAAC
GATACTCACCACCTCACCATCAGCCAGTACCTCGGTCACGGCTCTACTTCGCG
TGGTGCGCTTTCCATCAACGGTGCTCTCAACGTGTATGTCAGCAAATCACCCT
ACCTACAGAACGAGGCCGACACTGGTGTGGTTGTCGCAGGTATCAAGAGCAT
GATGAAGGCCATCCAGAAGAACCCAGCCATCGAGTTCCAAGTACCGCCTGCC
AATATGACAGTTGAGGCATACGTTGCCAGCCTCCCCAAGACCCCAGCTGCCC
GTCGCGCCAACCACTGGATCGGTACCGCCAAGATCGGAACCGACAGCGGTCT
CACGGGTGGAACCTCTGTGGTGGACCTGAACACTCAGGTGTATGGAACGCAG

FIGURE 43 (CONTINUED)

AACATCCACGTAGTCGACGCTTCGCTCTTCCCTGGTCAAATTTTCACCAACCC
TACATCCTACATCATCGTACTCGCAGAACATGCCGCTGCTAAGATTCTCGCAC
TTAGTGCAAGCAGTGGAGGTGGTAAGCCTTCGTCGTCCGCTTGTCGTCCGCA
GTCTCCGCTAAACCCACTACCTCGAAGGCACCAACTGAGTCGTCAACCGTAT
CCGTGGAGCGTCCATCGACACCAGCCAAGTCTTCGGCTAAGTCGACTACTAT
CAAGACATCTGCAGCACCAGCACCTACTCCTACCAGGGTGTCGAAGGCCTGG
GAACGATGCGGTGGTAAAGGCTACACTGGCCCAACAGCTTGTGTCAGTGGGC
ACAAGTGCGCAGTGAGCAATGAGTACTACTCTCAGTGCATCCCTAACTAA
(SEQ ID NO:33)

MKTTSFVQAASLLSTLFAPLALAQEKFTHEGTGIEFWRQVVSDSQTAGGFEWGW
VLPAEPTGANDEYIGYIKGSLEANRQGWSGVSHAGGMANSLLLVAWPETDAVK
TKFVWAGGYIAPEDYTGNATLSQIFHSVTDTHFEIVYRCEHCWVWNQGGAEGS
QLPTSEVNVIGWAQHNKIYDGTWVFHNKGQSLFGAPTVDARNAKYSDYVKLAG
GQPSGAPTPTLSGQPSATPTPAPVKCTGSPAPSGSFDYIVIGGGAGGIPMADRLS
ESGKSVLMLEKGPPSLARFGGKMGPEWATTNNLTRFDIPGLCNQIWVDSAGVAC
TDIDQMAGCVLGGGTAVNAALWWKPVDIDFDYQFPAGWKSADVKGAIDRVFK
RIPGTDTPSVDGKRYKQEGFDVLSGALGADGWKSVVANDQQNQKNRTYSHSPF
MYDNGQRQGPLGTYMVSALERKNFKLWTNTMARRIVRTGGTATGVELESGVG
GTGYCGTVNLNPGGRVIVSGGAFGSSKVLFRSGIGPKDQLNIVKNSALDGSTMIG
ESDWINLPVGQNLNDHVNTDLVIRHPNISSYNFYEAWDAPIEADKDLYLGKRSGI
LAQSAPNIGPLAWEVITGSDGIDRSIQWTARVEGPGANDTHHLTISQYLGHGSTS
RGALSINGALNVYVSKSPYLQNEADTGVVVAGIKSMMKAIQKNPAIEFQVPPAN
MTVEAYVASLPKTPAARRANHWIGTAKIGTDSGLTGGTSVVDLNTQVYGTQNIH
VVDASLFPGQIFTNPTSYIIVLAEHAAAKILALSASSGGGKPSSSALSSAVSAKPTT
SKAPTESSTVSVERPSTPAKSSAKSTTIKTSAAPAPTPTRVSKAWERCGGKGYTGP
TACVSGHKCAVSNEYYSQCIPN  (SEQ ID NO:34)

ID NO:10. The polypeptide can comprise an amino acid
FUNGUS-INDUCED INFLAMMATION AND EOSINOPHIL DEGRANULATION

CROSS-REFERENCE TO RELATED APPLICATIONS

This application is a divisional of U.S. application Ser. No. 12/835,592, filed Jul. 13, 2010, now U.S. Pat. No. 7,887,820 which is a divisional of U.S. application Ser. No. 12/629,638, filed Dec. 2, 2009 (now U.S. Pat. No. 7,815,919), which is a divisional of U.S. application Ser. No. 11/580,454, filed Oct. 13, 2006 (now U.S. Pat. No. 7,662,400), which claims the benefit of U.S. Provisional Application Ser. No. 60/726,553, filed Oct. 14, 2005. The disclosure of the prior applications are considered part of (and are incorporated by reference in) the disclosure of this application.

STATEMENT AS TO FEDERALLY SPONSORED RESEARCH

This invention was made with government support under AI049235 awarded by the National Institute of Allergy and Infectious Diseases. The government has certain rights in the invention.

BACKGROUND

1. Technical Field

This document relates to methods and materials involved in fungus-induced inflammation and eosinophil degranulation. For example, this document relates to isolated nucleic acids encoding fungal polypeptides, fungal polypeptides, methods for assessing fungus-induced inflammation, methods for assessing eosinophil degranulation, and methods for identifying inhibitors of fungus-induced inflammation and/or eosinophil degranulation.

2. Background Information

The National Center for Health Statistics describes the increasingly expensive health care burden that chronic rhinosinusitis (CRS) inflicts in the United States. With an estimated 18 to 22 million cases and at least 30 million courses of antibiotics per year, CRS is one of the predominant chronic diseases in the U.S. In 1996, there were 26.7 million visits to physicians, hospital offices, and emergency departments for sinusitis—at a total cost of $5.8 billion. Sinusitis significantly impacts quality of life, even when compared to typical chronic debilitating diseases, such as diabetes and congestive heart failure. CRS presents a challenge to various medical specialties, including infectious diseases, ear, nose, and throat (ENT), allergy, asthma, and clinical immunology. The FDA has not approved any medication for effective use in CRS. Many antibiotic treatments are prescribed without objective evidence of infection. Roughly 40,000 patients per year undergo sinus surgery, but controlled evidence about the surgical outcomes is lacking. Even with aggressive medical and surgical therapies, many patients have persistent or recurrent disease, leading to frequent courses of antibiotics and multiple surgical interventions.

SUMMARY

This document relates to methods and materials involved in fungus-induced inflammation and eosinophil degranulation. For example, this document relates to isolated nucleic acids encoding fungal polypeptides, fungal polypeptides, methods for assessing fungus-induced inflammation, methods for assessing eosinophil degranulation, and methods for identifying inhibitors of fungus-induced inflammation and/or eosinophil degranulation.

In general, one aspect of this document features a substantially pure polypeptide comprising, or consisting essentially of, an amino acid sequence at least 95 percent identical to the amino acid sequence set forth in SEQ ID NO:2, 4, 6, 8, 10, 12, 14, 16, 18, 20, 22, 24, 26, 28, 30, 32, or 34. The polypeptide can comprise the amino acid sequence set forth in SEQ ID NO:10. The polypeptide can comprise an amino acid sequence having 99% identity to the sequence set forth in SEQ ID NO:10. The polypeptide can comprise the amino acid sequence set forth in SEQ ID NO:12 or 22. The polypeptide can comprise an amino acid sequence having 99% identity to the sequence set forth in SEQ ID NO: 12 or 22.

In another aspect, this document features an isolated nucleic acid comprising, or consisting essentially of, a nucleic acid sequence that encodes a polypeptide comprising an amino acid sequence at least 95 percent identical to the amino acid sequence set forth in SEQ ID NO:2, 4, 6, 8, 10, 12, 14, 16, 18, 20, 22, 24, 26, 28, 30, 32, or 34. The polypeptide can comprise the amino acid sequence set forth in SEQ ID NO:10. The polypeptide can comprise an amino acid sequence having 99% identity to the sequence set forth in SEQ ID NO:10. The polypeptide can comprise the amino acid sequence set forth in SEQ ID NO:12 or 22. The polypeptide can comprise an amino acid sequence having fewer than 5 mismatches as compared to the sequence set forth in SEQ ID NO:10, 12, or 22. The nucleic acid can hybridize under highly stringent hybridization conditions to the nucleic acid sequence set forth in SEQ ID NO:1, 3, 5, 7, 9, 11, 13, 15, 17, 19, 21, 23, 25, 27, 29, 31, or 33. The nucleic acid can hybridize under highly stringent hybridization conditions to the nucleic acid sequence set forth in SEQ ID NO:9, 11, or 21.

In another aspect, this document features a purified antibody having the ability to bind to a polypeptide comprising, or consisting essentially of, an amino acid sequence at least 95 percent identical to the amino acid sequence set forth in SEQ ID NO:2, 4, 6, 8, 10, 12, 14, 16, 18, 20, 22, 24, 26, 28, 30, 32, or 34. The antibody can have a dissociation constant that is less than $10^{-7}$ for the polypeptide. The polypeptide can be a polypeptide having the sequence set forth in SEQ ID NO:10, 12, or 22.

In another aspect, this document features a method of identifying an inhibitor of fungus-induced eosinophil degranulation. The method comprises, or consists essentially of, determining whether or not a test agent reduces the amount of eosinophil degranulation induced by a preparation comprising a polypeptide having an amino acid sequence at least 95 percent identical to the amino acid sequence set forth in SEQ ID NO:2, 4, 6, 8, 10, 12, 14, 16, 18, 20, 22, 24, 26, 28, 30, 32, or 34, wherein the reduction indicates that the test agent is the inhibitor. The polypeptide can be a recombinantly produced polypeptide. The amount of eosinophil degranulation can be determined by measuring major basic protein or eosinophil-derived neurotoxin.

In another aspect, this document features a method of identifying an inhibitor of fungus-induced inflammation. The method comprises, or consists essentially of, determining whether or not a test agent reduces the amount of inflammation induced in a mammal by a preparation comprising a polypeptide having an amino acid sequence at least 95 percent identical to the amino acid sequence set forth in SEQ ID NO:2, 4, 6, 8, 10, 12, 14, 16, 18, 20, 22, 24, 26, 28, 30, 32, or 34, wherein the reduction indicates that the test agent is the inhibitor. The polypeptide can be a recombinantly produced polypeptide.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF THE DRAWINGS

FIG. 3. Serum levels of IgG4 antibodies to *Alternaria* (left) and *Aspergillus* (right) in normal individuals and patients with allergic rhinitis (AR) and CRS. Each dot represents one subject Assay sensitivity, 100 μg/L. Statistical analysis by Mann-Whitney U test.

FIG. 27. Nucleic acid sequence (SEQ ID NO:1) encoding a fungal polypeptide having the amino acid sequence set forth in SEQ ID NO:2.

FIG. 28. Nucleic acid sequence (SEQ ID NO:3) encoding a fungal polypeptide having the amino acid sequence set forth in SEQ ID NO:4.

FIG. 29. Nucleic acid sequence (SEQ ID NO:5) encoding a fungal polypeptide having the amino acid sequence set forth in SEQ ID NO:6.

FIG. 30. Nucleic acid sequence (SEQ ID NO:7) encoding a fungal polypeptide having the amino acid sequence set forth in SEQ ID NO:8.

FIG. 31. Nucleic acid sequence (SEQ ID NO:9) encoding a fungal polypeptide having the amino acid sequence set forth in SEQ ID NO:10.

FIG. 32. Nucleic acid sequence (SEQ ID NO:11) encoding a fungal polypeptide having the amino acid sequence set forth in SEQ ID NO:12.

FIG. 33. Nucleic acid sequence (SEQ ID NO:13) encoding a fungal polypeptide having the amino acid sequence set forth in SEQ ID NO:14.

FIG. 34. Nucleic acid sequence (SEQ ID NO:15) encoding a fungal polypeptide having the amino acid sequence set forth in SEQ ID NO:16.

FIG. 35. Nucleic acid sequence (SEQ ID NO:17) encoding a fungal polypeptide having the amino acid sequence set forth in SEQ ID NO:18.

FIG. 36. Nucleic acid sequence (SEQ ID NO:19) encoding a fungal polypeptide having the amino acid sequence set forth in SEQ ID NO:20.

FIG. 37. Nucleic acid sequence (SEQ ID NO:21) encoding a fungal polypeptide having the amino acid sequence set forth in SEQ ID NO:22.

FIG. 38. Nucleic acid sequence (SEQ ID NO:23) encoding a fungal polypeptide having the amino acid sequence set forth in SEQ ID NO:24.

FIG. 39. Nucleic acid sequence (SEQ ID NO:25) encoding a fungal polypeptide having the amino acid sequence set forth in SEQ ID NO:26.

FIG. 40. Nucleic acid sequence (SEQ ID NO:27) encoding a fungal polypeptide having the amino acid sequence set forth in SEQ ID NO:28.

FIG. 41. Nucleic acid sequence (SEQ ID NO:29) encoding a fungal polypeptide having the amino acid sequence set forth in SEQ ID NO:30.

FIG. 42. Nucleic acid sequence (SEQ ID NO:31) encoding a fungal polypeptide having the amino acid sequence set forth in SEQ ID NO:32.

FIG. 43. Nucleic acid sequence (SEQ ID NO:33) encoding a fungal polypeptide having the amino acid sequence set forth in SEQ ID NO:34.

DETAILED DESCRIPTION

Figure 1:
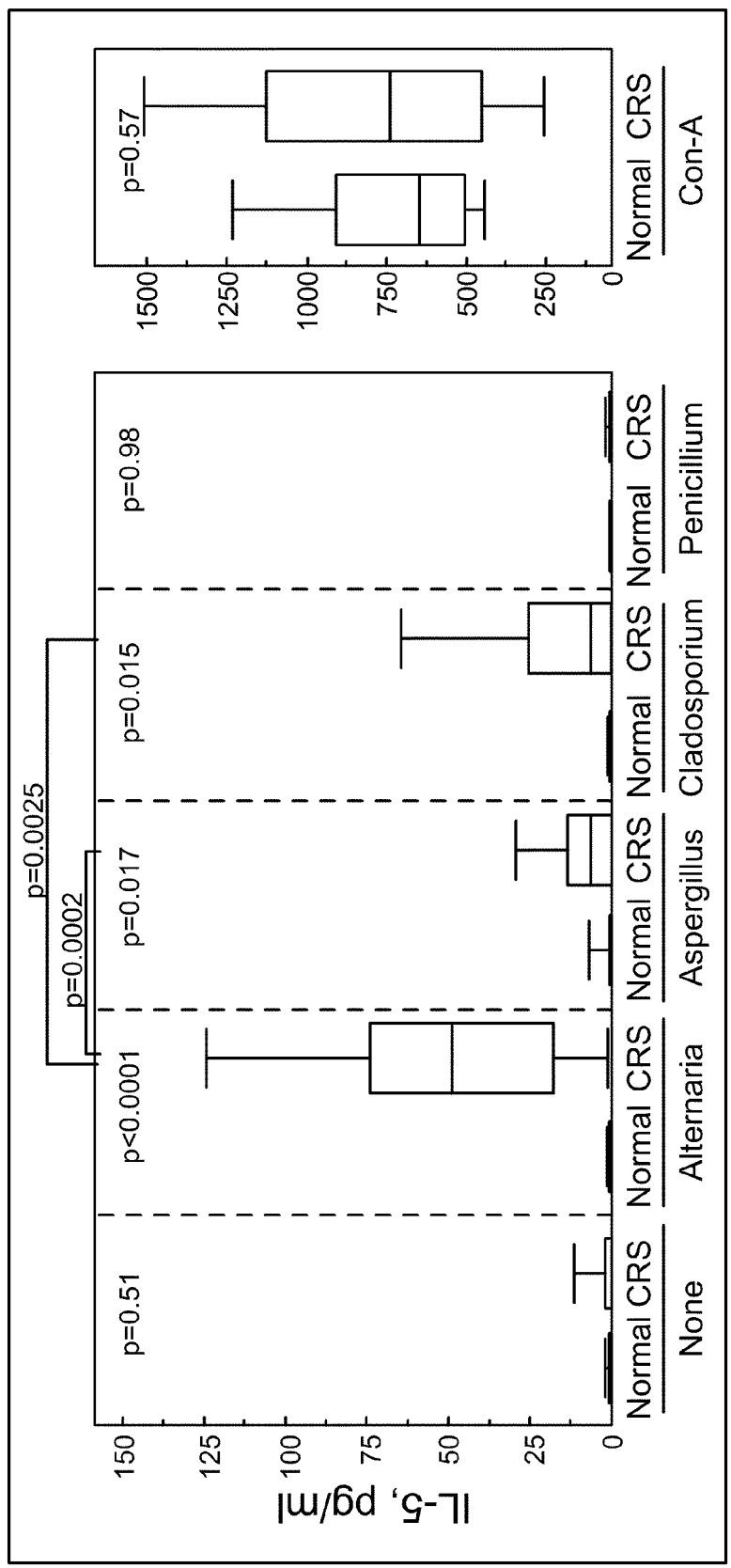
FIG. 1. Production of IL-5 from PBMC from normal individuals (n=15) and patients with CRS (n=18) cultured with extracts of common environmental fungi.

This document relates to methods and materials involved in fungus-induced inflammation and eosinophil degranulation. For example, this document provides isolated nucleic acids encoding fungal polypeptides, substantially pure fungal polypeptides, methods for assessing fungus-induced inflammation, methods for assessing eosinophil degranulation, and methods for identifying inhibitors of fungus-induced inflammation and/or eosinophil degranulation. This document also provides methods and materials for making and using an antibody that can bind a fungal polypeptide. In addition, this document provides methods and materials for treating a mammal having a fungus-induced inflammatory condition (e.g., CRS).

Fungal Polypeptides and Nucleic Acids Encoding Fungal Polypeptides

This document provides a substantially pure fungal polypeptide. Such fungal polypeptides can have the ability to stimulate eosinophil degranulation and/or inflammation. For example a fungal polypeptide provided herein can have the ability to stimulate eosinophil degranulation in vitro, can have the ability to stimulate inflammation in vivo, or both. The term "substantially pure" with respect to a polypeptide refers to a polypeptide that has been separated from cellular components with which it is naturally accompanied. Typically, a polypeptide provided herein is substantially pure when it is at least 60 percent (e.g., 65, 70, 75, 80, 90, 95, or 99 percent), by weight, free from proteins and naturally-occurring organic molecules with which it is naturally associated. In general, a substantially pure polypeptide will yield a single major band on a non-reducing polyacrylamide gel. In some cases, a substantially pure polypeptide can be a polypeptide preparation that contains one of the polypeptides set forth in FIGS. 27-39 or a polypeptide at least about 80 percent identical to such a polypeptide, while being free of at least one of the other polypeptides set forth in FIGS. 27-39.

The polypeptides provided herein can be at least five amino acids in length (e.g., at least 6, 7, 10, 15, 30, 50, 70, or 100 amino acids in length). A substantially pure polypeptide provided herein can be a polypeptide having a sequence that is at least 80 percent identical to the amino acid sequence set forth in SEQ ID NO:2, 4, 6, 8, 10, 12, 14, 16, 18, 20, 22, 24, 26, 28, 30, 32, or 34. For example, a polypeptide provided herein can have at least 80, 85, 90, 95, 98, or 99 percent identity to SEQ ID NO:2, 4, 6, 8, 10, 12, 14, 16, 18, 20, 22, 24, or 26. In some cases, a polypeptide provided herein can have the exact amino acid sequence set forth in SEQ ID NO:2, 4, 6, 8, 10, 12, 14, 16, 18, 20, 22, 24, 26, 28, 30, 32, or 34.

The percent identity between a particular amino acid sequence and the amino acid sequence set forth in SEQ ID NO:2, 4, 6, 8, 10, 12, 14, 16, 18, 20, 22, 24, 26, 28, 30, 32, or 34 is determined as follows. First, the amino acid sequences are aligned using the BLAST 2 Sequences (B12seq) program from the stand-alone version of BLASTZ containing BLASTP version 2.0.14. This stand-alone version of BLASTZ can be obtained from Fish & Richardson's web site (e.g., www.fr.com/blast/) or the State University of New York-Old Westbury Library (call number: QH 447.M6714). Instructions explaining how to use the B12seq program can be found in the readme file accompanying BLASTZ. B12seq performs a comparison between two amino acid sequences using the BLASTP algorithm. To compare two amino acid sequences, the options of B12seq are set as follows: -i is set to a file containing the first amino acid sequence to be compared (e.g., C:\seq1.txt); -j is set to a file containing the second amino acid sequence to be compared (e.g., C:\seq2.txt); -p is set to blastp; -o is set to any desired file name (e.g., C:\output.txt); and all other options are left at their default setting. For example, the following command can be used to generate an output file containing a comparison between two amino acid sequences: C:\B12seq c:\seq1.txt -j c:\seq2.txt -p blastp -o c:\output.txt. If the two compared sequences share homology, then the designated output file will present those regions of homology as aligned sequences. If the two compared sequences do not share homology, then the designated output file will not present aligned sequences.

Once aligned, the number of matches is determined by counting the number of positions where an identical amino acid residue is presented in both sequences. The percent identity is determined by dividing the number of matches by the length of the full-length amino acid sequence set forth in SEQ ID NO:2, 4, 6, 8, 10, 12, 14, 16, 18, 20, 22, 24, 26, 28, 30, 32, or 34 followed by multiplying the resulting value by 100. For example, an amino acid sequence that has 144 matches when aligned with the sequence set forth in SEQ ID NO:26 is 96.0 percent identical to the sequence set forth in SEQ ID NO:26 (i.e., 144÷150*100=96.0).

It is noted that the percent identity value is rounded to the nearest tenth. For example, 78.11, 78.12, 78.13, and 78.14 are rounded down to 78.1, while 78.15, 78.16, 78.17, 78.18, and 78.19 are rounded up to 78.2. It also is noted that the length value will always be an integer.

In some cases, a substantially pure polypeptide provided herein can have fewer than 10 (e.g., fewer than 9, 8, 7, 6, 5, 4, 3, or 2) mismatches as compared to the amino acid sequence set forth in SEQ ID NO:2, 4, 6, 8, 10, 12, 14, 16, 18, 20, 22, 24, 26, 28, 30, 32, or 34. For example, a polypeptide provided herein can have 4, 3, 2, or 1 mismatches as compared to the amino acid sequence set forth in SEQ ID NO:2, 4, 6, 8, 10, 12, 14, 16, 18, 20, 22, 24, 26, 28, 30, 32, or 34.

A substantially pure polypeptide provided herein can be obtained, for example, by extraction from a natural source (e.g., *Alternaria* cells), chemical synthesis, or by recombinant production in a host cell. To recombinantly produce a polypeptide provided herein, a nucleic acid sequence encoding the polypeptide can be ligated into an expression vector and used to transform a bacterial or eukaryotic host cell (e.g., insect, yeast, *Alternaria, Pichia*, or mammalian cells). In general, nucleic acid constructs can include a regulatory sequence operably linked to a nucleic acid sequence encoding a polypeptide provided herein. Regulatory sequences do not typically encode a gene product, but instead affect the expression of the nucleic acid sequence. In bacterial systems, a strain of *Escherichia coli* such as BL-21 can be used. Suitable *E. coli* vectors include the pGEX series of vectors (Amersham Biosciences Corp., Piscataway, N.J.) that produce fusion proteins with glutathione S-transferase (GST). Transformed *E. coli* typically are grown exponentially, and then stimulated with isopropylthio-galactopyranoside (IPTG) prior to harvesting. In general, such fusion proteins can be soluble and can be purified from lysed cells by adsorption to glutathione-agarose beads followed by elution in the presence of free glutathione. The pGEX vectors can be designed to include thrombin or factor Xa protease cleavage sites so that the cloned target gene product can be released from the GST moiety.

In some cases, fungi can be grown in large quantities in vitro, and a polypeptide provided herein that is endogenously produced can be separated and purified using chromatographic methods (e.g., HPL and/or FPLC with a variety of separation matrices). In order to produce recombinant, highly purified forms of a polypeptide provided herein, one method would be to engineer an affinity tag (e.g. 6× Histidine tag) either on the N- or C-terminus of the polypeptide (either via manipulation of the cDNA nucleic acid sequence with PCR mutagenesis, or use of expression vectors containing an affinity tag sequence) to aid in purification. Existing *Pichia pastoris* expression vectors and purification systems like those from Invitrogen (Carlsbad, Calif.) can be used for production of recombinant fungal polypeptides. Moreover, yeast and fungi are closely related organisms and thus recombinantly produced fungal polypeptides in *P. pastoris* can have an increased chance of being properly folded and retain post translation (e.g., glycosylation) modifications involved in activity. *P. pastoris* can be used as described elsewhere (Reichard et al., *Appl. Environ. Microbiol.*, 72(3):1739-48 (2006)). Another method can involve using *Alternaria* itself as a production system. This can be accomplished by engineering an affinity tag on the desired polypeptide and then employing the LME fungal transformation approaches as described elsewhere (Cho et al., *Molecular Plant-Microbe Interact.*, 19:7-15 (2006)).

In eukaryotic host cells, a number of viral-based expression systems can be utilized to express polypeptides provided herein. A nucleic acid encoding a polypeptide provided herein can be cloned into, for example, a baculoviral vector such as pBlueBac (Invitrogen, Carlsbad, Calif.) and then used to co-transfect insect cells such as *Spodoptera frugiperda* (Sf9) cells with wild type DNA from *Autographa californica* multiply enveloped nuclear polyhedrosis virus (AcMNPV). Recombinant viruses producing polypeptides provided herein can be identified by standard methodology. In some cases, a nucleic acid encoding a polypeptide provided herein can be introduced into a SV40, retroviral, or vaccinia based viral vector and used to infect suitable host cells.

Mammalian cell lines that stably express a polypeptide provided herein can be produced using expression vectors with the appropriate control elements and a selectable marker. For example, the eukaryotic expression vectors pCR3.1 (Invitrogen) and p91023(B) (see Wong et al., *Science*, 228:810-815 (1985)) can be used to express a polypeptide provided herein in, for example, Chinese hamster ovary (CHO) cells, COS-1 cells, human embryonic kidney 293 cells, NIH3T3 cells, BHK21 cells, MDCK cells, and human vascular endothelial cells (HUVEC). Following introduction of the expression vector by electroporation, lipofection, calcium phosphate or calcium chloride co-precipitation, DEAE dextran, or other suitable transfection method, stable cell lines can be selected, e.g., by antibiotic resistance to G418, kanamycin, or hygromycin. In some cases, amplified sequences can be ligated into a mammalian expression vector such as pcDNA3 (Invitrogen) and then transcribed and translated in vitro using wheat germ extract or rabbit reticulocyte lysate.

Polypeptides provided herein can be purified by known chromatographic methods including DEAE ion exchange, gel filtration, and hydroxylapatite chromatography. See, e.g., Van Loon and Weinshilboum, *Drug Metab. Dispos.*, 18:632-638 (1990); and Van Loon et al., *Biochem. Pharmacol.*, 44:775-785 (1992). Polypeptides provided herein can be modified to contain an amino acid sequence that allows the polypeptide to be captured onto an affinity matrix. For example, a tag such as c-myc, hemagglutinin, polyhistidine, or Flag™ (Kodak) can be used to aid polypeptide purification. Such tags can be inserted anywhere within a polypeptide including at either the carboxyl or amino terminus. Other fusions that can be useful include enzymes that aid in the detection of a polypeptide, such as alkaline phosphatase. Immunoaffinity chromatography also can be used to purify polypeptides provided herein.

Any suitable method, such as PCR, can be used to obtain an isolated nucleic acid encoding a polypeptide provided herein. The term "nucleic acid" as used herein encompasses both RNA and DNA, including cDNA, genomic DNA, and synthetic (e.g., chemically synthesized) DNA. The nucleic acid can be double-stranded or single-stranded. Where single-stranded, the nucleic acid can be the sense strand or the antisense strand. In addition, nucleic acid can be circular or linear.

The term "isolated" as used herein with reference to nucleic acid refers to a naturally-occurring nucleic acid that is not immediately contiguous with both of the sequences with which it is immediately contiguous (one on the 5' end and one on the 3' end) in the naturally-occurring genome of the organism from which it is derived. For example, an isolated nucleic acid can be, without limitation, a recombinant DNA molecule of any length, provided one of the nucleic acid sequences normally found immediately flanking that recombinant DNA molecule in a naturally-occurring genome is removed or absent. Thus, an isolated nucleic acid includes, without limitation, a recombinant DNA that exists as a separate molecule (e.g., a cDNA or a genomic DNA fragment produced by PCR or restriction endonuclease treatment) independent of other sequences as well as recombinant DNA that is incorporated into a vector, an autonomously replicating plasmid, a virus (e.g., a retrovirus, adenovirus, or herpes virus), or into the genomic DNA of a prokaryote or eukaryote. In addition, an isolated nucleic acid can include a recombinant DNA molecule that is part of a hybrid or fusion nucleic acid sequence.

The term "isolated" as used herein with reference to nucleic acid also includes any non-naturally-occurring nucleic acid since non-naturally-occurring nucleic acid sequences are not found in nature and do not have immediately contiguous sequences in a naturally-occurring genome. For example, non-naturally-occurring nucleic acid such as an engineered nucleic acid is considered to be isolated nucleic acid. Engineered nucleic acid can be made using common molecular cloning or chemical nucleic acid synthesis techniques. Isolated non-naturally-occurring nucleic acid can be independent of other sequences, or incorporated into a vector, an autonomously replicating plasmid, a virus (e.g., a retrovirus, adenovirus, or herpes virus), or the genomic DNA of a prokaryote or eukaryote. In addition, a non-naturally-occurring nucleic acid can include a nucleic acid molecule that is part of a hybrid or fusion nucleic acid sequence.

It will be apparent to those of skill in the art that a nucleic acid existing among hundreds to millions of other nucleic acid molecules within, for example, cDNA or genomic libraries, or gel slices containing a genomic DNA restriction digest is not to be considered an isolated nucleic acid.

A nucleic acid provided herein can be at least about ten nucleotides in length. For example, the nucleic acid can be about 10, 11, 15-20 (e.g., 11, 12, 13, 14, 15, 16, 17, 18, 19, or 20 nucleotides in length), 20-50, 50-100 or greater than 100 nucleotides in length (e.g., greater than 150, 200, 250, 300, 350, 400, 450, 500, 750, or 1000 nucleotides in length). Nucleic acids provided herein can be in a sense or antisense orientation, can be identical or complementary to the nucleotide sequence set forth in SEQ ID NO:1, 3, 5, 7, 9, 11, 13, 15, 17, 19, 21, 23, 25, 27, 29, 31, or 33, and can be DNA, RNA, or nucleic acid analogs. Nucleic acid analogs can be modified at the base moiety, sugar moiety, or phosphate backbone to improve, for example, stability, hybridization, or solubility of the nucleic acid. Modifications at the base moiety include deoxyuridine for deoxythymidine, and 5-methyl-2'-deoxycytidine and 5-bromo-2'-deoxycytidine for deoxycytidine. Modifications of the sugar moiety can include modification of the 2' hydroxyl of the ribose sugar to form 2'-O-methyl or 2'-O-allyl sugars. The deoxyribose phosphate backbone can be modified to produce morpholino nucleic acids, in which each base moiety is linked to a six membered, morpholino ring, or peptide nucleic acids, in which the deoxyphosphate backbone is replaced by a pseudopeptide backbone and the four bases are retained. See, for example, Summerton and Weller, *Antisense Nucleic Acid Drug Dev.*, 7:187-195 (1997); and Hyrup, et al., *Bioorgan. Med. Chem.*, 4:5-23 (1996). In addition, the deoxyphosphate backbone can be replaced with, for example, a phosphorothioate or phosphorodithioate backbone, a phosphoroamidite, or an alkyl phosphotriester backbone.

Nucleic acids provided herein can hybridize, under hybridization conditions, to the sense or antisense strand of a nucleic acid having the nucleotide sequence set forth in SEQ ID NO:1, 3, 5, 7, 9, 11, 13, 15, 17, 19, 21, 23, 25, 27, 29, 31, or 33. The hybridization conditions can be moderately or highly stringent hybridization conditions.

As used herein, moderately stringent hybridization conditions mean the hybridization is performed at about 42° C. in a hybridization solution containing 25 mM $KPO_4$ (pH 7.4), 5×SSC, 5×Denhart's solution, 50 μg/mL denatured, sonicated salmon sperm DNA, 50% formamide, 10% Dextran sulfate, and 1-15 ng/mL probe (about $5 \times 10^7$ cpm/μg), while the washes are performed at about 50° C. with a wash solution containing 2×SSC and 0.1% sodium dodecyl sulfate.

Highly stringent hybridization conditions mean the hybridization is performed at about 42° C. in a hybridization solution containing 25 mM $KPO_4$ (pH 7.4), 5×SSC, 5×Denhart's solution, 50 μg/mL denatured, sonicated salmon sperm DNA, 50% formamide, 10% Dextran sulfate, and 1-15 ng/mL probe (about $5 \times 10^7$ cpm/μg), while the washes are performed at about 65° C. with a wash solution containing 0.2×SSC and 0.1% sodium dodecyl sulfate.

Hybridization can be done by Southern or Northern analysis to identify a DNA or RNA sequence, respectively, that hybridizes to a probe. The DNA or RNA to be analyzed can be electrophoretically separated on an agarose or polyacrylamide gel, transferred to nitrocellulose, nylon, or other suitable membrane, and hybridized with a probe using standard techniques well known in the art such as those described in sections 7.39-7.52 of Sambrook et al., (1989) Molecular Cloning, second edition, Cold Spring harbor Laboratory, Plainview, N.Y. Typically, a probe is at least about 20 nucleotides in length. For example, a probe corresponding to a 20 nucleotide sequence set forth in SEQ ID NO:1, 3, 5, 7, 9, 11, 13, 15, 17, 19, 21, 23, 25, 27, 29, 31, or 33 can be used to identify an identical or similar nucleic acid. In addition, probes longer or shorter than 20 nucleotides can be used. A probe can be labeled with a biotin, digoxygenin, an enzyme, or a radioisotope such as $^{32}P$.

Isolated nucleic acids provided herein also can be chemically synthesized, either as a single nucleic acid molecule (e.g., using automated DNA synthesis in the 3' to 5' direction using phosphoramidite technology) or as a series of oligonucleotides. For example, one or more pairs of long oligonucleotides (e.g., >100 nucleotides) can be synthesized that contain the desired sequence, with each pair containing a short segment of complementarity (e.g., about 15 nucleotides) such that a duplex is formed when the oligonucleotide pair is annealed. DNA polymerase is used to extend the oligonucleotides, resulting in a single, double-stranded nucleic acid molecule per oligonucleotide pair, which then can be ligated into a vector.

Antibodies

An antibody that can bind to a polypeptide provided herein can be made and purified using methods known to those skilled in the art (e.g., the methods described herein). For example, an antibody that can bind to a polypeptide provided herein can be affinity purified from the serum of an animal (e.g., a mouse, rat, rabbit, goat, donkey, horse, duck, or chicken) that received a substantially pure polypeptide provided herein under conditions that illicit an immune response to the polypeptide. In some cases, an antibody that can bind to a polypeptide provided herein can be purified from the supernatant of a B cell hybridoma that produces such an antibody.

An antibody that can bind to a polypeptide provided herein can be monoclonal or polyclonal and can be, for example, a single chain Fv, chimeric antibody, or an Fab fragment.

Fungus-Induced Eosinophil Degranulation

Eosinophils belong to the granulocyte class of white blood cells, and contain cytoplasmic granules that stain with the acidic dye eosin. Eosinophils are the main effectors of antibody-dependent cell-mediated cytotoxicity against multicellular parasites that provoke IgE antibodies. Their role seems to be to engulf and destroy the precipitated antigen-antibody complexes produced in humorally based immune reactions. An elevated eosinophil count usually is seen in allergic reactions, and numerous eosinophils are chemotactically aggregated at sites where antigen-antibody complexes are found.

As used herein, "fungus-induced eosinophil degranulation" refers to eosinophil degranulation in response to one or more antigens from fungal cells (e.g., from fungal cell extracts or fungal culture supernatants). Degranulation is the release of toxic molecules such as eosinophil cationic protein (ECP), eosinophil peroxidase (EPO), and MBP that are contained within eosinophil granules; this release typically causes damage to or death of cells in the vicinity of the degranulating eosinophils.

Eosinophil degranulation can be achieved in vitro as described in the example section herein. In some cases, a fungal preparation (e.g., a fungal cell extract or fungal culture supernatant) can be added to an eosinophil to induce degranulation. As used herein, a "fungal cell extract" is a preparation that contains factors (e.g., polypeptides) found within a fungal cell (e.g., in the cytoplasm, membranes, or organelles of a fungal cell). The term "fungal culture supernatant" refers to media obtained from culturing fungal cells. A fungal culture supernatant can be manipulated to form solid material. For example, a fungal culture supernatant can be obtained by removing fungal organisms from a fungal culture. The resulting supernatant then can be concentrated such that any remaining material (e.g., fungal polypeptides) form concentrated liquid or dry material. This dry material can be a fungal culture extract.

A cell extract or culture supernatant from any suitable type of fungus can be used to induce degranulation, including extracts and supernatants from those fungi listed above (e.g., *Alternaria*, *Candida*, *Aspergillus*, or *Cladisporium*). *Alternaria* cell extracts and culture supernatants are particularly useful. These can be obtained by standard laboratory cell culture and extract preparation techniques. Alternatively, fungal cell extracts and culture supernatants are commercially available (e.g., from Greer Laboratories, Lenoir, N.C.). Eosinophils can be obtained by, for example, purification from an individual's blood. Methods for such purification are known in the art.

Eosinophil degranulation can be stimulated in vitro by, for example, incubating a fungal preparation (e.g., a volume of *Alternaria* culture supernatant or 50 μg/mL of an *Alternaria* culture supernatant extract) with an eosinophil (e.g., purified eosinophils). Any incubation time (e.g., 1, 2, 3, 4, 5, 6, 7, or more hours) can be used. For example, an incubation time from about 2 to about 6 hours can be used. Any amount of a fungal preparation can be used. For example, the amount of a fungal extract can range from about 10 μg/mL to about 100 mg/mL (e.g., about 50, 100, 200, 300, or more μg/mL). Degranulation can be measured by a number of methods, including those known in the art. Degranulation can be assessed by, for example, measuring the release of markers such as ECP, EPO, MBP, or EDN. Non-limiting examples of methods for measuring marker levels include protein-based methods such as ELISA assays and western blotting. Alternatively, degranulation can be assessed by visual inspection of eosinophils by microscopy (e.g., using an electron microscope) to detect the presence of empty granules.

Identifying an Inhibitor of Fungus-Induced Eosinophil Degranulation and/or Inflammation This document provides methods and materials that can be used to identify an agent that inhibits fungus-induced eosinophil degranulation and/or inflammation. For example, an inhibitor of fungus-induced eosinophil degranulation can be identified by contacting an eosinophil with a polypeptide provided herein in the presence and absence of a test agent, and measuring levels of degranulation (e.g., by measuring EDN output or MBP output, or by observing empty granules within eosinophils viewed by microscopy). A test agent can be identified as an inhibitor of eosinophil degranulation if the level of degranulation is reduced in the presence of the test agent as compared to the level of degranulation observed in the absence of the test agent. By "reduced" is meant that the level of degranulation in the presence of the test agent is less (e.g., 1% less, 5% less, 10% less, 50% less, 90% less, or 100% less) than the level observed without the test agent.

Molecules belonging to any of a number of classes can be used as test agents. For example, molecules that are polypeptides (i.e., amino acid chains of any length, regardless of modification such as phosphorylation or glycosylation), oligonucleotides, esters, lipids, carbohydrates, and steroids can be used as test agents. Molecules that are protease inhibitors may be particularly useful. Such protease inhibitors can be included within a cocktail of inhibitors (e.g., inhibitor cocktails that are commercially available from Roche Molecular Biochemicals, Indianapolis, Ind.) or can be individual protease inhibitors (e.g., a single serine protease inhibitor such as AEBSF).

In some cases, an inhibitor of fungus-induced inflammation can be identified by contacting an animal model (e.g., a mouse model) with a polypeptide provided herein in the presence and absence of a test agent, and measuring levels of inflammation. A test agent can be identified as an inhibitor of inflammation if the level of inflammation is reduced in the presence of the test agent as compared to the level of inflammation observed in the absence of the test agent.

The invention will be further described in the following examples, which do not limit the scope of the invention described in the claims.

EXAMPLES

Example 1

The Abnormal Immunologic Response of CRS Patients to Fungal Antigens

Figure 2B:
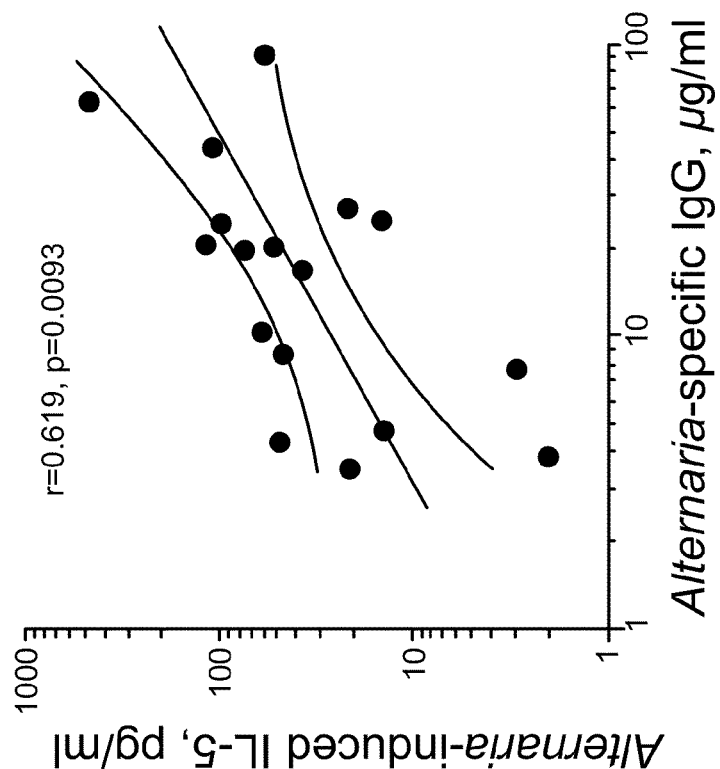
FIG. 2. Correlation between *Alternaria*-specific IgE (A) and IgG (B) in sera and *Alternaria*-induced PBMC production of IL-5 in patients with CRS.
Figure 2A:
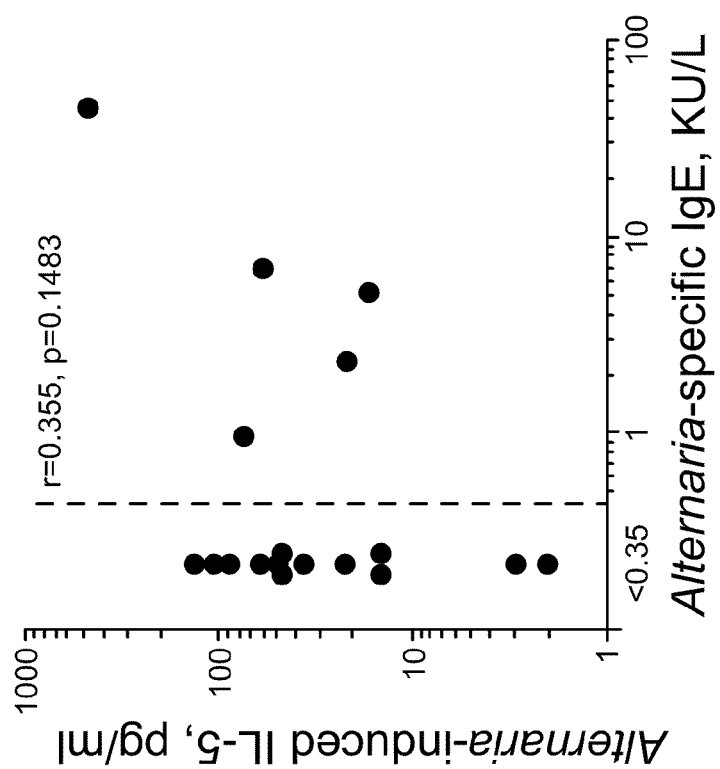

The responses of peripheral blood mononuclear cells (PBMC) from CRS patients to fungal antigens were characterized. The cytokine responses from CRS patients and normal volunteers, when stimulated with extracts from four common environmental fungal species—including *Alternaria, Aspergillus, Cladosporium*, and *Penicillium*, were examined. In the Examples section, *Alternaria* refers to *Alternaria alternate* unless specified otherwise. In FIG. 1, PBMC from about 90% of the CRS patients, but not those from normal individuals, produced both IL-5 and IL-13 when exposed to *Alternaria, Aspergillus*, or *Cladosporium*, but there were no differences in the amounts of these cytokines between allergic and non-allergic CRS patients. In response to *Alternaria*, PBMC from CRS patients produced about 5-times more IFN-γ than PBMC from normal individuals. Furthermore, levels of serum IgG antibodies to *Alternaria* and *Cladosporium* were increased in CRS patients compared to normal individuals ($p<0.01$), and the increased humoral (serum IgG antibody) response strongly correlated with the increased cellular (IL-5 production) response to *Alternaria* ($r=0.619$, $p<0.01$) (FIG. 2). In contrast, <30% of patients had elevated serum levels of IgE antibody to *Alternaria*, and there was no correlation between the serum levels IgE antibody and the cellular response to *Alternaria*. Overall, CRS patients likely exhibit exaggerated humoral and cellular responses, both Th1 and Th2 types, to common airborne fungi, particularly *Alternaria*.

The following was performed to determine why <30% of the CRS patients have IgE antibodies to fungi, while about 90% of them exhibit Th2-like PBMC responses. Production of IgE occurs through sequential switching events from μ to γ4 to ε. With chronic antigen exposure, IgG4-switched B memory cells are induced, and these IgG4-switched B memory cells may undergo a secondary switch to IgE. FIG. 3 shows that 60% of the patients with CRS had specific IgG4 antibodies to *Alternaria*; 20% of patients with seasonal allergic rhinitis (AR) had anti-*Alternaria* IgG4, and none of the normal individuals did. In contrast, there was no significant difference in the levels of IgG4 antibodies to *Aspergillus* among the three groups. Thus, patients with CRS may have had an increased exposure to *Alternaria*, but not to *Aspergillus*, or they may have had an enhanced "modified Th2 response" to *Alternaria*, or both.

Epithelial cells are likely participants among the important cellular network of immune and inflammatory responses in the airways. It was found that nasal polyp epithelial cells obtained from CRS patients produce large quantities of IL-8 and GM-CSF. Conditioned media containing GM-CSF markedly enhanced activation of blood eosinophils, suggesting that the products of not only lymphocytes, but also epithelial cells activate airway eosinophils in nasal polyps.

Example 2

Eosinophil Activation and Degranulation in CRS

Asthma and CRS coexist clinically in >50% of patients with CRS. Histologic specimens from refractory CRS patients undergoing endoscopic sinus surgery were examined. Specimens from all CRS patients (22/22) revealed epithelial changes including shedding and basement membrane thickening. Striking eosinophilic inflammation, which did not differ between allergic and non-allergic patients, was also detected in all CRS patients. These findings, coupled with the clinical coexistence of both diseases, suggest that the same pathologic disease process is manifest as CRS in the upper airway and as asthma in the lower airway.

Figure 4:
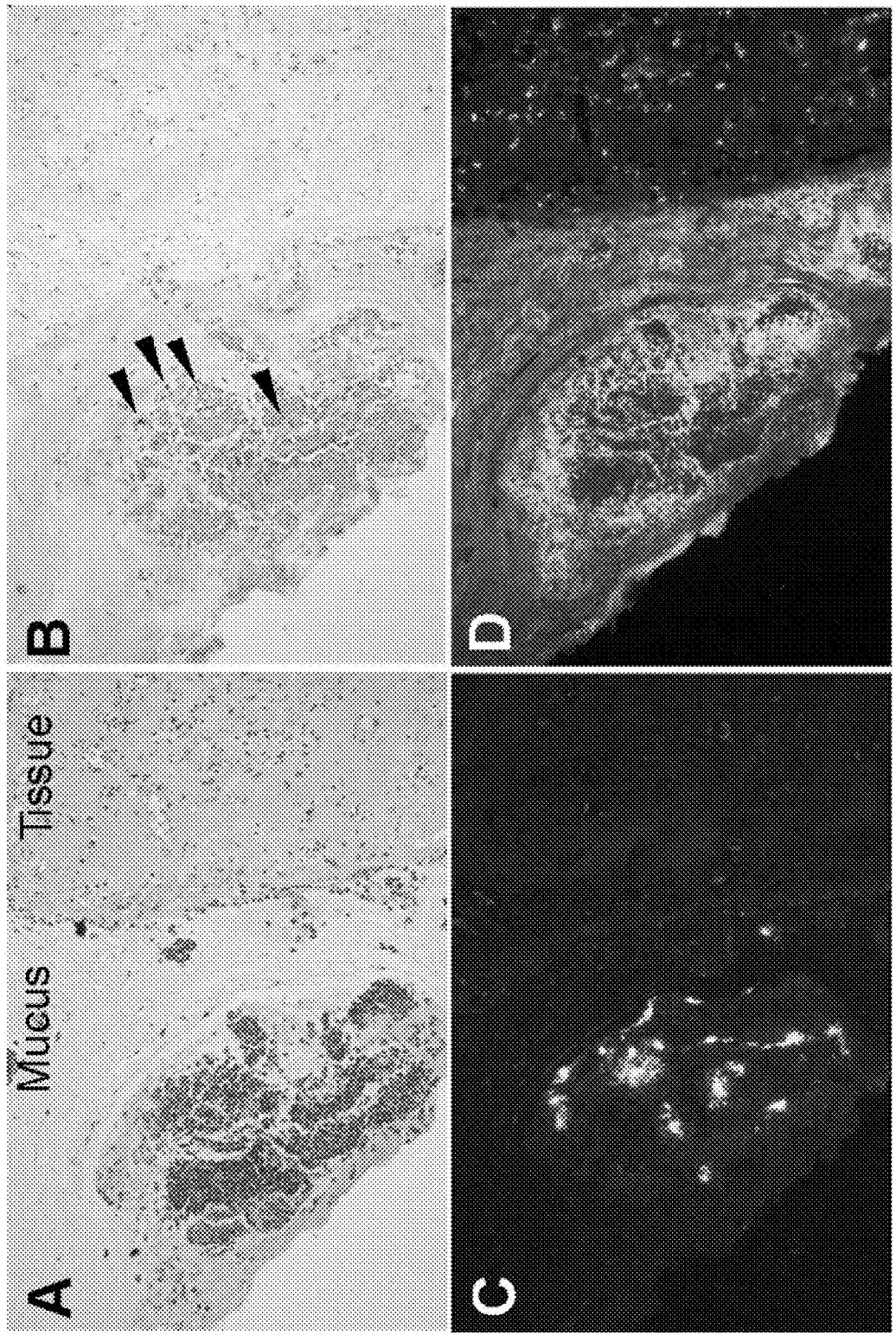
FIG. 4. H&E (A). GMS (B), anti-*Alternaria* (C), and anti-MSP (D) staining of sinus tissue specimen from a patients with CRS. Arrowheads point to GMS-positive fungi, which are barely detectable by this staining. Also note presence of fungal organisms as detected by anti-*Alternaria* Ab (panel C) and diffuse deposition of MBP (panel D) in sinus mucus, but not in sinus tissue.

Eosinophilic inflammation in CRS patients was characterized using specific immunological probes. Conventionally, Grocott-methenamine silver (GMS) staining can detect fungi in pathologic specimens; however, this technique can be inconsistent because it lacks sensitivity and specificity. Chitinase is an enzyme, which selectively and specifically binds to chitin in fungal cell walls. Fluorescein-labeled chitinase was used and detected one or more fungal hyphae within the sinus mucus of 54/54 (100%) of consecutive surgical patients with CRS. Fungi were in the airway lumen but not within the airway tissues, suggesting that CRS is not an invasive fungal infection. Because PBMC from CRS patients exhibited vigorous cytokine responses to *Alternaria* (FIG. 1), a polyclonal antibody to *Alternaria* was used to investigate the presence of fungi in sinus specimens from CRS patients. Rabbits were immunized with crude *Alternaria* extract, and as expected, this anti-*Alternaria* cross-reacted with other fungi, including *Aspergillus, Cladosporium*, and *Penicillium*, but not with bacteria. In FIG. 4C, anti-*Alternaria* antibody clearly visualized fungal hyphae and fungal products in the clusters of inflammatory cells (i.e., eosinophils) within the sinus lumen.

To characterize the extent and location of eosinophilic inflammation, antibody to eosinophil major basic protein (MBP) were used. All tissue specimens from CRS patients exhibited intact eosinophils, but diffuse extracellular MBP deposition, as a marker of eosinophil degranulation, was rare. In contrast, all mucus specimens exhibited abundant diffuse extracellular MBP deposition within or around the clusters of eosinophils (FIG. 4D). Thus, release and deposition of the toxic MBP from eosinophils seem to occur mainly within the airway lumen, but not in airway tissues. This observation and the presence of fungal hyphae and fungal products within the airway lumen suggested that the eosinophilic inflammation of CRS may be part of a normal, but clearly exaggerated, immune response to environmental and airborne fungal organisms. The activation mechanisms of eosinophils in vivo in CRS and asthma have been poorly understood.

Figure 5:
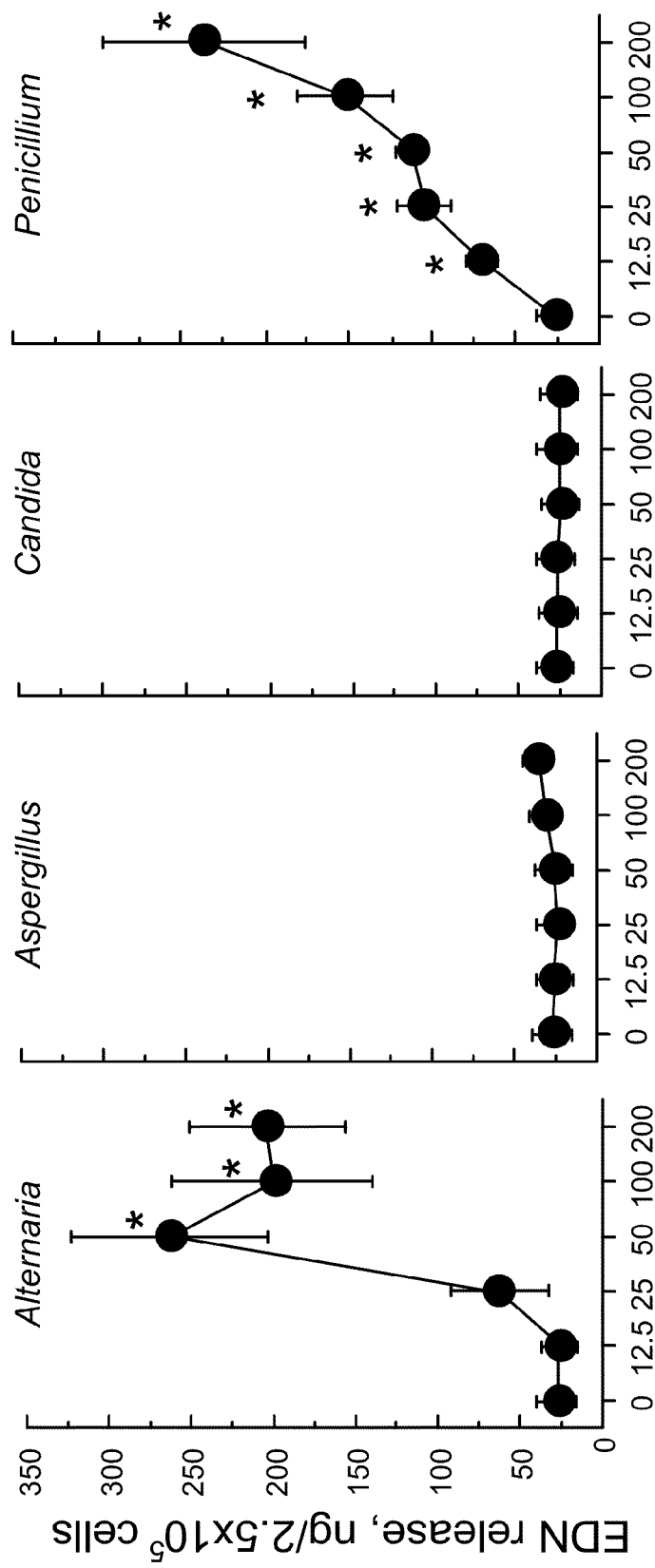
FIG. 5. Effects of fungi on eosinophil degranulation. Eosinophils were incubated with culture extracts of various fungi for 3 hours. EDN concentrations in the supernatants were measured by RIA as an indicator of degranulation. *, p<0.05 compared to medium alone, n=5.
Figure 6A:
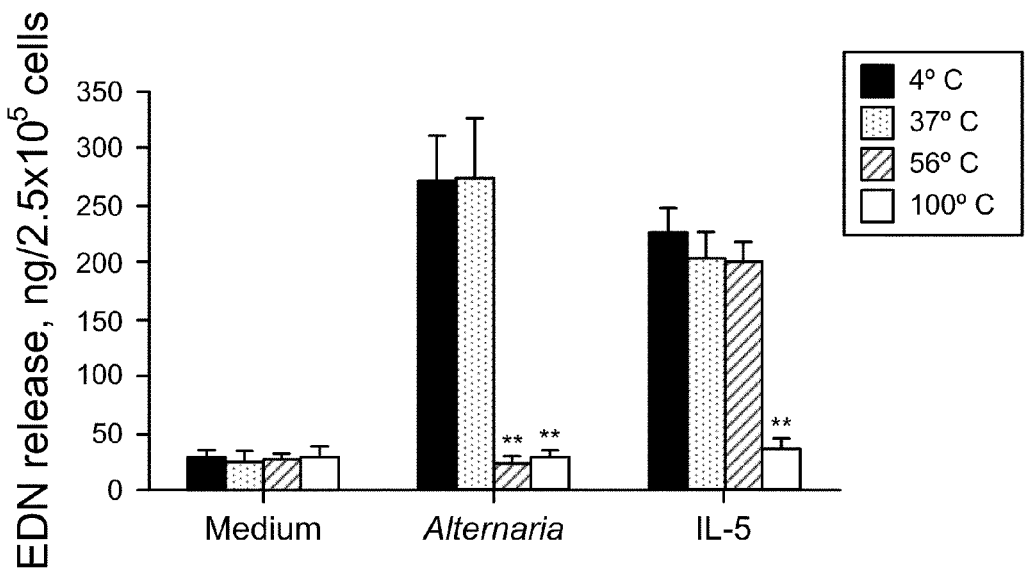
FIG. 6. Characterization of activity in *Alternaria* extract. Panel A, *Alternaria* extracts were treated at various temperatures before incubation with eosinophils. Panel B, size exclusion chromatography with Superdex 200-10/30 column.
Figure 6B:
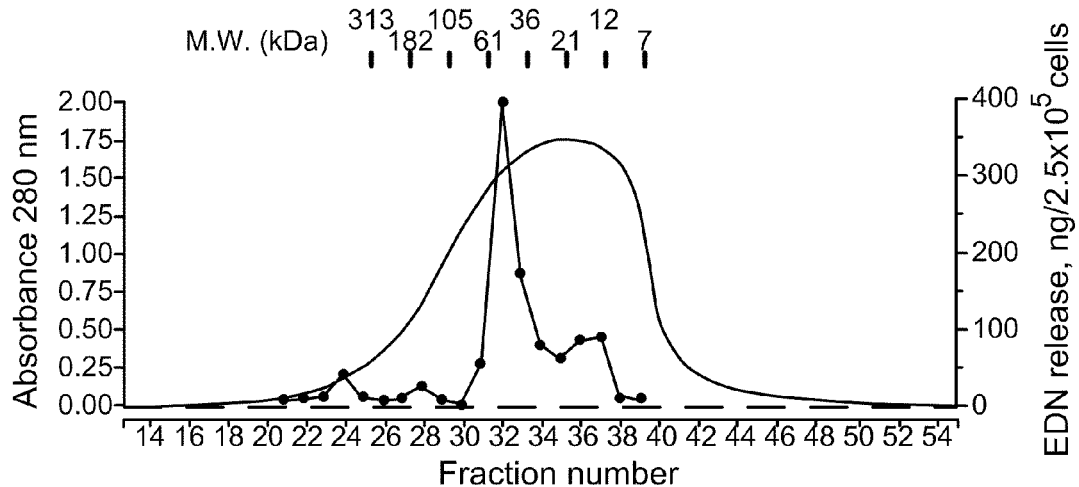

The following was performed to determine whether human eosinophils have an innate capacity to respond to environmental fungal organisms. Human eosinophils were incubated with extracts from common environmental airborne fungi. As shown in FIG. 5, *Alternaria* and *Penicillium* induced remarkable degranulation (e.g., eosinophil-derived neurotoxin (EDN) release) of eosinophils from normal healthy individuals. No opsonization or sensitization with IgE or IgG antibodies was necessary. *Alternaria* also strongly induced other activation events in eosinophils from healthy individuals, including increases in intracellular calcium concentration ([Ca2+]i), cell surface expression of CD63 and CD11b, and production of IL-8. *Alternaria* did not induce neutrophil activation, suggesting cellular specificity of the *Alternaria* response. The *Alternaria*-induced eosinophil [Ca2+]i response and degranulation was pertussis toxin (PTX)-sensitive. The eosinophil-stimulating activity in *Alternaria* extract was heat-labile, inactivated by heat treatment at 56° C. for 30 minutes, and had a molecular mass about 30-50 kDa (FIG. 6). Thus, eosinophils, but not neutrophils, likely possess G protein-dependent cellular activation machinery that directly responds to an *Alternaria* protein or glycoprotein product(s).

Figure 7:
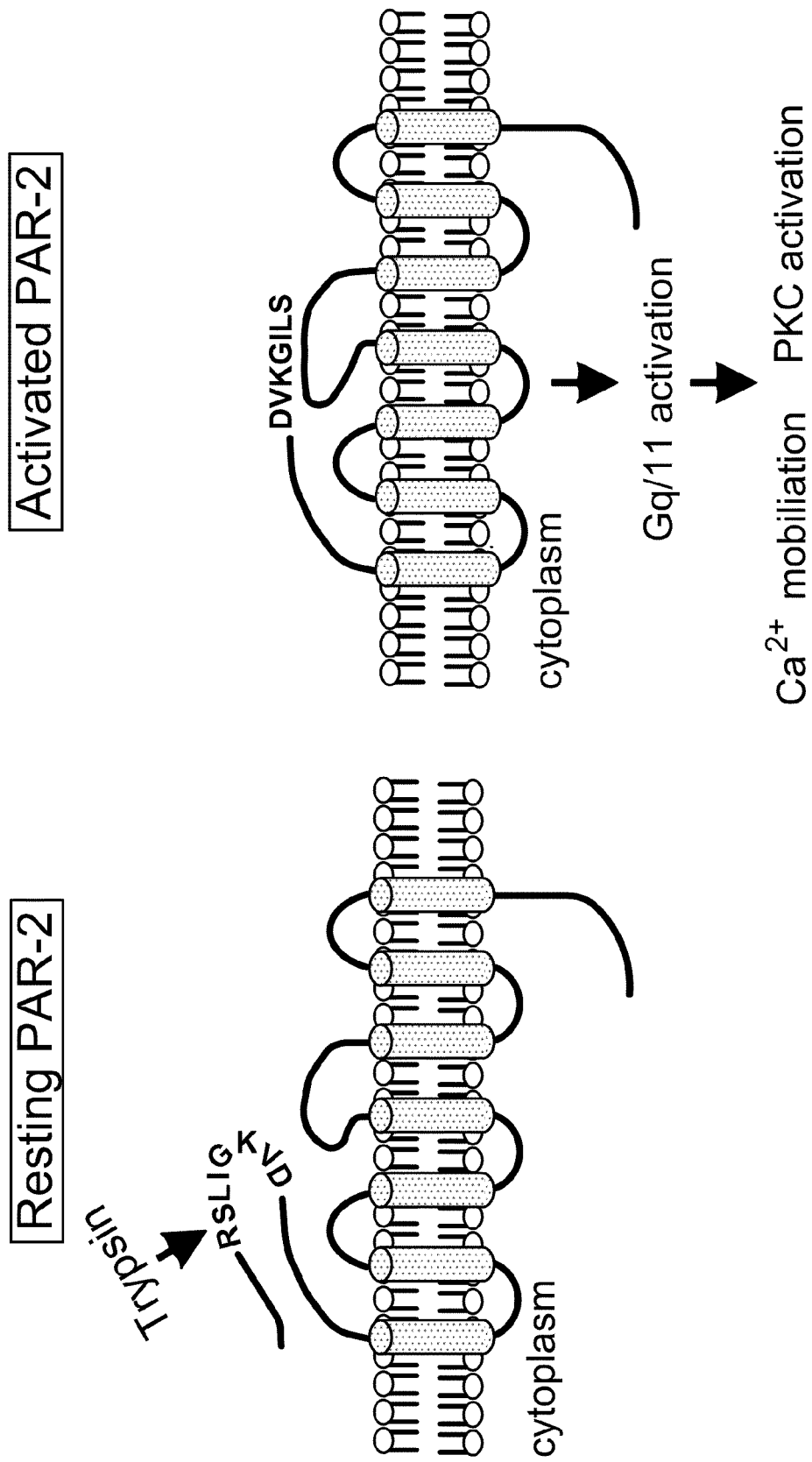
FIG. 7. Mechanism of PAR-2 activation.

The following was performed to examine whether eosinophils can respond to proteases. Protease-activated receptors (PARs) are a unique class of G protein-coupled seven transmembrane receptors, which are activated by proteolytic cleavage of the amino terminus of the receptor itself (FIG. 7). Four members of this family, including PAR-1, -2, -3, and -4, have been described elsewhere. In the case of PAR-2 (FIG. 7), proteolytic cleavage by a certain protease (e.g., trypsin) exposes its new N-terminus (SLIGKV; SEQ ID NO:38), which binds to the ligand-binding site in the second extracellular loop and results in activation of downstream events. Human eosinophils were found to express PAR-2 constitutively and found to be activated by serine and cysteine proteases, such as trypsin and papain, through this receptor. Eosinophils were also activated by a natural mite allergen protease, Der f1. PAR-2 may serve as an eosinophil receptor to recognize and respond to proteases from allergens, resulting in active release of pro-inflammatory mediators.

Example 3

Test Hypothesis that Fungi Colonized in Paranasal Sinus and Nasal Cavities are Involved in Persistent Eosinophilic Inflammation in CRS To examine the clinical significance of fungal colonization in CRS, two clinical trials were performed to examine the efficacy of anti-fungal agents. It was hypothesized that antifungal agents will reduce the fungal burden in the upper airways, resulting in less antigenic stimulation of immune cells, less airway inflammation, and improved clinical outcomes. The first aim was to establish the safety and demonstrate potential clinical efficacy of intranasal antifungal drug therapy in patients with CRS in a pilot trial. This prospective, open-label trial used amphotericin B as a medical treatment in 51 randomly selected CRS patients. The antifungal was applied intranasally using 20 mL of a 100 µg/mL solution twice daily for a mean of 11 months (minimum of 3 months). Using amphotericin B, improvement of sinusitis symptoms was observed in 38/51 (75%) of patients. Endoscopically, 18/51 (35%) patients became disease free and an additional 20/51 (39%) improved by at least one stage. No effect was seen in 13/51 (25%) patients. The available CT scans pre- and post-treatment (n=12) demonstrated a significant reduction in the inflammatory mucosal thickening. Thus, this open-label pilot trial demonstrated that direct muco-administration of an antifungal drug is both safe and potentially effective to treat patients with CRS.

Second, to address the efficacy of intranasal antifungal agents more objectively, a randomized, placebo-controlled, double-blind, single center trial was performed to treat 30 randomly selected CRS patients. Patients instilled 20 mL amphotericin B (250 µg/mL) or placebo to each nostril twice daily for 6 months. Twenty-four patients completed the 6 months of treatment. Patients receiving amphotericin B showed reduced mucosal thickening on CT scans compared to placebo (p=0.030). Between group comparisons of the changes in the intranasal mucus levels of EDN, as a marker of eosinophilic inflammation, showed a reduction in the amphotericin B group and an increase in the placebo group (p=0.046). The changes in the endoscopic scores improved in the amphotericin B group compared to placebo (p=0.038). While the group comparison showed statistically significant differences, careful examination of individual patient data in the amphotericin B group showed a spectrum of efficacy. Some patients responded well to the treatment, but others not as well. Thus, fungi may be important in the development of CRS in certain patients.

Example 4

Mechanisms and Molecules Involved in Eosinophil Degranulation in Response to *Alternaria*

Figure 8A:
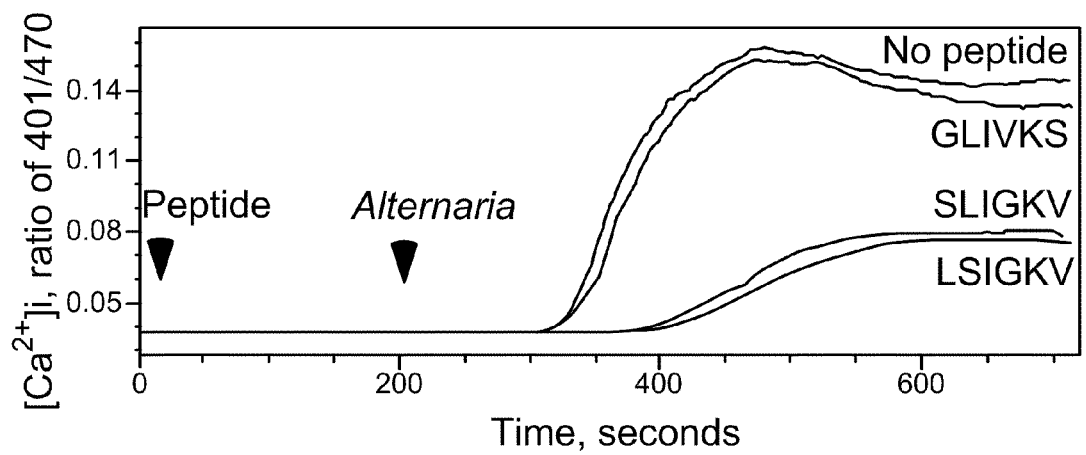
FIG. 8. Desensitization of eosinophil calcium response (Panel A) and EDN release (Panel B) by PAR-2 peptides. Cells were preincubated with PAR-2 agonist (SLIGKV; SEQ ID NO:38), PAR-2 antagonist (LSIGKV; SEQ ID NO:35) or control peptide (GLIVKS; SEQ ID NO:36) (all at 100 μM) before stimulation with *Alternaria* extract (Panel A) or with *Alternaria* extract, PAF or PMA (Panel B).
Figure 8B:
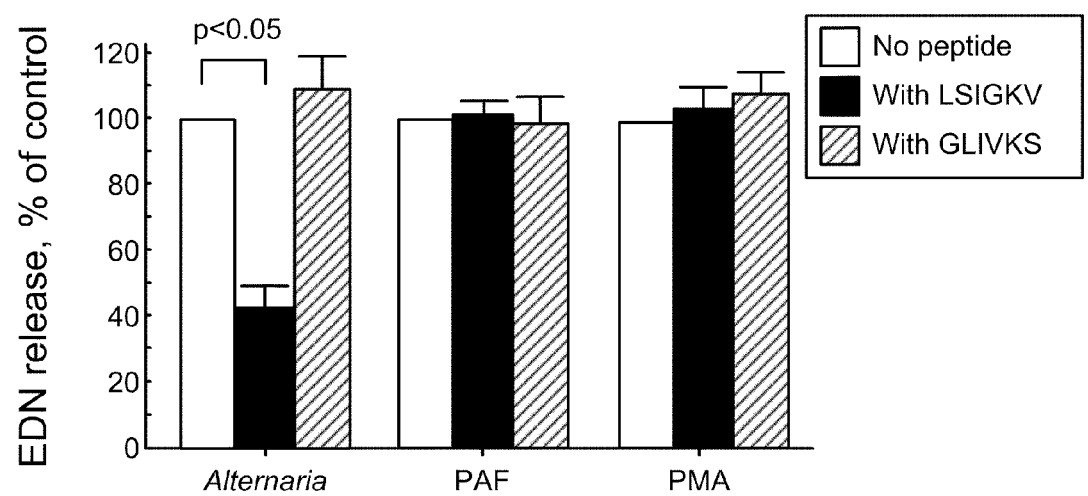

The majority of previous studies in anti-fungal immune responses used the following models: animal infection in in vivo systems (e.g., *Candida albicans, Aspergillus fumigatus*), or entire fungal hyphae or conidia (e.g., *C. albicans, A. fumigatus*), a yeast model (e.g., zymosan), and isolated fungal carbohydrate macromolecules (e.g., β-glucan, mannan) in in vitro systems. These studies pointed to roles for TLRs, in particular TLR2 and TLR4, and to other pattern recognition receptors that immune cells, such as macrophages and neutrophils, use to recognize fungi. Because eosinophils express little TLR2 or TLR4 and the active component(s) in *Alternaria* extract was a heat-labile molecule(s) with an approximate 30-50 kDa molecular mass (FIG. 6), it was speculated that an *Alternaria*-derived protease(s) (not carbohydrates), interacting with eosinophil PAR-2, may be involved in the eosinophils' responses to *Alternaria*. Sine no specific small molecule inhibitor for PAR-2 is available, a desensitization approach was used. As shown in FIG. 8, pre-incubation of eosinophils with the PAR-2 agonistic peptide, SLIGKV (SEQ ID NO:38), significantly inhibited the eosinophils' calcium response to *Alternaria* extract. Similarly, an N-terminal reversed peptide (LSIGKV; SEQ ID NO:35), which is known to inhibit activation of PAR-2, also inhibited the eosinophils' calcium response to *Alternaria*; a control scramble peptide (GLIVKS; SEQ ID NO:36) showed no effects. Eosinophil degranulation induced by *Alternaria* extract was also significantly and specifically inhibited by the LSIGKV (SEQ ID NO:35) peptide (FIG. 8, panel B). In contrast, degranulation induced by PAF or PMA was not affected by the LSIGKV (SEQ ID NP:35) peptide. Thus, PAR-2 is likely involved in the eosinophils' calcium and degranulation responses to *Alternaria* extract.

Figure 9A:
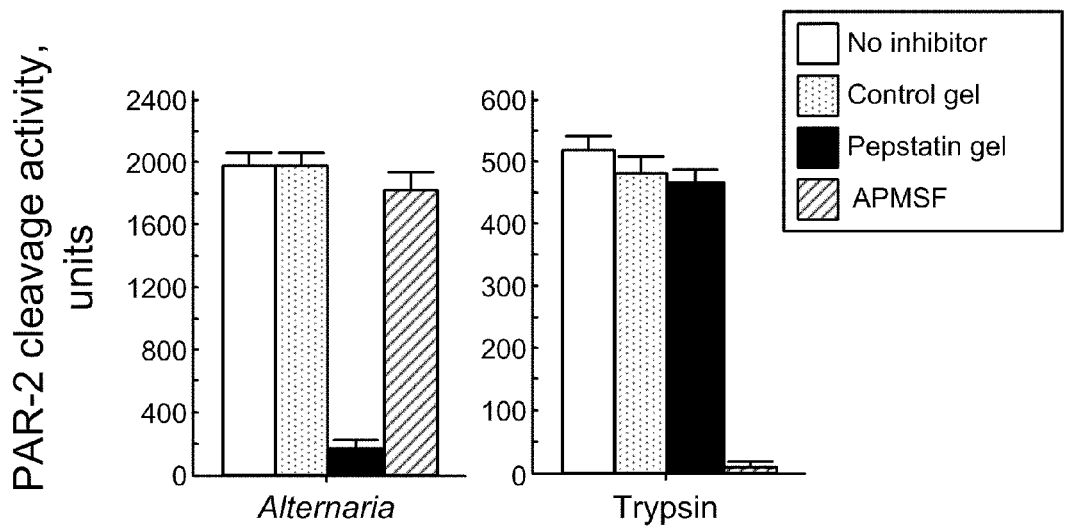
FIG. 9. Effects of protease inhibitors on PAR-2 cleavage activity (Panel A) and EDN release activity (Panel B) of *Alternaria* extract. *Alternaria* extract, trypsin, or PMA was pretreated with pepstatin A agarose, control agarose, or APMSF, and added to the PAR-2 peptide substrate (Panel A) or eosinophils (Panel B). In Panel B, *, p<0.05 compared to no inhibitors, n=4.
Figure 9B:
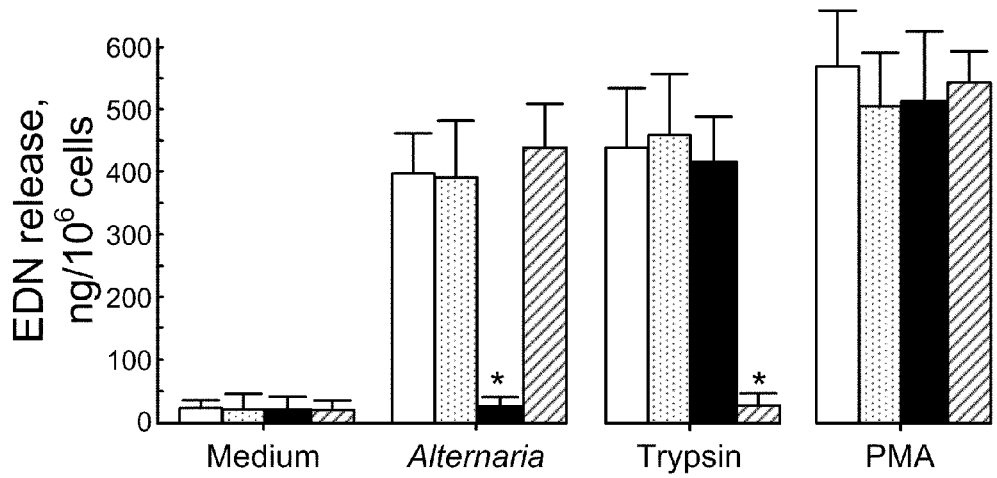

A search through a current database of known *Alternaria* allergens did not reveal any relevant proteases. A fluorescent quenched peptide substrate (Abz-SKGRSLIGK(Dnp)D) (SEQ ID NO:37), which spans the trypsin-cleavage site (between R and S) of PAR-2 was synthesized, and used it in an in vitro assay for PAR-2 cleavage and activation. As shown in FIG. 9, trypsin, as positive control, clearly cleaved this peptide, and a serine protease inhibitor, APMSF, inhibited the activity. *Alternaria* extract also potently cleaved this peptide, but it was insensitive to APMSF. *Alternaria*'s activity was abolished when aspartate protease(s) was removed from the extract by pepstatin A agarose (FIG. 9); pepstatin A is a highly specific inhibitor for aspartate protease. Furthermore, eosinophil degranulation induced by *Alternaria* extract was significantly inhibited by pepstatin A agarose, but not by control agarose or APMSF. Thus, an aspartate protease(s) in *Alternaria* extract, but not a serine protease(s), may be involved in the activation of eosinophils through PAR-2. this observation was confirmed by using other aspartate protease inhibitors, including alkalo-thermophilic *bacillus* inhibitor (ATBI), nelfinavir, and ritonavir.

Figure 10:
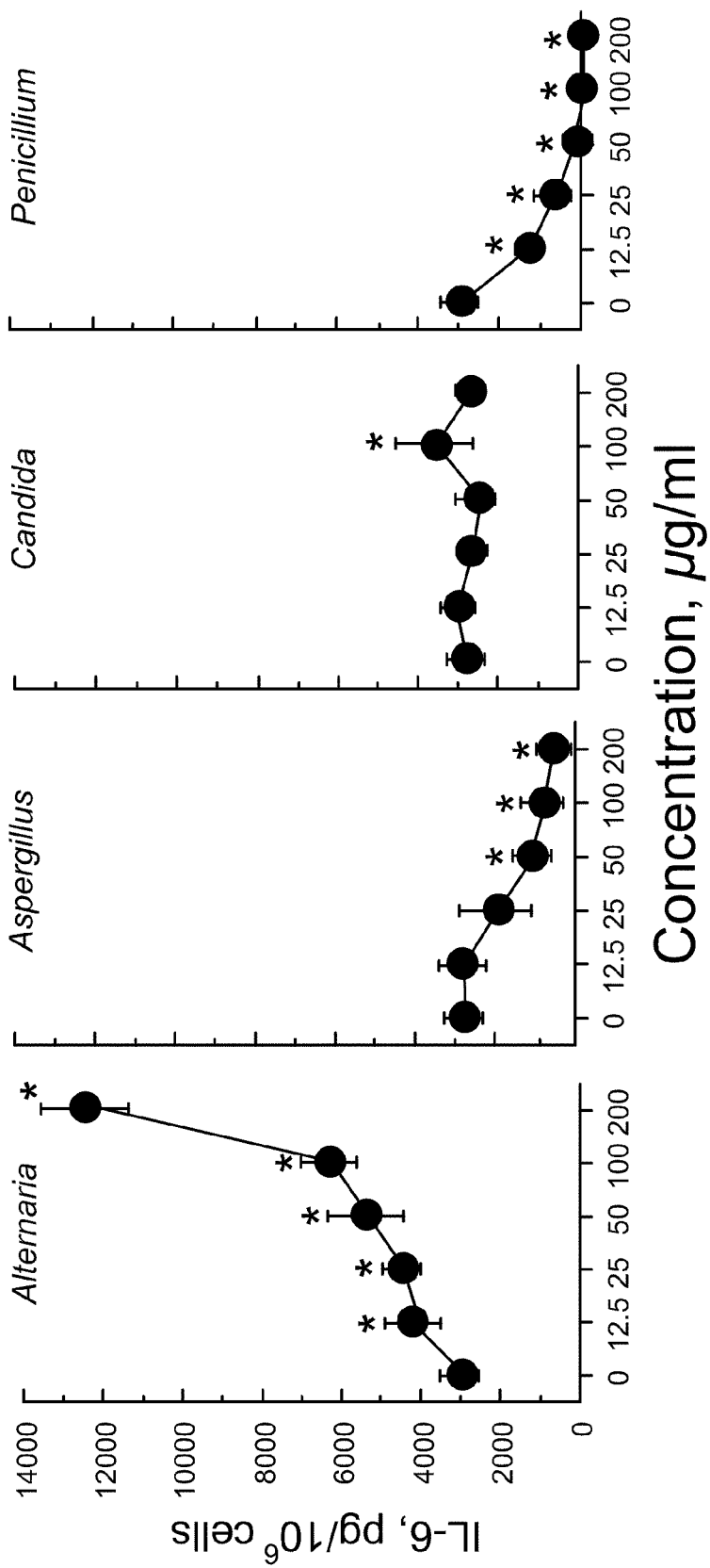
FIG. 10. Effects of fungi on IL-6 production by BEAS-2B cells. BEAS-2B cells were incubated with culture extracts of various fungi for 24 hours. IL-6 concentrations in the supernatants were measured by ELISA. *, p<0.05 compared to medium alone, n=3.
Figure 11:
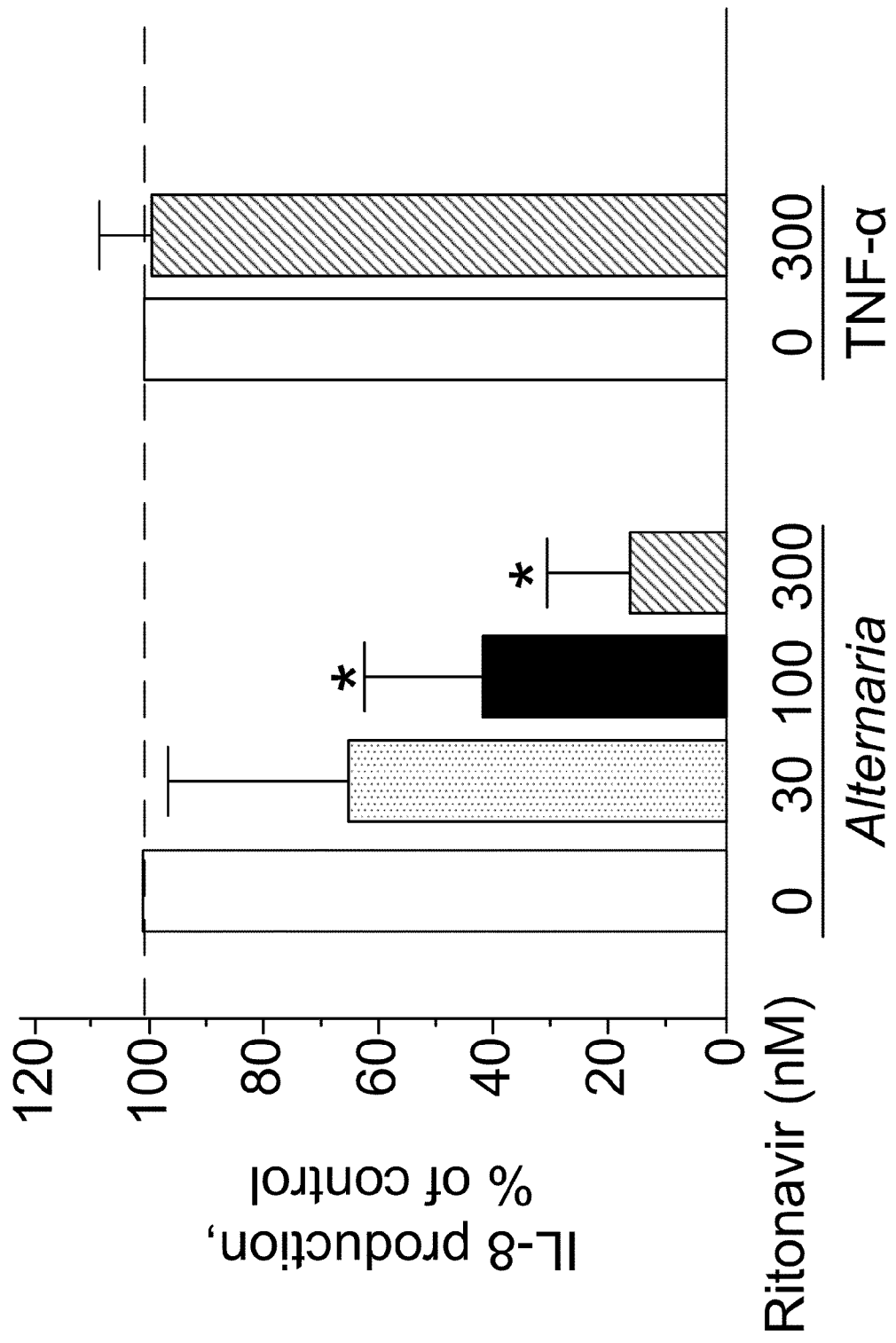
FIG. 11. Effects of an aspartate protease inhibitor, ritonavir, on IL-8 production by BEAS-2B cells. *Alternaria* extract or TNF-α was pretreated with ritonavir and added to BEAS-2B cells. IL-8 concentrations in the supernatants were measured after 24 hours. Data are normalized to the values without ritonavir as 100%. *, p<0.05 compared to no inhibitor, n=4.

Eosinophils may be the only cell that can recognize *Alternaria*. In FIG. 10, an airway epithelial cell line, BEAS-2B, produced and released IL-6 when incubated with *Alternaria* extract for 24 hours. Extracts of *Aspergillus, Candida*, and *Penicillium*, did not induce IL-6 production; rather, both *Aspergillus* and *Penicillium* inhibited the baseline production of IL-6. BEAS-2B stimulated with *Alternaria* also produced other pro-inflammatory factors such as IL-8 and GM-CSF. This *Alternaria*-induced IL-6 production was inhibited by ATBI, nelfinavir, ritonavir or pepstatin A-agarose treatment of *Alternaria* extract by about 60% to 90%; ritonavir results are shown in FIG. 11. In contrast, TNF-α-induced IL-6 production was not affected by these treatments. Furthermore, a peptide antagonist for PAR-2, LSIGKV (SEQ ID NO:35), partially (~40%) but significantly inhibited *Alternaria*-induced IL-6 production by BEAS-2B cells. Thus, through its aspartate protease activity, *Alternaria* may activate airway epithelial cells; this activation is partially mediated by PAR-2.

Figure 12A:
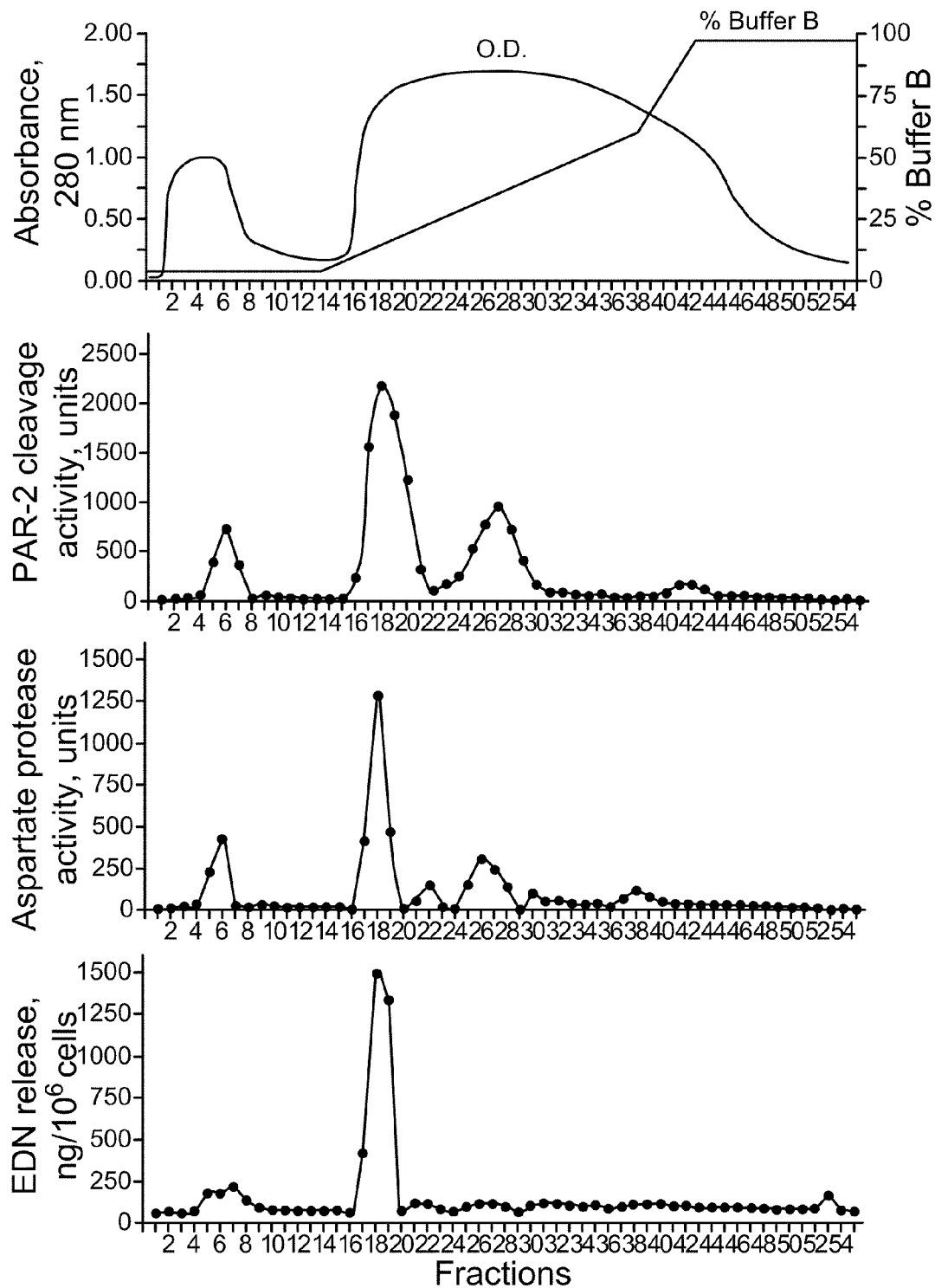
FIG. 12. Panel A. DEAE fractionation of *Alternaria* extract. *Alternaria* extract was separated by DEAE anion-exchange chromatography (Buffer A, 20 mM Tris pH 7.5; Buffer B, 20 mM Tris 1M NaCl pH 7.5) and individual fractions were analyzed for their PAR-2 cleavage activity, aspartate protease activity, and eosinophil degranulation activity. Panel B. A silver-stained SDS-PAGE analysis. Lane 1; crude *Alternaria* extract, Lane 2; DEAE fraction #18 further purified by hydroxyapatite chromatography.
Figure 12B:
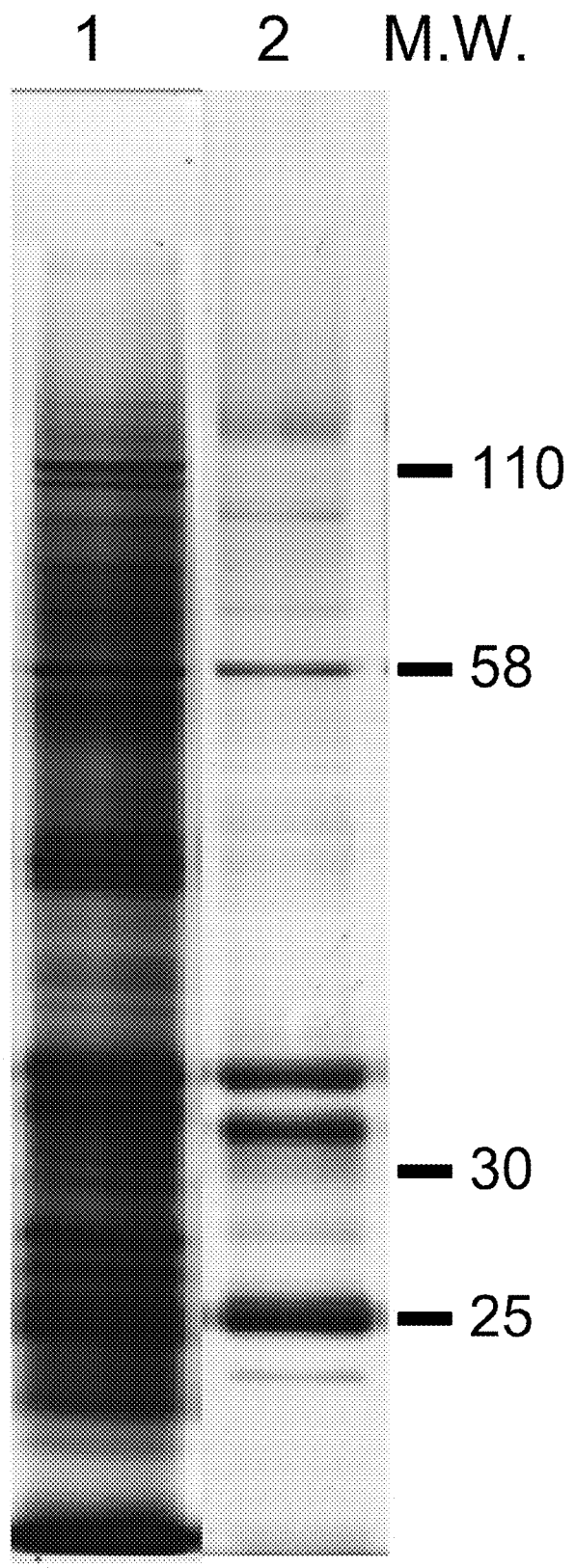

A series of efforts have been initiated to identify and isolate protease(s) from *Alternaria*. A preliminary biochemical characterization showed that, at pH 7.5, the *Alternaria* activity towards eosinophils binds to hydroxyapatite, DEAE Sepharose, and phenyl-Sepharose, but not to a variety of cation exchange or lectin columns. In FIG. 12, DEAE fractionation of an *Alternaria* extract showed a single peak with strong aspartate protease activity, as detected by a malaria aspartate protease substrate. The peak of aspartate protease activity coincided with the peak of the PAR-2 cleavage activity, and the aspartate protease activity paralleled each fraction's ability to induce eosinophil degranulation.

Figure 25A:
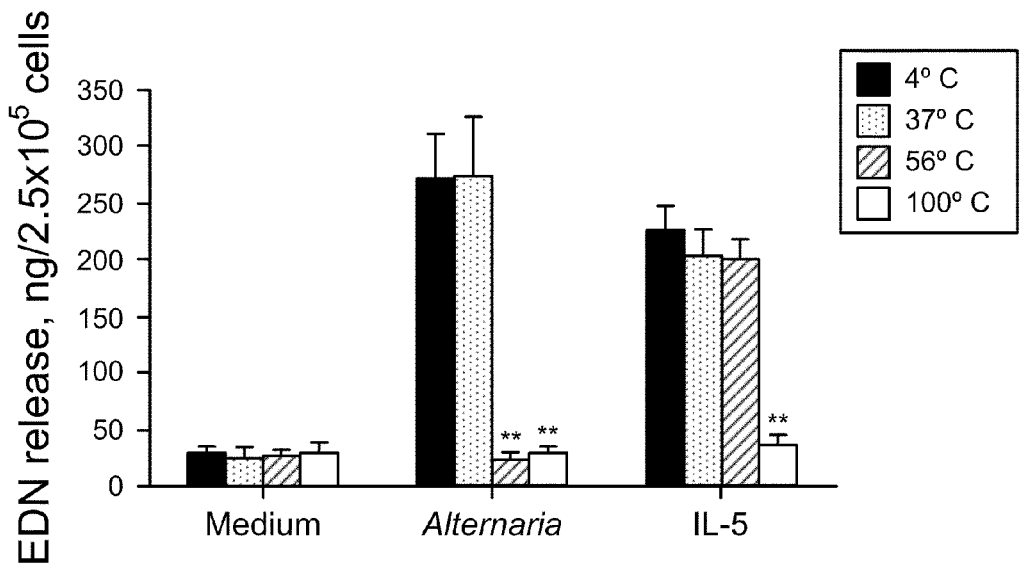
FIG. 25. Partial characterization of *Alternaria* extract. A, Before incubation with eosinophils, aliquots of 100 µg/mL *Alternaria* and 10 ng/mL IL-5 were heated at 37, 56, or 100° C. for 30 min or were treated at 4° C. for 30 min. Eosinophils were incubated in duplicate with these treated stimuli for 3 hours at 37° C. Results show the mean±SEM from five different eosinophil preparations. B, Size exclusion chromatography used a Superdex 200-10/30 column and produced a broad absorbance peak (smooth line) of the *Alternaria* culture extract. The dots connected by lines show the levels of EDN release when portions of fractions 21-39 were incubated with eosinophils. The molecular weight calibration of the column is shown above the elution profile.
Figure 25B:
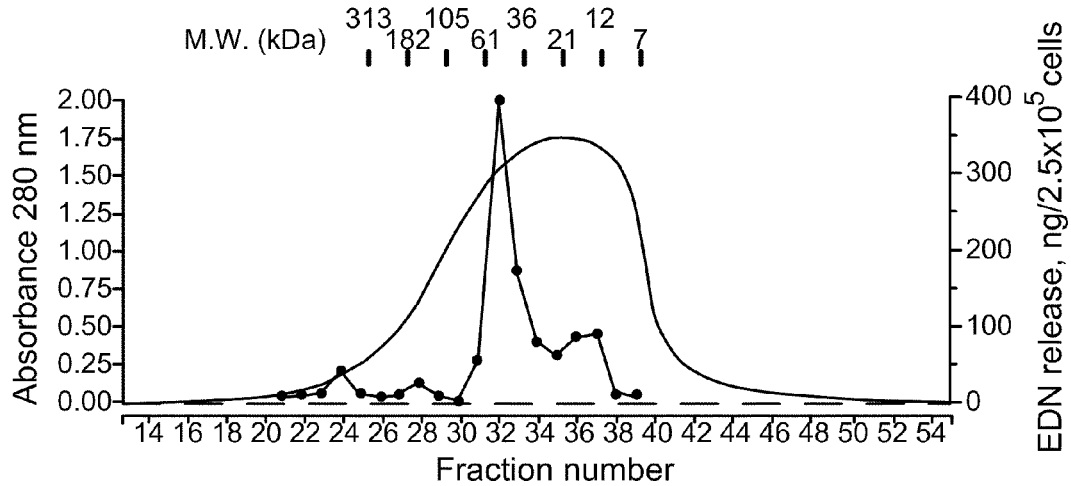
Figure 26:
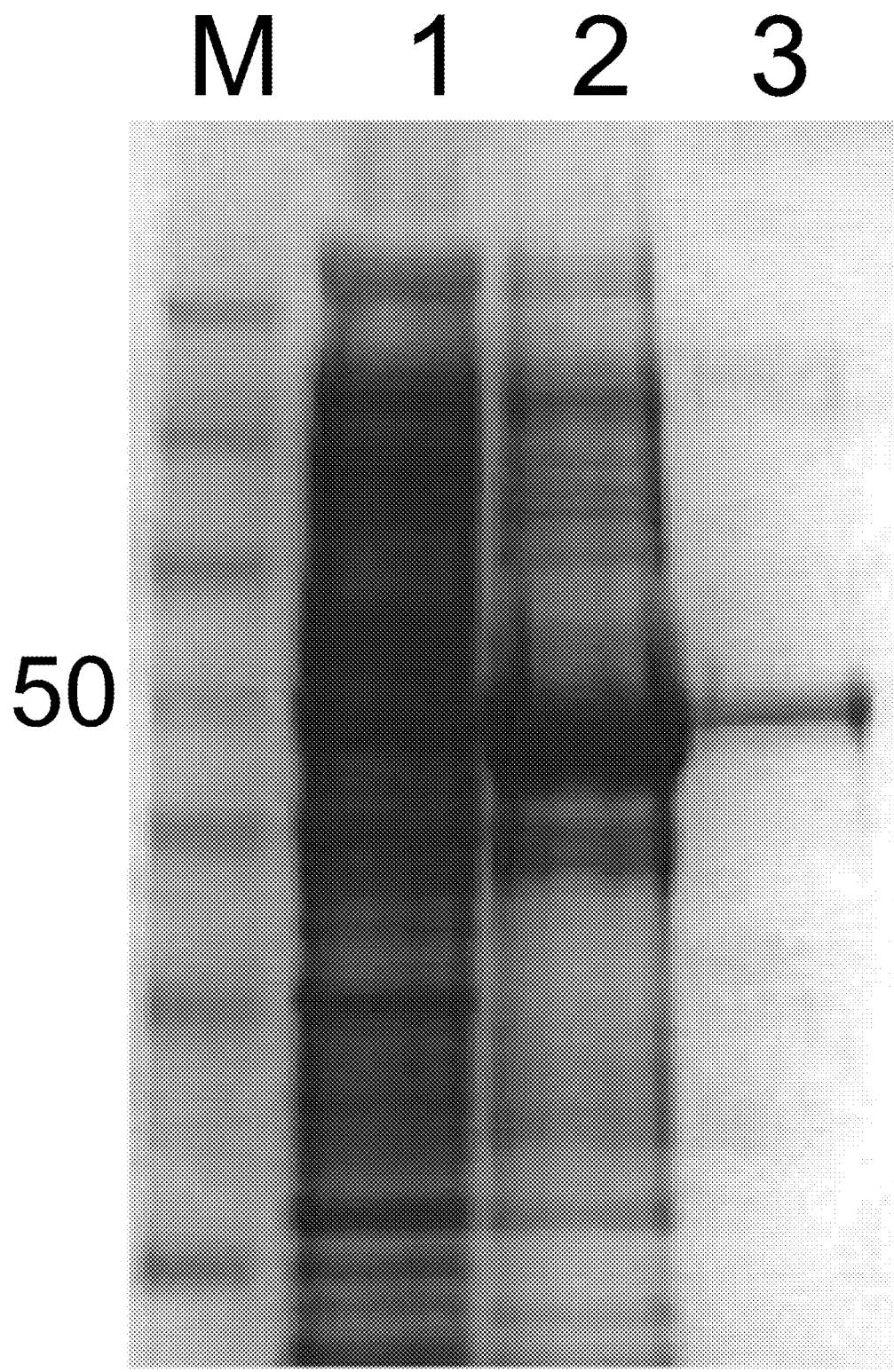
FIG. 26. *A. alternate* xylanase was PCR amplified using genomic DNA as template. PCR product was cloned in pQE-30 UA *E. coli* expression vector. The vector was transformed into the *E. coli* M15 host strain using electroporation and screened for the 6x-His tag. Strong positive colonies were selected and grown in one-liter culture. After induction with IPTG, proteins were purified by a Ni-NTA column. M; marker, 1; protein from uninduced culture, 2; protein from culture induced with IPTG, 3; following purification with Ni-NTA column.

Partial characterization of *Alternaria* extract. Three strategies were used to begin characterizing the *Alternaria* products involved in eosinophil degranulation. First, the *Alternaria* extract was subjected to membrane filtration. After filtration with a YM100 Centricon® membrane, the filtrate stimulated eosinophil degranulation, but the retentate did not. After filtration with a YM10 Centricon® membrane, the retentate stimulated eosinophils, but the filtrate did not. Thus, the eosinophil-stimulatory activity in the *Alternaria* extract is likely between 10 and 100 kDa. Second, *Alternaria* extracts, which had been treated at 56° C. or 100° C. for 30 min, did not induce EDN release (FIG. 25A), but extracts treated at 4° C. or 37° C. for 30 min did induce EDN release, suggesting that it is a heat-labile protein(s) or glycoprotein(s). The activity of a cytokine, IL-5, to induce EDN release was abolished by treatment at 100° C., but not by treatment at 56° C. or lower temperatures. Third, size exclusion chromatography was used (FIG. 25B), and the column fractions tested for their abilities to induce eosinophil degranulation. Although the absorbance profile shows a broad peak from fractions 32 though 37, the most potent eosinophil degranulation activity appeared in fraction 32 with a molecular mass about 60 kDa.

Figure 44:
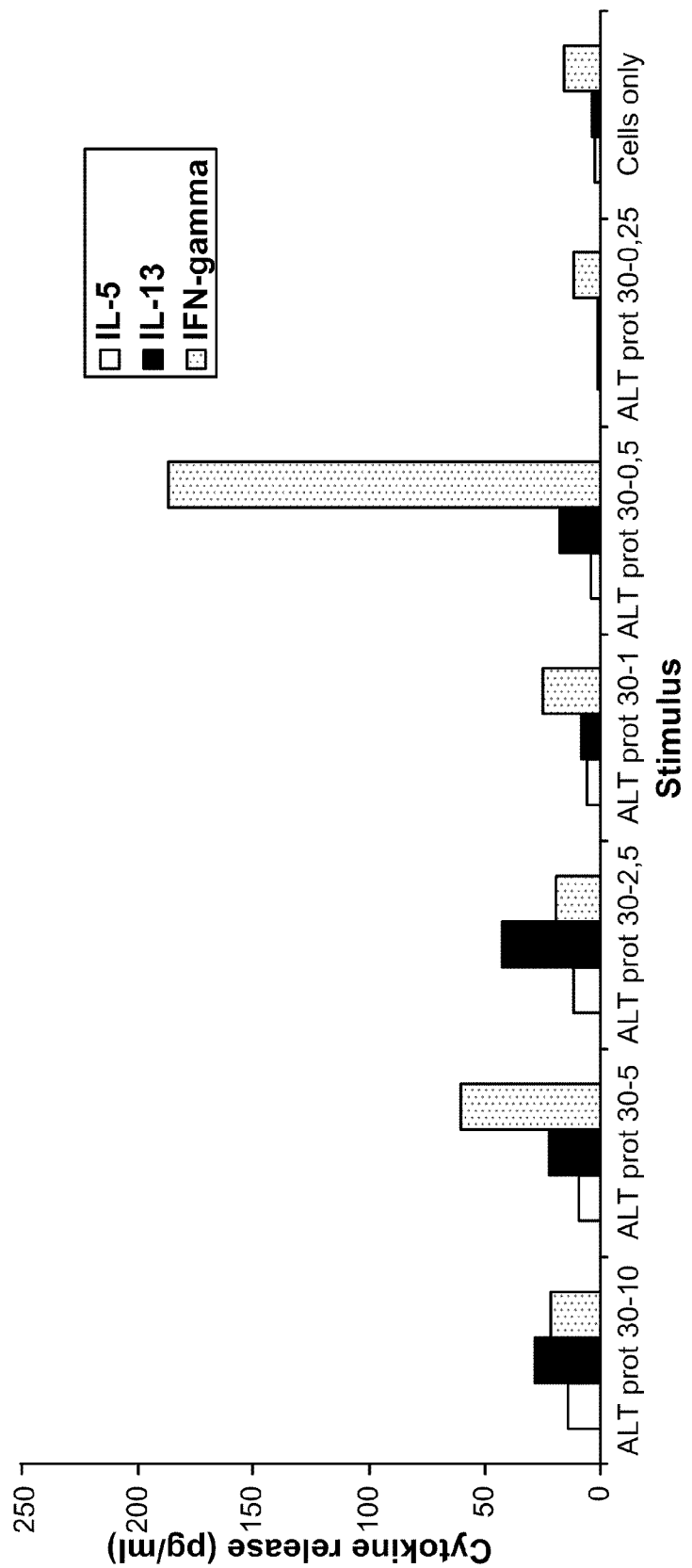
FIG. 44. PBMC after challenge with isolated *Alternaria* protein fractions 30.
Figure 45:
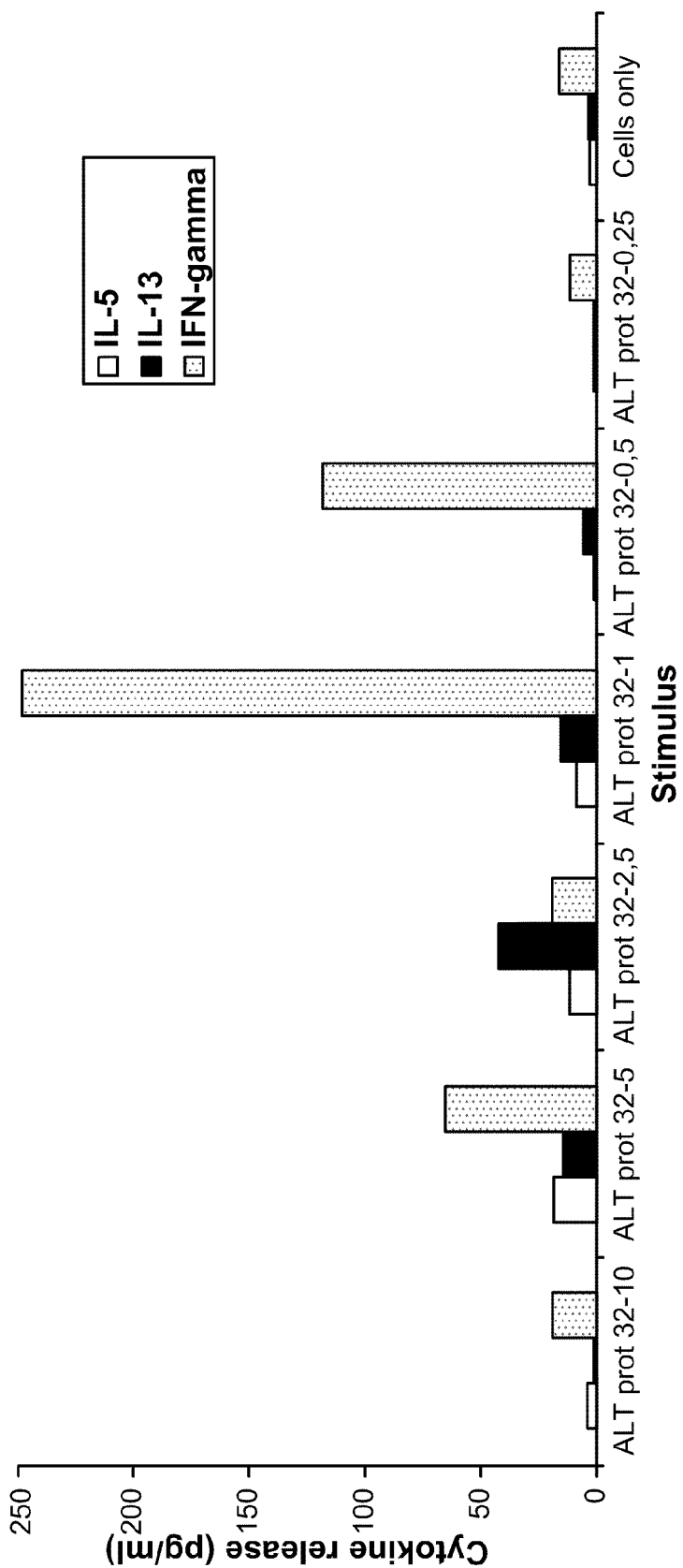
FIG. 45. PBMC after challenge with isolated *Alternaria* protein fractions 32.

PBMCs obtained from a CRS patient were incubated with fractions 30 or 32, and the level of cytokine production was measured (FIGS. 44 and 45).

Polypeptides (e.g., enzymes) implicated in the activation of eosinophils and promotion of eosinophillic inflammation in a murine model were identified. Proteins in HPLC DEAE fraction #18 and the eluate from pepstatin A agarose were trypsin digested, and the resulting peptides were subjected to nLC-microESI-MS/MS analysis using a Finnigan LTQ system (Thermo Electron Corporation, Waltham, Mass.). Peptide mass fingerprinting with SEQUEST software (distributed by Thermo Electron Corporation, Waltham, Mass.) was used to identify peptides existing in these fractions using the resulting peptide mass data and a database of predicted *Alternaria brassicicola* proteins derived from expressed sequence tags (ESTs) and the *A. brassicola* whole genome shotgun sequence information. SEQUEST correlates uninterpreted tandem mass spectra of peptides with amino acid sequences from protein and nucleotide databases. SEQUEST will determine the amino acid sequence of the peptide fragments, and thus the full length protein(s) can be identified. Proteins in the database were predicted using ab initio gene finding and protein prediction software FgeneSH (Softberry, Inc., Mount Kisco, N.Y.). SEQUEST is a registered trademark of the University of Washington. SEQUEST uses algorithms described in U.S. Pat. Nos. 6,017,693 and 5,538,897.

The fungal genes encoding these immunostimulatory proteins were identified using the above described approach. The implicated immunostimulatory proteins identified in these fractions were then further annotated by BlastP analysis against the GenbankNR database and the MEROPS peptidase database. The MEROPS database is an information resource for peptidases (also termed proteases, proteinases and proteolytic enzymes) and the proteins that inhibit them and was developed and web accessible at the Sanger Institute, UK. Furthermore, all candidate proteins were subjected to Interpro analysis. InterPro is a database of protein families, domains and functional sites in which identifiable features found in known proteins can be applied to unknown protein sequences. Interpro analysis is web accessible and a public service available at the European Bioinformatics Institute (EMBL-EBI). The annotated proteins include several proteases belonging to S53 and M38 families, several predicted glycolytic enzymes, superoxide dismutase, a ribosomal protein, S-adenosyl-homocysteine lyase, and several others (Table 1).

TABLE 1

Identified polypeptides.

| SEQ ID NO: | Functional Annotation |
|---|---|
| 2 | *Alternaria alternata* endoxylanase - gi\|6179886\|gb\|AF176570.1\|AF176570 |
| 4 | S-adenosyl-L-homocysteine hydrolase |
| 6 | glycosyl hydrolase family 61 (Endo-1,4-beta-glucanase IV/Cellulase IV) |
| 8 | glycosyl hydrolase family 31, alpha-glucosidase |
| 10 | peptidase family S53 contains acid-acting endopeptidases |
| 12 | peptidase family S53 contains acid-acting endopeptidases |
| 14 | contains predicted signal peptide for secretion |
| 16 | *A. alternata* 60S acidic ribosomal protein P1 (Allergen Alt a12) P49148 GI:1350779 |
| 18 | Superoxide dismutase |
| 20 | contains predicted transmembrane regions |
| 22 | Peptidase family M38 (beta-aspartyl dipeptidase family) |
| 24 | contains predicted signal peptide and transmembrane domains |
| 26 | Unknown |
| 28 | Arginase |
| 30 | glyosyl hydrolase family 7 Exoglucanase 1 precursor (Exoglucanase I) (Exocellobiohydrolase I) (1,4-beta-cellobiohydrolase I) (Beta-glucancellobiohydrolase I) |
| 32 | glycosyl hydrolase family 6 - cellobiohydrolase II |
| 34 | cellobiose dehydrogenase |

The *Alternaria brassicicola* nucleic acid sequence for each identified *Alternaria alternata* candidate along with the predicted *Alternaria brassicicola* amino acid sequence is set forth in FIGS. 27-39.

Example 5

Production of Immunostimulatory Molecules by Live *Alternaria*

Figure 13A:
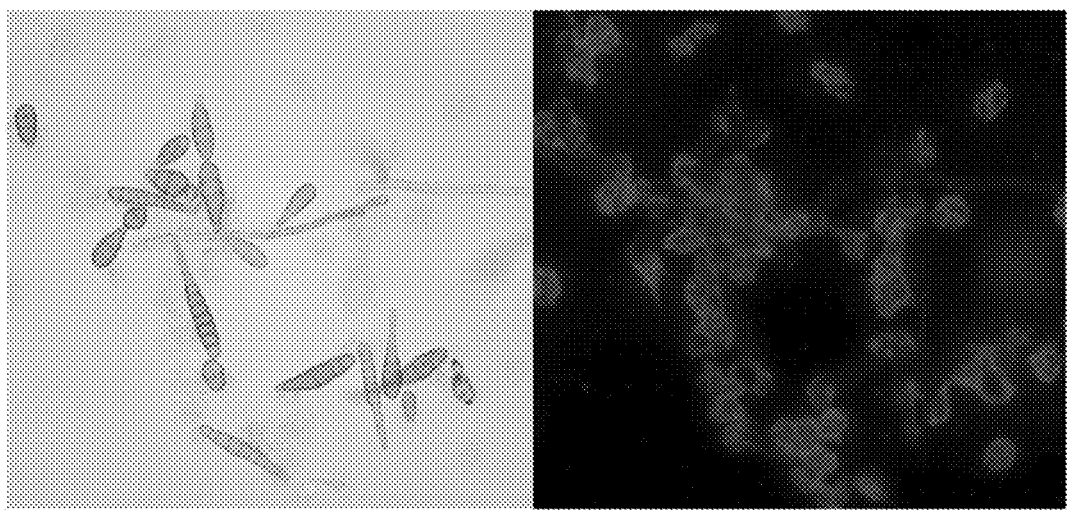
FIG. 13. Morphology of eosinophils incubated with germinating *A. alternata* (Panel A) and release of EDN by these eosinophils (Panel B). Spores of *A. alternata* were cultured in RPMI medium with 10% FCS for 12 hours. Freshly isolated eosinophils were added to the wells at indicated eosinophil: spore ratios and incubated for an additional 4 hours. Concentrations of EDN released into the supernatants were measured by ELISA. Data are presented as mean±range from a duplicate experiment. Left panel and right panel in Panel A shows bright field image and anti-MBP immunofluorescence staining (to visualize eosinophils), respectively.
Figure 13B:
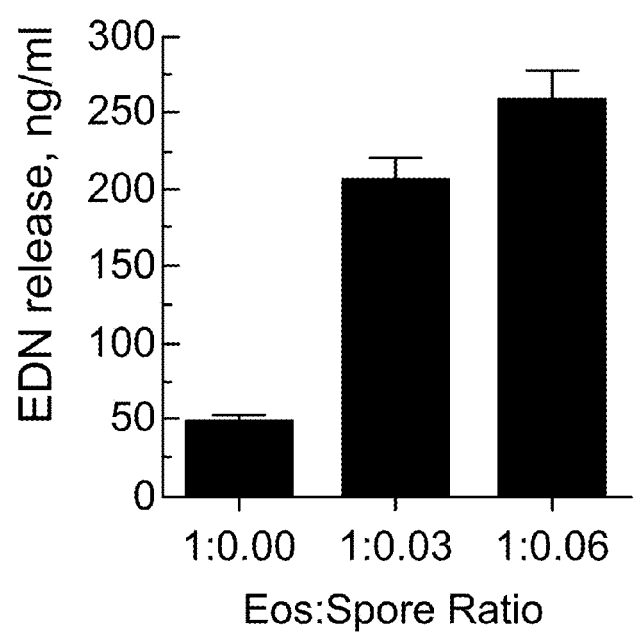
Figure 14:
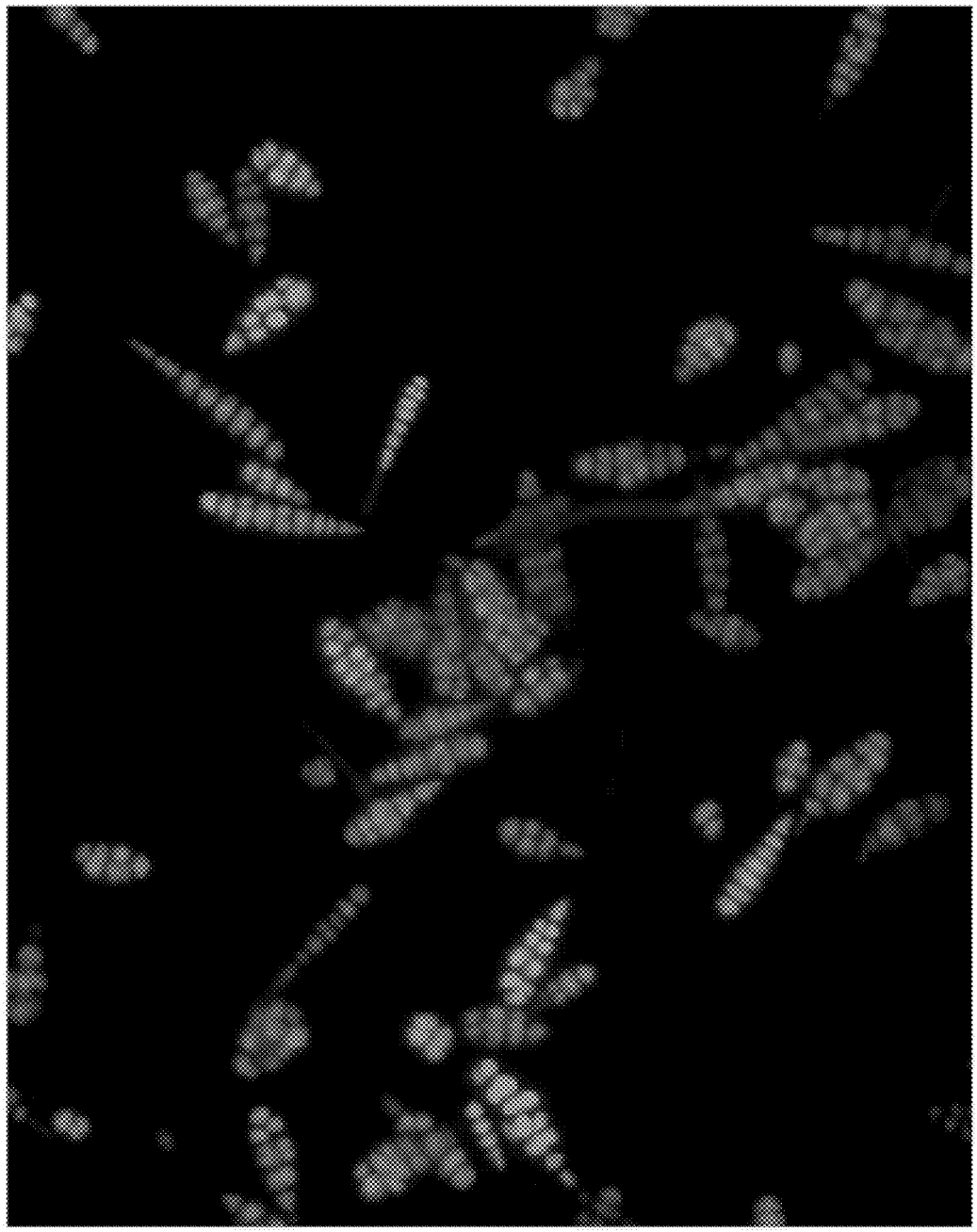
FIG. 14. Morphology of spores from GFP-transformed *A. alternata*.
Figure 15B:
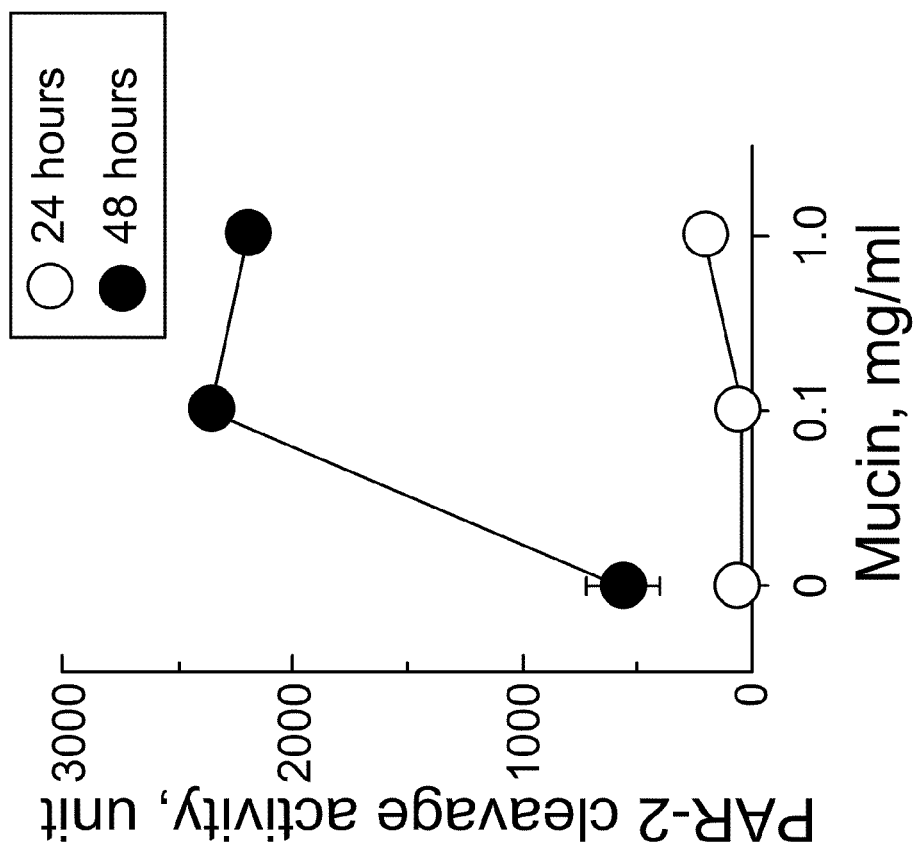
FIG. 15. Growth of *A. alternata* and production of PAR-2 activating enzyme(s). Spores of GFP-transformed *A. alternata* (1,000 spore/well of 96-well tissue culture plates) were cultured in HBSS medium supplemented with different concentrations of bovine mucin from submaxillary glands. Fungal growth was quantitated after 48 hours by measuring the intensity of GFP fluorescence in each well (Panel A). Production of PAR-2 activating proteases by fungi into the supernatants was measured at 24 hours or 48 hours by using a fluorescence quenched PAR-2 peptide substrate (Abz-SKGRSLIGK(Dnp)D) (Panel B) (SEQ ID NO:37). Data are presented as mean±SEM from a triplicate experiment.
Figure 15A:
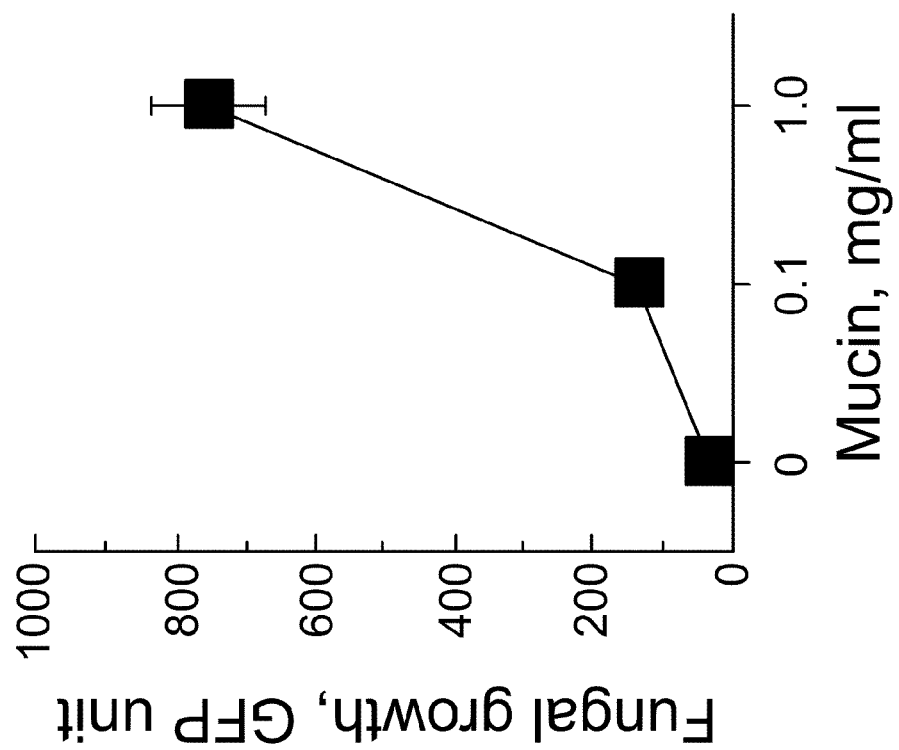

Spores of *A. alternata* were obtained, and the effects of the fungus itself on eosinophil activation were examined. Various numbers of spores were suspended in RPMI medium with 10% FCS and incubated in tissue culture wells for 12 hours to induce germination. A fixed number of isolated human eosinophils were added to the wells and incubated for an additional 4 hours. These eosinophils showed strong conjugate formation with the germinating *Alternaria* fungal spores (FIG. 13A). Furthermore, these eosinophils became activated and released their granule proteins into the supernatants (FIG. 13B). To characterize the growth pattern and production of immunostimulatory molecules by *Alternaria* further, GFP-transformed *A. alternata* were used (FIG. 14). Currently, there is no standardized scientific method to quantitate fungal growth. However, these transformed fungi have a technical advantage; fungal growth can be quantitated by measuring the fluorescence intensity using a plate reader or spectrophotometer. Production of so-called "allergens" by fungi can be significantly increased during and after their germination. FIG. 15B shows that the PAR-2-stimulating enzymatic activity(ies) is clearly produced by *A. alternata* during their germination and hyphal growth. The growth of fungi (FIG. 15A) and production of PAR-2 activating enzymes (FIG. 15B) dramatically increased when fungi were incubated in the presence of airway mucin. Thus, *A. alternata* likely produces PAR-activating enzyme(s) during their germination and growth, in particular when they germinate on mucosal surfaces, and eosinophils demonstrate a vigorous inflammatory response against these germinating fungi. The model of a spore/eosinophil mixed culture provides a tool to dissect the role of specific *Alternaria* molecule(s) in the eosinophil's recognition of and response to this fungus.

The polypeptide having the amino acid sequence set forth in SEQ ID NO:2 was recombinantly produced in *E. coli* and tested for the ability to stimulate eosinophil degranulation. This polypeptide stimulated eosinophil degranulation, as measured by EDN release, in a concentration-dependent manner.

Example 6

In Vivo Mouse Model of Immune Response to *Alternaria*

In FIG. 1, PBMC from CRS patients show increased cellular and humoral immune responses to *Alternaria*. To dissect the role of immune cells in their responses to fungi, a mouse model was developed. Because CRS patients showed an increased immune response to fungi, BALB/c mice were sensitized to *Alternaria* by intraperitoneal (i.p) injection of *Alternaria* extract (Greer Laboratories) and subsequently challenged mice intranasally (i.n.) with the same extract. Mice sensitized and challenged with *Alternaria* exhibited striking airway eosinophilia. Airway eosinophilia was also observed in mice sensitized with PBS (no antigen) and challenged intranasally with *Alternaria*. Thus, mice might have an innate ability to produce an airway eosinophilic response to certain fungi, which may be similar to the innate Th2 and eosinophilic responses to helminth parasites in mice.

To test this hypothesis, fungal extracts or OVA (as a control) were administered intranasally to naive mice without prior sensitization on days 0, 3, and 6, and airway inflammation was analyzed on day 8. Mice exposed to culture supernatant or cellular extract of *Alternaria* exhibited significant airway eosinophilia (FIG. 16). *Aspergillus* induced mild airway eosinophilia. In contrast, *Candida* induced neutrophilia, but no eosinophilia. This airway eosinophilia in *Alternaria*-exposed mice is probably not due to accidental prior sensitization of the animals to *Alternaria* for the following reasons: 1) mice from different animal vendors showed similar eosinophilic responses; 2) no IgG or IgE antibodies to *Alternaria* were detected in naive mouse serum; and 3) spleen cells from naive mice cultured with *Alternaria* antigen did not produce IL-4 or IL-5. In addition, the airway eosinophilic response to *Alternaria* was reproducible among different strains of mice including BALB/c, C57BL/6, C3H/HeJ, C3H/HeSnJ, and WBB6F1/J-KitW/KitW-v.

Figure 17B:
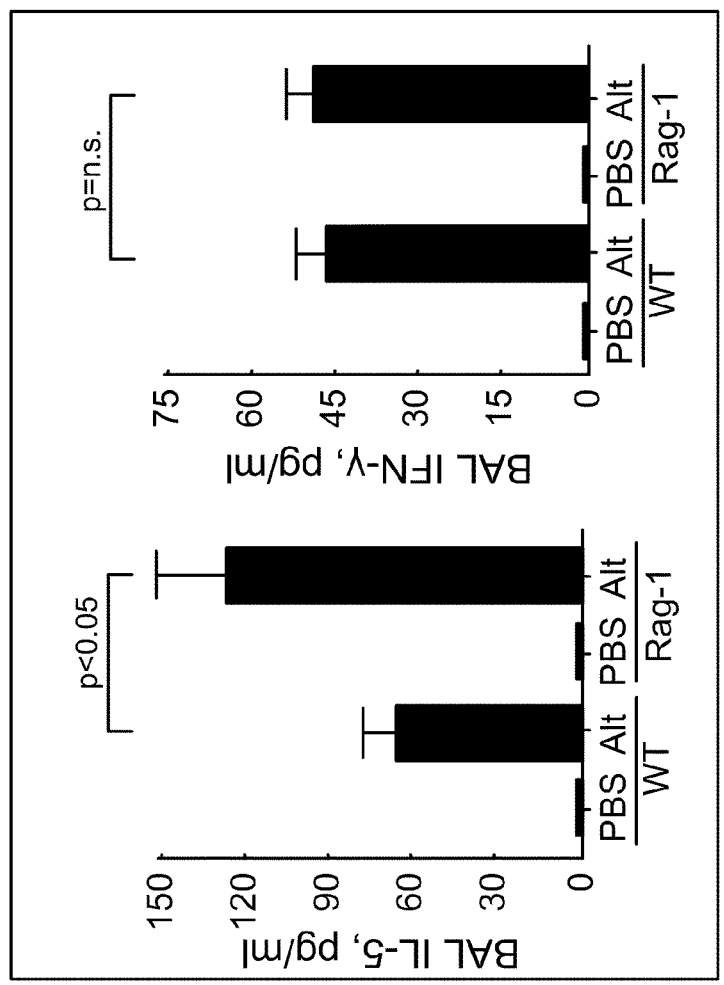
FIG. 17. Effects of immune cell deficiency on *Alternaria*-induced airway eosinophilia and early cytokine response. Naive Rag-1 knockout (Rag-1) or wild type (WT) mice were exposed to *Alternaria* (Alt) intranasally on days 0, 3, and 6. Panel A shows kinetics of airway eosinophilia. Panel B shows early cytokine response 12 hours after the first exposure (i.e. day 0.5), n=4-9.
Figure 17A:
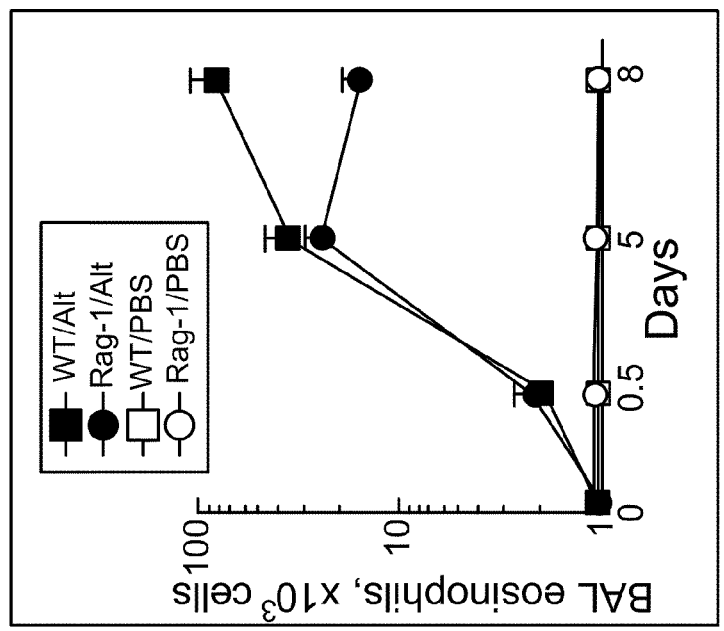

Generally, an intact adaptive immune system, especially the Th2 cells, is needed to develop robust airway eosinophilia in mice sensitized and challenged with OVA as described elsewhere. The contributions of the adaptive immune system in the development of airway eosinophilia in naive *Alternaria*-exposed mice were investigated. In FIG. 17A, there were no differences in the early eosinophilia (i.e., days 0.5 and 5) between wild-type animals and Rag-1−/− mice, suggesting that an innate immune response mediated the early eosinophilic response to *Alternaria*. In contrast, an adaptive immune system, presumably T cells, was required for further development of eosinophilia at a later time point (i.e., day 8). When *Alternaria* was administered only once to the mouse airways, IL-5 and IFN-γ, but not IL-4, were detected in BAL fluids by as early as 3 hours and peaked at 12 hours, suggesting that the early cytokine production does not reflect a typical Th2 pattern. Furthermore, the early IL-5 and IFN-γ responses (12 hours after first exposure) were not reduced in Rag-1−/− mice (FIG. 17B). Rather, IL-5 production was enhanced in Rag-1−/− mice, suggesting that innate immune cells are responsible for this early production of IL-5 and IFN-γ and that adaptive immune cells may show inhibitory effects on this innate response.

Figure 16:
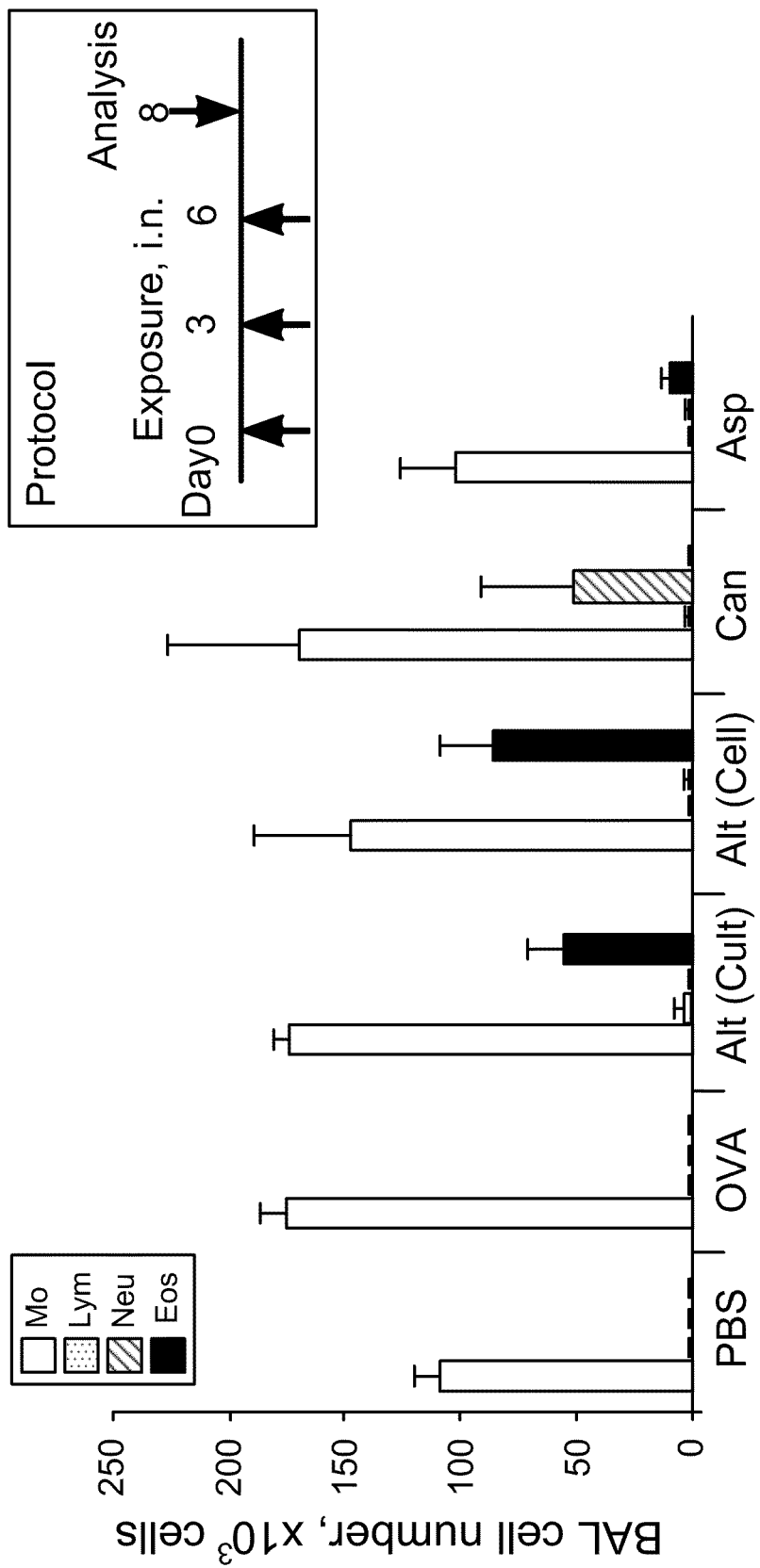
FIG. 16. Effects of intranasal exposure to fungal antigens or OVA on airway inflammation. Naive mice were exposed intranasally to antigens (250 μg/exposure) without prior sensitization. Alt (cult), *Alternaria* culture supernatant; Alt (cell), *Alternaria* cellular extract; Can, *Candida* extract; Asp, *Aspergillus* extract.
Figure 18B:
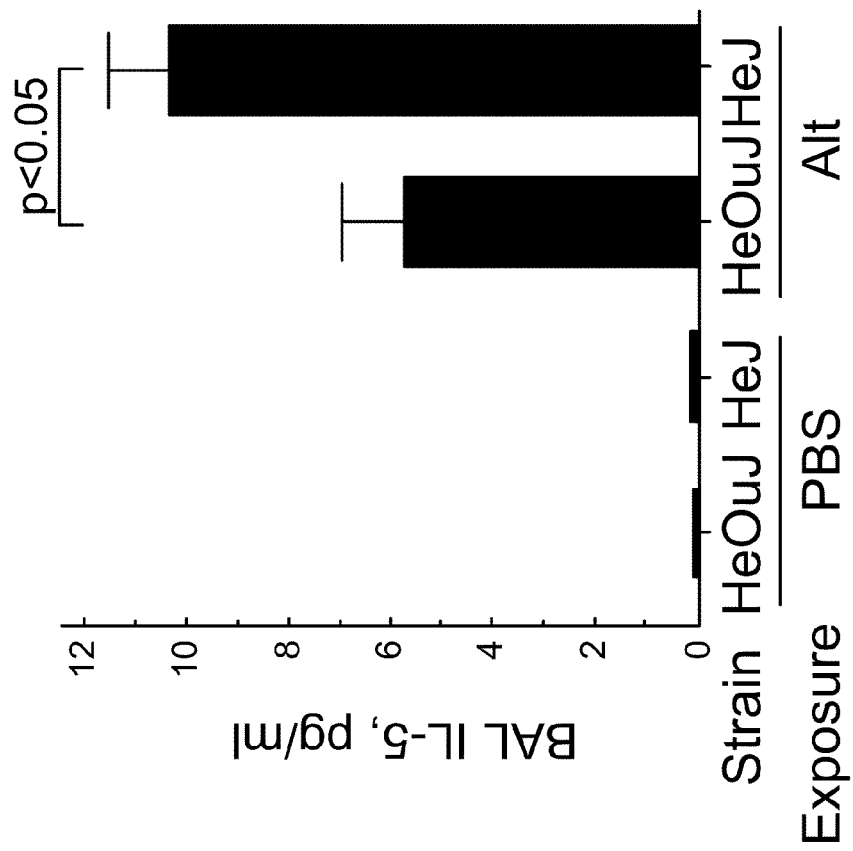
FIG. 18. Early airway IL-5 production in response to *Alternaria* exposure. Panel A: BALB/c mice were pretreated by intranasal administration of LPS (1 μg) or PBS on day −3, and then exposed to *Alternaria* (Alt) on day 0. BAL fluids were collected 12 hours later. Panel B: C3H/HeOuJ or C3H/HeJ mice were exposed to *Alternaria* or PBS on day 0 without prior treatment. BAL fluids were collected 12 hours later. n=5-6.
Figure 18A:
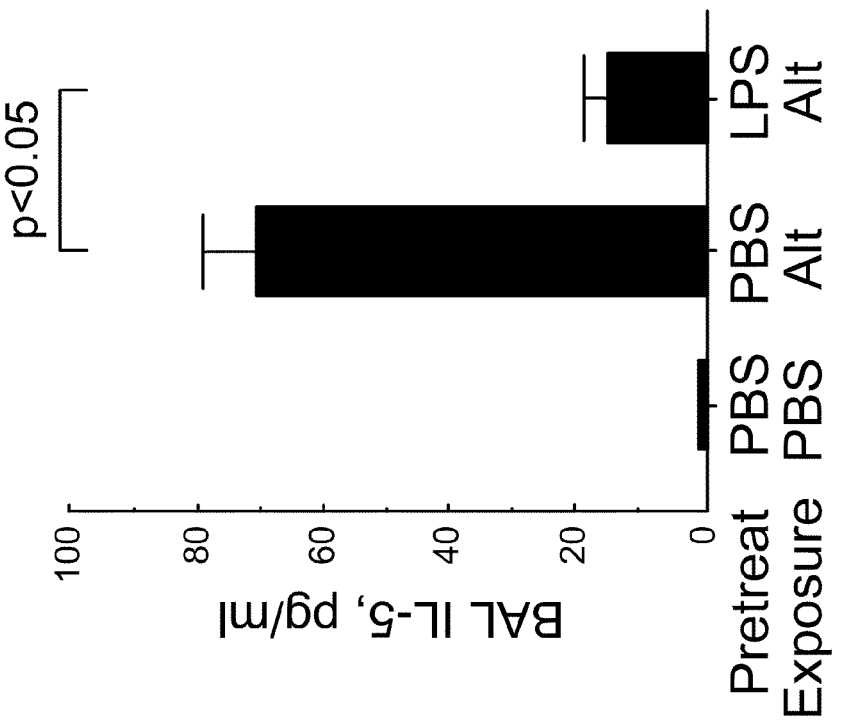

Various molecules and their receptors can be involved in this Th2-like airway inflammation in naive mice exposed to *Alternaria* in vivo (FIG. 16). In mice, a small amount of LPS interacting with TLR4 is a factor in promoting Th2 sensitization to protein antigens as described elsewhere. In addition, the cysteine proteinase gene from *Leishmania mexicana* has been implicated in the upregulation of Th2 immunity and the downregulation of Th1 immunity to this pathogen in mice. The *Alternaria* preparation contained a minimal amount of LPS (0.4 ng/mg dry weight); thus, each mouse received 0.1 ng of LPS/challenge. Because this amount of LPS is much smaller than that used previously to promote an airway Th2 response to OVA (i.e., 100 ng/challenge, 74), it is very unlikely that LPS contributes to this model. Also, prior treatment of mouse airways with 1 μg LPS significantly inhibited this early IL-5 production (FIG. 18A). This early IL-5 production was significantly enhanced in mice deficient in TLR-4 (C3H/HeJ) compared to control mice (C3H/HeOuJ) (FIG. 18B). Early IL-5 production was also increased in IL-10 deficient mice compared to wild-type controls (19.1±8.0 vs 7.6±2.8, n=4), suggesting a role for IL-10 to down-regulate the early IL-5 response. Altogether, naïve mice likely show innate IL-5 and eosinophilic responses to airway exposure of *Alternaria*, and this innate response may be down-regulated by activation of TLR-4 or by production of IL-10.

Figure 19B:
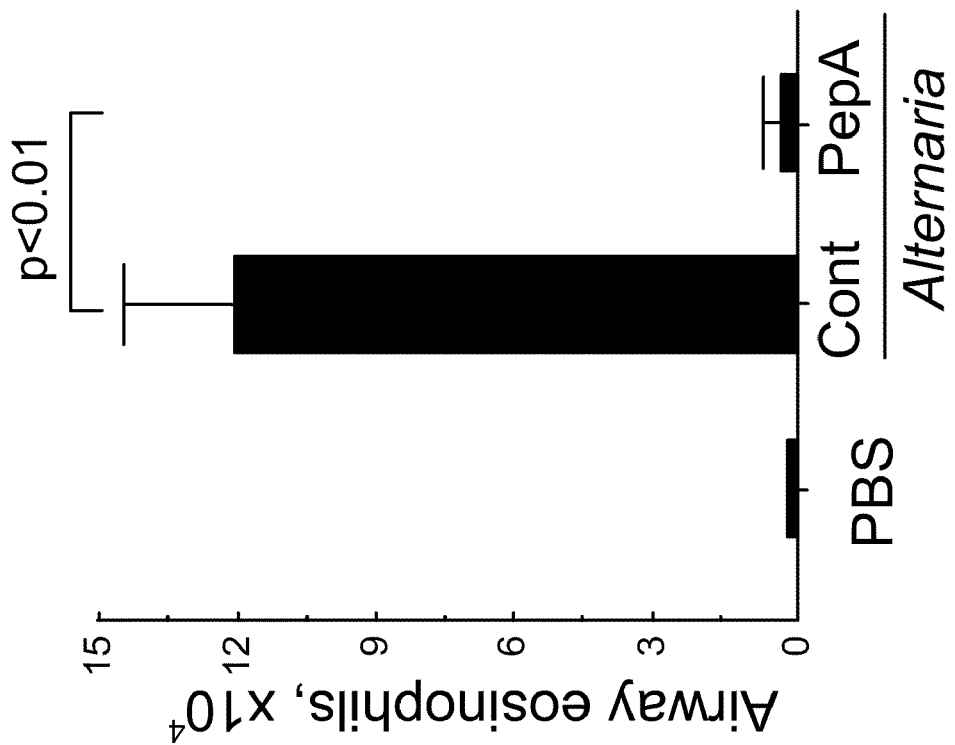
FIG. 19. *Alternaria* extract was pretreated with pepstain A-agarose (Pep A) or control agarose (Cont). Panel A: Mice were intranasally challenged with treated *Alternaria* extract on day 0, and BAL fluids were analyzed for IL-5 after 12 hours. Panel B: Mice were intranasally challenged with treated *Alternaria* extract or PBS on days 0, 3, and 6, and BAL fluids were analyzed for eosinophil numbers on day 8. n=4-7.
Figure 19A:
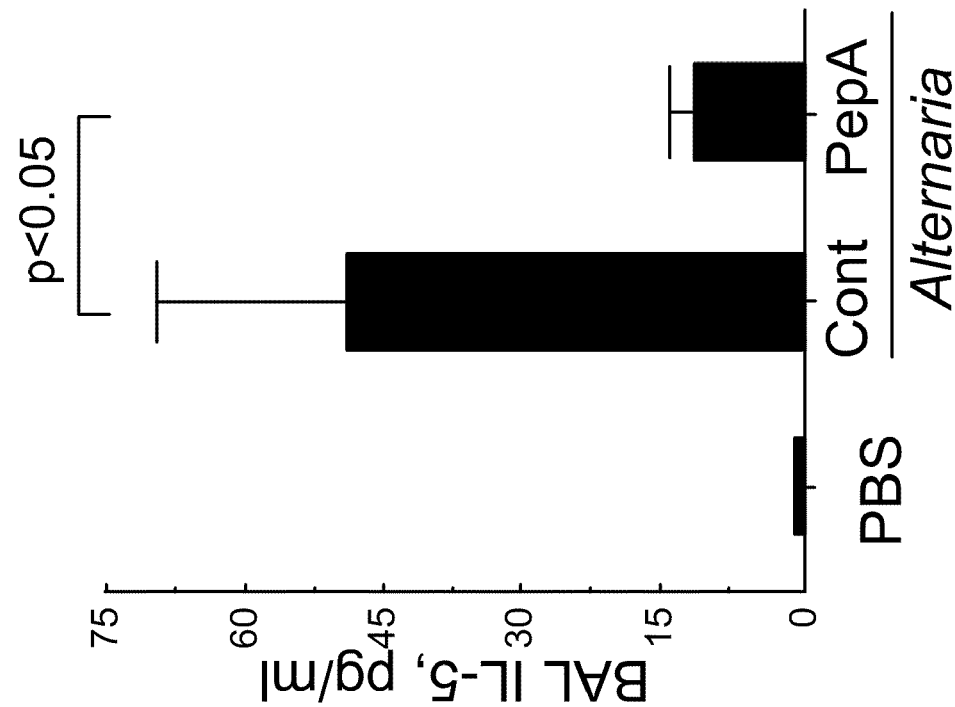
Figure 20:
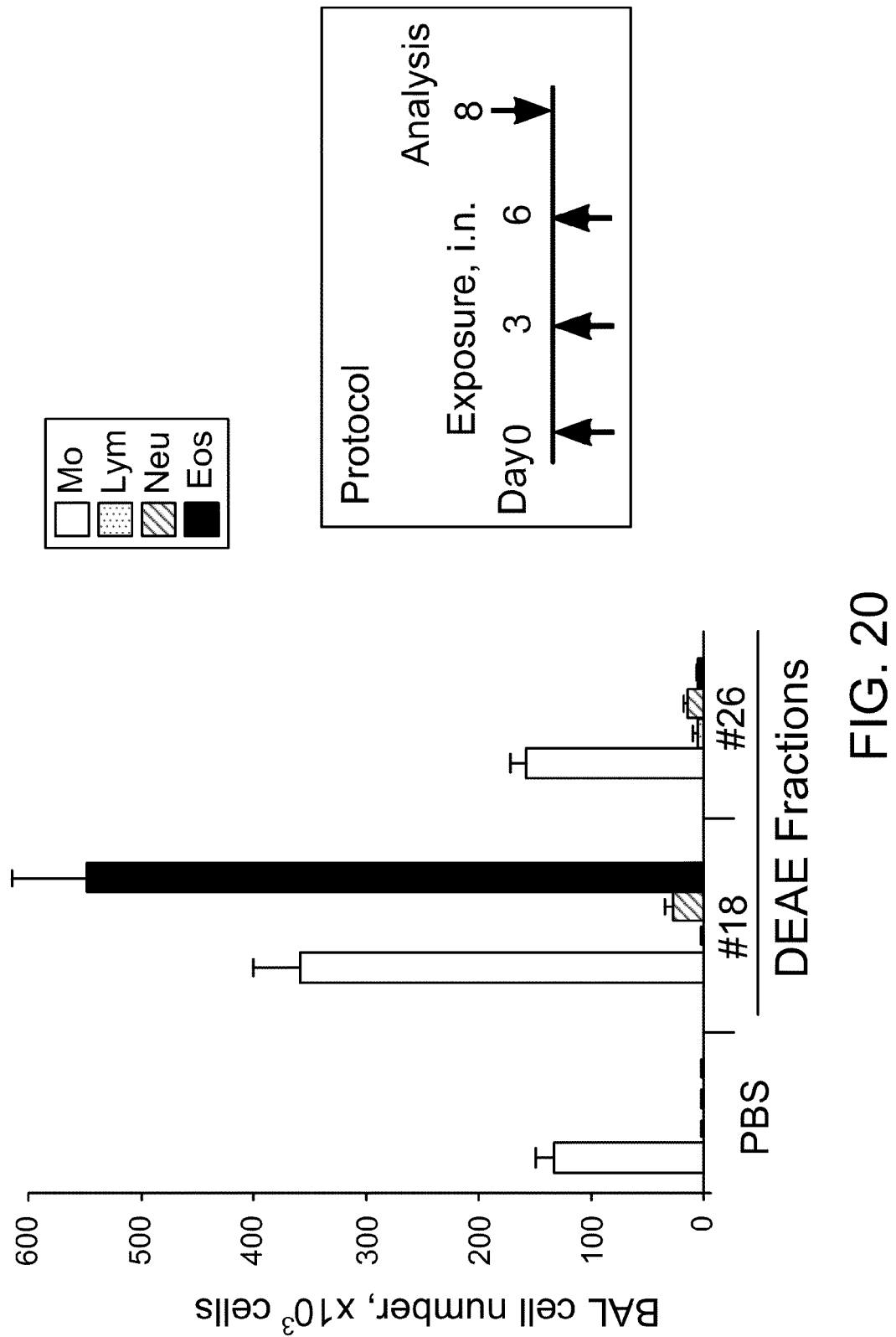
FIG. 20. Effects of *Alternaria* DEAE fractions on airway inflammation. Naive mice were exposed intranasally to PBS or DEAE fractions of *Alternaria* extract without prior sensitization. The fractions used are those described in FIG. 12. n=3.

The in vitro experiments suggested a potential role for *Alternaria* aspartate protease(s) in the activation of eosinophils (FIG. 9) and airway epithelial cells (FIG. 11). Thus, it is hypothesized that the protease(s) similar to those involved in eosinophil degranulation and airway epithelial cell production of IL-8 in vitro may be involved in the development of airway eosinophilia in vivo in mice. To address this question in vivo, *Alternaria* extract was treated with pepstatin A-agarose to remove aspartate protease(s) or control agarose (FIG. 9) and was administered to naïve mice. Pepstatin A treatment significantly inhibited both early production of IL-5 at 12 hours and airway eosinophilia on day 8 (FIG. 19). FIG. 20 shows that the same peak fraction from the DEAE fractionation (i.e., Fraction #18 of FIG. 12), which contained strong aspartate protease activity and potently induced eosinophil degranulation, also induced marked airway eosinophilia when administered into naïve mice.

Example 7

Figures 21A, 21B:
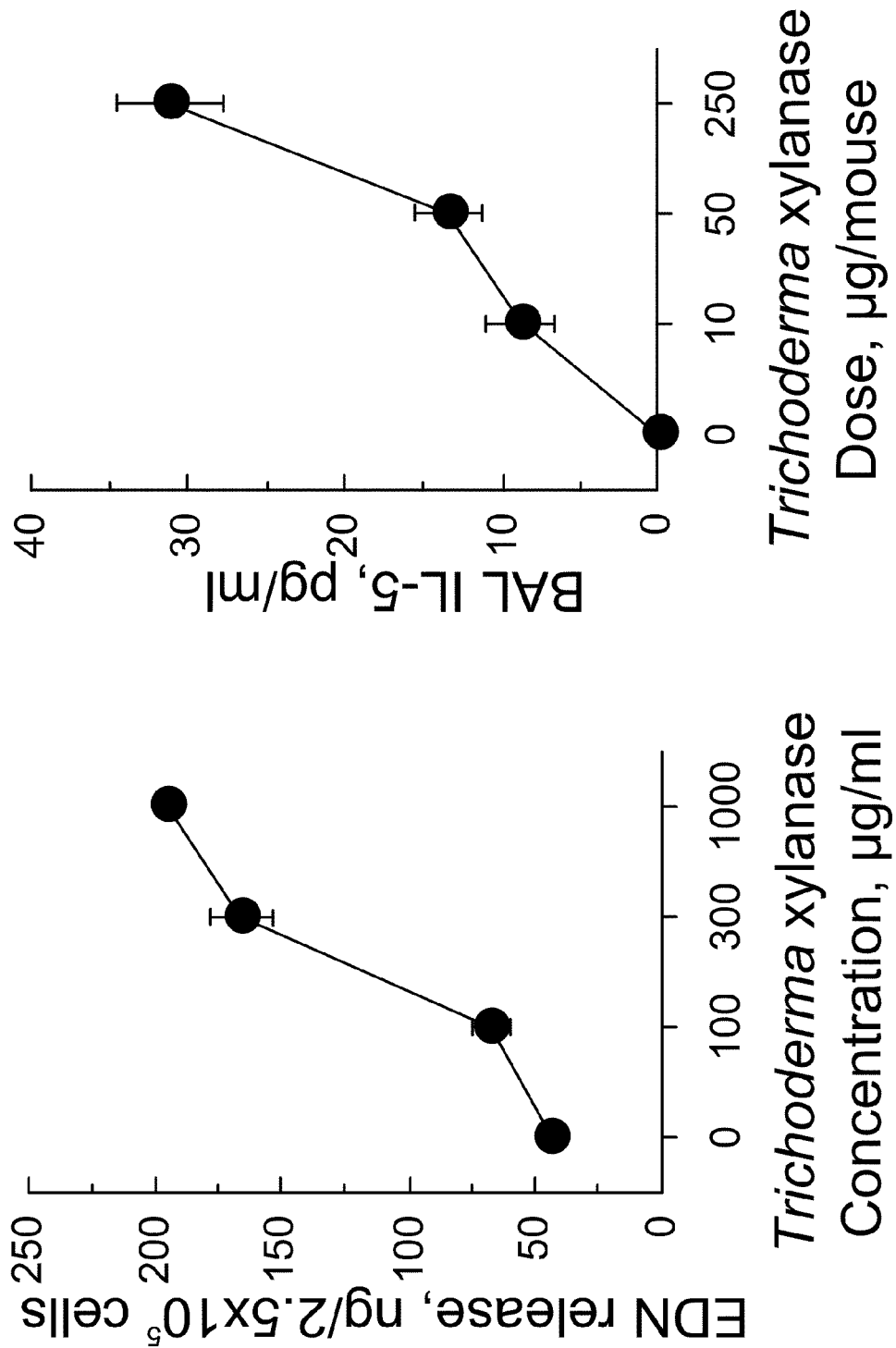
FIG. 21. Effects of *Trichoderma* xylanase on eosinophil degranulation (Panel A). Effects of *Trichoderma* xylanase on IL-5 production in mouse airways (Panel B). Panel A: Eosinophils were incubated with various concentrations of *Trichoderma* xylanase for 3 hours. EDN concentrations in the supernatants were measured by RIA as an indicator of degranulation. Panel B: Naive BALB/c mice were exposed intranasally to various doses of *Trichoderma* xylanase. After 12 hours, BAL fluids were collected and the concentrations of IL-5 were measured by ELISA. Mean±range, n=2.

Effects of Glycolytic Enzyme Homologs on Immune Cell Activation In Vitro and In Vivo The following was performed to characterize the responses of eosinophils (in vitro) and mouse airways (in vivo) to the homologous enzymes from other fungal species, some of which are commercially available. In Table 1, *A. alternate* xylanase (a glycolytic enzyme) (AAF05698.1) was identified by pepstatin A-affinity chromatography of an *Alternaria* extract. Thus, the commercially available xylanase isolated from *Trichoderma viride* was used (Sigma catalog# X3876), and its biological activity examined. Incubation of isolated human eosinophils with *Trichoderma* xylanase induced EDN release (FIG. 21A). Instillation of *Trichoderma* xylanase into the airways of naïve mice induced increases in airway levels of IL-5 in vivo (FIG. 21B); IL-5 production was not inhibited in Rag-1-/- mice. Thus, the fungus-derived immunostimulatory activities are not limited to *Alternaria*, but are likely shared with certain other fungal species. Furthermore, the eosinophil activation assay in vitro and the mouse airway response in vivo, as well as the airway epithelial cell culture provide models to examine the effects of specific immunostimulatory molecules produced by fungi and to dissect the molecular mechanisms involved in this fungus-immune cell interaction.

Example 8

Characterizing the Airway Immune and Inflammatory Responses to Environmental Fungi in Patients with CRS PBMC are isolated from CRS patients with or without nasal polyps, AR patients and normal individuals, and their proliferative and cytokine responses to fungal antigens are compared. CD4+ cell proliferation is measured by dilution of the carboxyfluorescein diacetate succinimidyl ester (CFSE). Twenty-five cytokines and chemokines in the supernatants are quantitated simultaneously by a Luminex system.

Stimulated PBMC are stained with antibodies for cell surface markers and intracellular cytokines, and are analyzed by FACS to identify cells producing IL-5, IL-13, and IFN-γ. Special attention is focused on whether CD4+ T cells and CD56+ NK cells produce these cytokines.

Subjects. Patients with CRS are studied, using patients with AR and normal individuals as controls. Patients who received systemic glucocorticoids during the past 4 weeks, who are smokers, or who were diagnosed with an immunodeficiency or cystic fibrosis are excluded. The diagnosis of CRS is made based on the fulfillment of all three criteria: i) 2 or more of the following symptoms for more than 12 weeks—anterior or posterior mucopurulent drainage, nasal obstruction, facial pain-pressure-fullness, and decreased sense of smell; ii) anterior rhinoscopy or nasal endoscopy to document signs of inflammation; and iii) sinus CT scan demonstrating isolated or diffuse mucosal thickening. CRS with nasal polyps (CRSwNP) is defined as those CRS patients who now have or who had nasal polyps in the middle meatus, as determined by anterior rhinoscopy or nasal endoscopy. CRS without nasal polyps (CRSsNP) is defined as CRS patients who fulfill all three criteria for CRS as described above, but who do not have demonstrable nasal polyps in the middle meatus both in the past and at present.

Seasonal allergic rhinitis (AR) to ragweed. The clinical diagnosis of AR is established by history, where patients describe the typical seasonal signs of nose itching, sneezing and clear rhinorrhea, and is confirmed with a positive skin test and/or elevated specific serum IgE level for short ragweed antigen. Patients with AR are to have no history or symptoms of CRS or asthma and are to have normal lung function.

Normal Controls. The normal controls are healthy individuals with no history of allergy or asthma and negative skin prick test results to fungi and common aeroallergens.

Demographic Characterization of Patients and Normal Individuals.

Questionnaire: Each patient is asked to complete the questionnaire regarding the history of his or her sinus symptoms, aspirin sensitivity, sinus operations, and recently used and current medications. Patients are also asked regarding their history of asthma and AR, smoking habits, and use of allergen immunotherapy.

Skin tests: Skin prick tests are performed with a battery of 18 commercially available fungal extracts and 8 common aeroallergen extracts, including *Dermatophagoides pteron-*

*yssinus, D. farinae*, cockroach, short ragweed pollen, mixed grass pollen, mixed tree pollen, cat epithelium, and dog dander.

Total and specific IgE: Total serum IgE is measured by two-site ELISA. Allergen-specific IgE antibody levels are determined by RAST using 8 fungal allergens and 8 common aeroallergens.

Assessment of CRS: To assess the extent of the CRS, symptoms and quality of life (QOL) are scored according to the Symptom Score (0-10 visual analogue scale of 6 sinusitis-related symptoms and Gliklich and Metson QOL Score. Sinus CT scans are scored according to CT scoring systems described elsewhere (e.g., the Lund-Mackay staging system and the digital analysis of scanned images).

Sample Size

Given the conservative assumption that IL-5 is produced by PBMC from ≧83% of the patients with CRS and is produced in 36% of the normal controls, we are to have 80% power with a probability of a type 1 error rate of 0.05 with 20 patients in each group. Therefore, 20 CRSwNP, 20 CRSsNP, 20 AR, and 20 normal controls are recruited.

Cell Proliferation and Cytokine Production by PBMC

PBMC are cultured for 24 hours or 96 hours (for cytokine assay) or for 168 hours (for proliferation assay) with or without 25 µg/mL extracts of *Alternaria, Aspergillus, Cladosporium*, and short ragweed (Greer Laboratories), 2 µg/mL tetanus toxoid, or 5 µg/mL Con-A. The optimal concentrations of antigens and duration of culture have been determined elsewhere. The concentrations of a panel of 25 cytokines and chemokines (IL-1β, IL-Ra, IL-2, IL-2R, IL-4, IL-5, IL-6, IL-7, IL-8, IL-10, IL-12p40/p70, IL-13, IL-15, IL-17, TNF-α, IFN-α, IFN-γ, GM-CSF, MIP-1α, MIP-β, IP-10, MIG, eotaxin, RANTES, MCP-1) are measured by a Luminex 100 IS system (Upstate) and 25-plex antibody bead kit (BioSource International). The differences in the amounts of individual cytokine/chemokines among the groups are analyzed by Mann-Whitney U test. The pattern and cluster of cytokine production in each subject group are analyzed by Spotfire DecisionSite software (Somerville). For the CD4+ T cell proliferation assay, PBMC are labeled with 5 mM CFSE for 10 min before addition of antigens. After culture, PBMC are stained with PE-conjugated anti-CD4 and analyzed by FACS; CFSE dye is diluted in the proliferating population of the CD4+ T cells, and the numbers of cells that have proliferated per 1,000 CD4+ T cells are determined.

Figure 22:
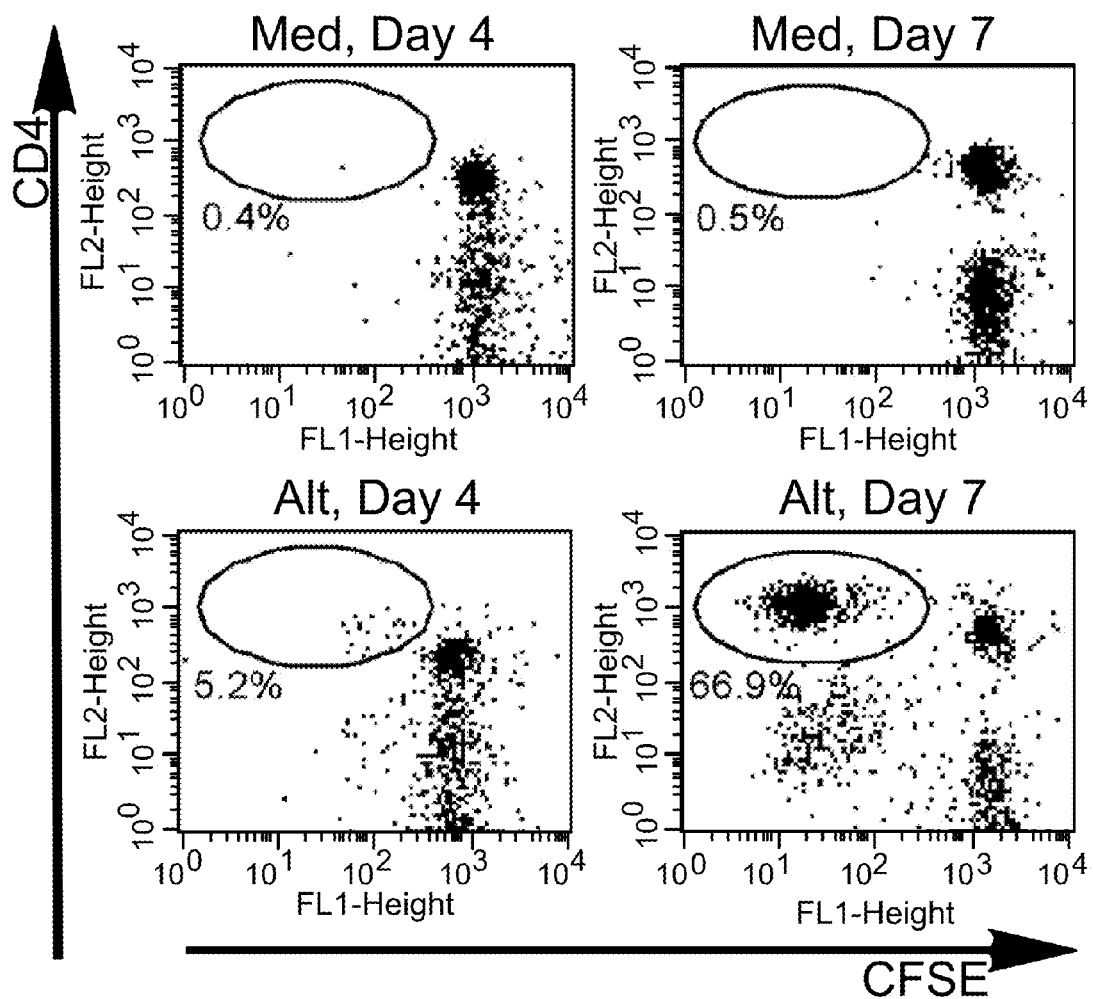
FIG. 22. PBMC proliferation monitored using CFSE labeling. PBMCs from a CRS patient were isolated, labeled with CFSE, and cultured in the presence of 25 µg/ml *Alternaria* extract (Alt) or medium alone (Med). On days 4 and 7, cells were collected, stained with CD4 PE, and analyzed by FACS. Numbers represent the percentage of $CFSE^{low}$ $CD4^+$ cells among total $CD4^+$ cells.
Figure 23:
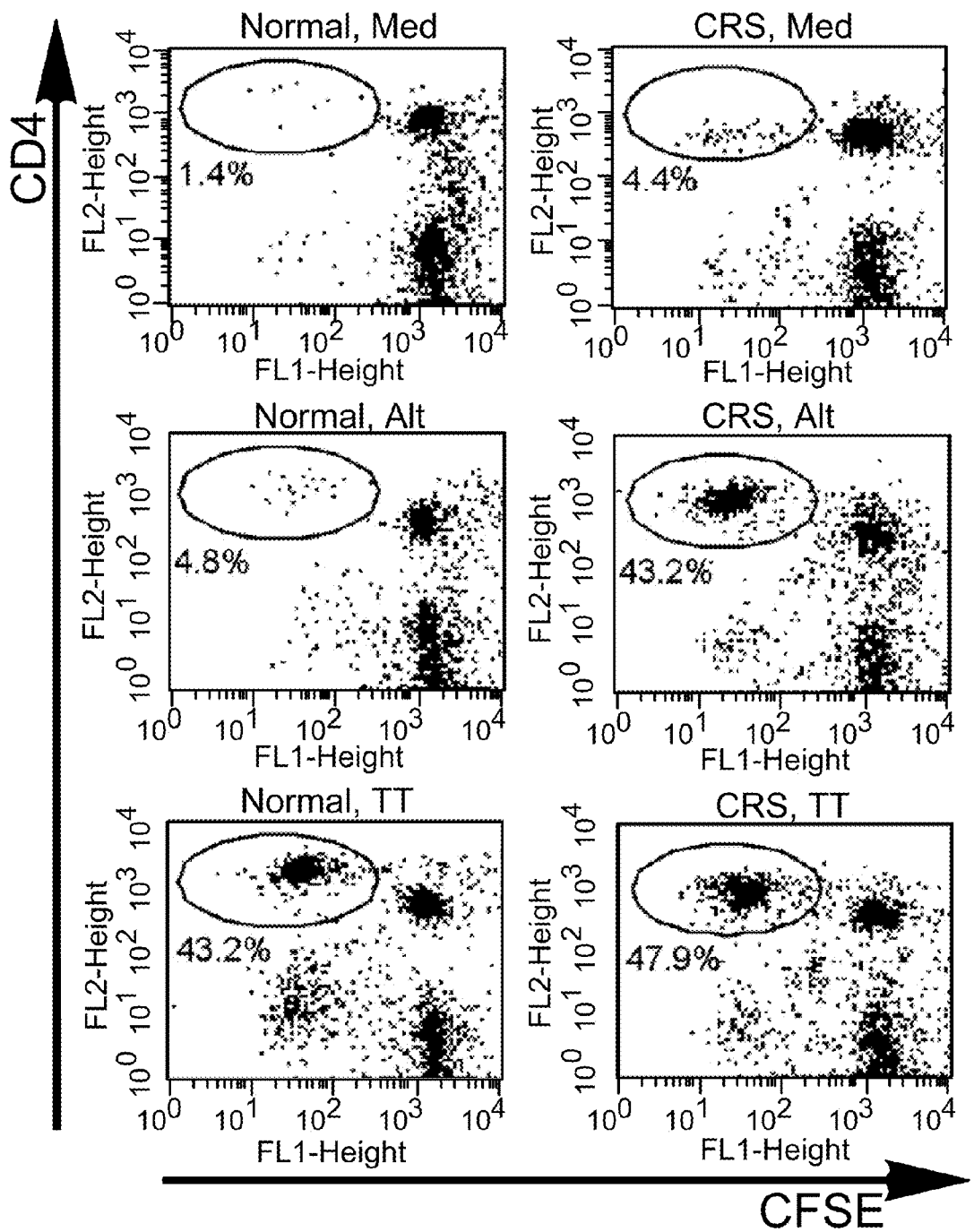
FIG. 23. Comparison of normal and CRS proliferation using CFSE labeling. PBMCs from a normal individual and a CRS patient were CFSE labeled and cultured with 25 µg/ml *Alternaria* extract (Alt), 2 µg/ml tetanus toxoid (TT) or medium alone (Med). On day 7, cells were collected, stained with CD4 PE, and analyzed by FACS.
Figure 24:
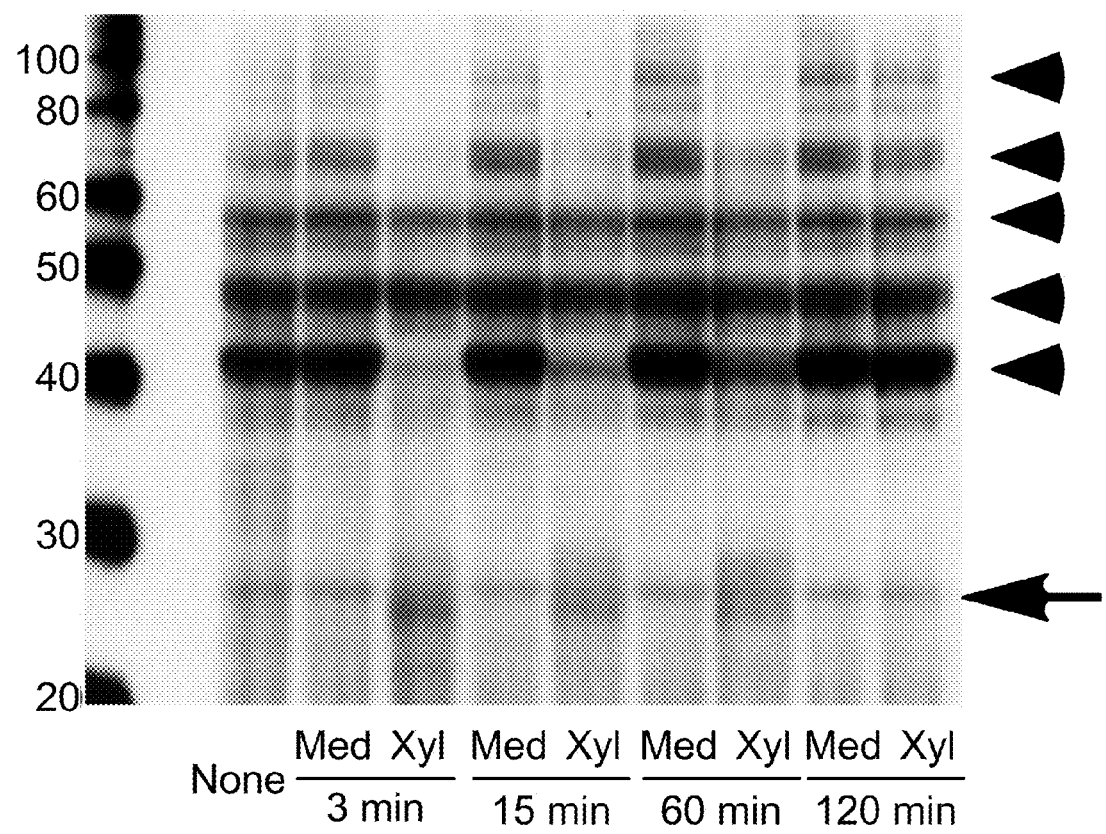
FIG. 24. Temporary deglycosylation and downregulation of PAR-2 by xylanase. Isolated eosinophils were incubated with medium alone (Med) or *Aspergillus* xylanase (Xyl) for the indicated time. Cells were lysed and analyzed for PAR-2 molecules by anti-PAR-2 antibody (which recognizes the N-terminus of the molecule) and Western blot. The 41 kDa and 70 kDa PAR-2 molecules were deglycosylated by xylanase temporarily. Arrow; PAR-2 core protein, Arrow heads; glycosylated PAR-2 molecules.

A pilot study showed that when PBMCs from a CRS patient were stimulated with *Alternaria* extract, a population of CFSElow CD4+ T cells emerged by day 4, and represented 66.9% of total CD4+ T cells on day 7 (FIG. 22); no changes were observed in PBMCs cultured in medium alone. A side-by-side comparison of a normal individual and a CRS patient in a separate experiment (compared on day 7) showed that a higher proportion of CD4+ cells were CFSElow in the CRS patient than those in the normal individual (43.2% vs. 4.8%) (FIG. 23). In contrast, many CD4+ cells were CFSElow in both the CRS patient and normal individual when they were stimulated with tetanus toxoid (43.2% vs. 47.9%).

FACS Analyses of Cytokine Producing Cells

The PBMCs producing IL-5, IL-13 and IFN-γ are analyzed by FACS. IL-5 is likely produced by CD4+ T cells, CD8+ T cells, and CD56+NK cells. Thus, FITC-conjugated antibodies are used for these cell surface markers and PE-conjugated antibodies to IL-4, IL-5, IL-13, and IFN-γ to identify cytokine-producing cells. After stimulation with antigens, PBMC are re-stimulated with ionomycin plus PMA in the presence of brefeldin A. Cell surface antigens are stained with FITC-conjugated anti-CD3, CD4, CD8 or CD56 (Becton Dickinson). After washing, cells are fixed and permeabilized simultaneously by Cytofix/Cytoperm solution (Pharmingen), and stained with PE-conjugated anti-cytokine or control mouse Ig.

In Vitro Organ Culture of Sinus Tissue Specimens from CRS Patients Produce Distinctive Pro-Inflammatory Cytokines Large quantities of sinus tissue specimens are obtained from CRS patients during endoscopic sinus surgery. Specimens from the ethmoid sinuses of normal individuals (non-allergic, no asthma, no CRS) undergoing septoplasty procedures are used as a negative control. Other disease control specimens are obtained from patients with AR, who undergo septoplasty.

To examine the immunological responses by sinus mucosa to fungi, an organ culture system is used, rather than isolated mononuclear cells. Organ culture can allow for the study the mucosal immune responses and tolerance that are likely be mediated by a complex network of epithelial cells, antigen presenting cells, lymphocytes and potentially other mucosal resident cells, and each cellular component may play an role. Tissues are minced into 5-mm pieces, and then cultured with fungal extracts (e.g., *Alternaria, Cladosporium, Aspergillus*), Con-A or tetanus toxoid for 24 hours or 96 hours. First, the concentrations of 25 cytokines and chemokines, including IL-10, in the supernatants are analyzed by a Luminex system. The concentration of TGF-β is measured by ELISA. Second, once several cytokines (e.g. IL-5) are verified to be produced at elevated levels during the CRS organ culture, the cell types that produce these cytokines are identified. After antigenic stimulation for 96 hours, the tissue specimens are treated with a cocktail of highly pure collagenases (Blendzyme 3, Roche). In preliminary studies, the yield was 12 to 70×10$^6$ cells/specimen, and the viability was 65~95%. The single cell suspension are recovered after passing through a nylon mesh with 100 µm pore size. The cell types (CD4+, CD8+, CD56+) producing cytokines (IL-5, IL-13, IFN-γ) are analyzed by intracellular cytokine staining and FACS analysis.

Subjects. Patients with CRS, who are undergoing endoscopic sinus surgery, are studied, using normal individuals as controls. The criteria for CRS patients and normal individuals are the same as described above. The patients with CRSwNP are enrolled because the patients with CRSwNP tend to have more expensive disease than those with CRSsNP. For this study, patients who are not using nasal or inhaled steroids for 4 weeks before the surgery are specifically selected. The goal is to detect at least 1.5 SD differences in means between two groups as significant with 80% power with a probability of a type I error rate of 0.05. Therefore, tissues from 7 CRS patients and 7 normal controls for each of the 3 experiments are obtained. Because the sample size is not based on preliminary data, a second power calculation is performed once 7 subjects in each group have completed the study. If there is a risk for type II error, the sample size is increased.

Analyses of the functions of CD4+CD25+ regulatory T cells. CD4+ T cells are isolated from single cell suspensions of sinus tissue fragments by negative immunomagnetic selection, followed by positive selection for CD25+ cells by magnetic cell sorting (StemCell Technologies). Isolated CD4+ CD25− cells are incubated with serial dilutions of isolated CD4+CD25+ cells in the presence of autologous irradiated mononuclear cells for 96 hours and in the presence or absence of fungal extract (e.g. *Alternaria*). The production of cytokines (IL-5, IL-13, IFN-γ) in the supernatant is measured by ELISA, and the proliferation of CFSE-labeled CD4+CD25− cells is examined. In some experiments, antibodies to IL-10 and IL-10Rα-chain and a soluble TGF-βRII-Fc chimeric protein (all from R&D systems) are included in the culture to examine the role of IL-10 and TGF-β to dampen the cytokine and proliferative responses.

In Vivo Intranasal Challenge with *Alternaria* in CRS Patients

Subjects. CRS patients without demonstrable IgE antibodies to *Alternaria* are studied using CRS patients with IgE antibodies to *Alternaria* and normal individuals as controls. The criteria for CRS patients and normal individuals are the same as described above, and patients who are not on nasal or inhaled steroids for 4 weeks before the study are selected. The presence or absence of IgE antibodies to *Alternaria* is examined by both skin tests and IgE RAST. About 30% of patients with CRS have demonstrable IgE antibodies to *Alternaria*. Asthma is not required for inclusion; if CRS patients do have a history of asthma, they may be included in the study if their asthma is mild as defined by all of the following parameters; (1) a baseline FEV1 of more than or equal to 80% of predicted, (2) no need for any maintenance therapy for asthma with inhaled steroids, long-acting bronchodilators, or systemic steroids, (3) no need for treatment with theophylline or leukotriene inhibitors on daily basis, and (4) no history of emergency room visits or hospitalization because of asthma in the last ten years. Based on preliminary data, for a dichotomous endpoint (e.g., detectable level of IL-5), a sample-size of n=10 per group provides statistical power of 84% to detect a difference between groups. Statistical power is increased when data are analyzed as continuous variables. 10 subjects are recruited for each of the 3 groups.

Intranasal challenge and sample collection. Intranasal challenge with *Alternaria* is performed as described elsewhere. Briefly, before nasal challenge, CRS patients with IgE antibodies to *Alternaria* undergo endpoint titration to establish the optimal dose for starting their intranasal challenge. Endpoint titration is performed by a skin prick test with escalating or decreasing dosages of *Alternaria* extract (ALK Abello, product#ALTE21P41L) starting at 18 PNU/mL. If there is no reaction (wheal and flare) at 18 PNU/mL, the next higher concentration is tested until a wheal and flare response occurs. If there is a reaction at 18 PNU/mL, the next lowest concentration is tested until no wheal and flare develops. The starting dosage for the nasal challenge for CRS patients with anti-*Alternaria* IgE antibody is the highest concentration that causes no wheal and flare response. CRS patients who do not have IgE antibody to *Alternaria* (i.e., both skin test negative and RAST negative) or normal individuals are started at 18 PNU/mL. For nasal challenge, the *Alternaria* extract (ALK Abello, product# ALTE21P41L) is administered by a metered nasal spray pump (Callipot) that delivers 0.1 mL of extract per nostril. If no reaction occurs, it is proceed with a 3-fold higher concentration (e.g. 54 PNU/mL) up to 40,000 PNU/mL. The interval between each challenge is 15 minutes. The cumulative dose of *Alternaria* received by each subject is <12,000 PNU. The nasal lavage specimens are collected before and 24 hours after the challenge. Three milliliters of saline are introduced into each nostril, and secretions are collected into a container. The specimens are processed immediately for cell count and differentials, and supernatants are stored for cytokine and eosinophil granule protein assays. The peak expiratory flow rate (PEFR) is measured at baseline and after each dose. A pulmonary function test (flow volume loop) is performed with measurement of forced expiratory volume 1 (FEV1) before, immediately after, and 24 hours after the escalating intranasal challenge protocol. There is a stopping rule in place. At baseline and after each challenge, all subjects are asked for their symptoms. These symptoms (nasal blockage, nasal discharge, number of sneezes, nasal itching, difficulty breathing, cough or wheezing) are recorded on a four-point scale (0 to 3). The total symptom score is calculated as the sum of the individual symptom scores. The nasal challenge is stopped at the dosage of *Alternaria* extract that produces either: i) 1 mL of nasal secretions or more than 5 sneezes within 15 minutes, ii) a symptom score of 3 for two or more of the symptoms mentioned above, or iii) difficulty breathing with a decrease of the PEFR or FEV1 by 15% or more.

Samples and data obtained. Nasal lavage fluids are collected from study subjects before and 24 hours after intranasal challenge, and the total leukocyte counts and differentials are determined. The concentrations of cytokines/chemokines, including IL-4, IL-5, IL-13, IFN-γ, TNF-α, IL-10, and eotaxin, in nasal lavage fluids are quantitated by specific ELISA (Endogen). The sensitivity of these ELISA is generally <0.7 pg/mL. Eosinophil granule MBP and EDN are analyzed by RIA to monitor eosinophilic inflammation.

Example 9

Identifying *Alternaria* Products that Trigger Profound Th2-Like Inflammation In Vitro in Human Airway Cells and In Vivo in Mouse Airways The following describes methods and materials for producing recombinant candidate *A. alternate* immunomodulatory proteins and characterizing their immune responses in vitro and in vivo. Purified recombinant forms of the *Alternaria* protein candidates are produced. These proteins are used to perform various in vitro and in vivo immunological assays and to elucidate the role of these proteins individually and in concert in CRS pathogenesis.

Candidate proteins identified is Table 1 are expressed recombinantly. Constructs are made to consist of the following: 1) the trpC and ToxA promoter, 2) a PCR amplified cDNA or genomic region from *A. alternata* corresponding to the full-length candidate genes of the enzymes, and 3) a PCR generated histidine tag (e.g., 6×-His) engineered just prior to the stop codon (C-terminus) to aid in purification. These constructs are then introduced into *A. alternata* protoplasts using standard polyethylene glycol (PEG)-mediated fungal transformation approaches. Individual mutants are grown in potato dextrose broth with hygromycin, and expression levels of the introduced genes are verified using RT-PCR or northern blotting, and SDS-PAGE. Individual mutants exhibiting high-level expression of the protein of interest are grown in larger amounts, culture filtrates are purified, and Immobilized Metal Affinity Chromatography (IMAC) for the histidine-tagged protein purification involves using a HPLC system and Ni Sepharose chromatography.

Alternatively, routine recombinant protein expression systems with organisms like *E. coli* and *Pichia pastoris* are used. For example, *E. coli* was used to produce one of eight candidates, *A. alternata* xylanase (AAF05698.1) (FIG. 26).

In Vitro and In Vivo Assays for Activity of Recombinant *Alternaria* Proteins.

Eosinophil [Ca2+]i response and degranulation. For degranulation, isolated eosinophils are incubated with different concentrations of recombinant proteins (10 ng/mL–1 mg/mL) for 3 hours, and EDN released into supernatants is measured by RIA to indicate degranulation. Changes in [Ca2+]i are measured using FACS analysis and eosinophils loaded with a calcium indicator, indo-1. The involvement of PAR-2 and proteolytic/glycolytic enzymes is verified by a PAR-2 peptide antagonist, LSIGKV (SEQ ID NO:35), and enzyme inhibitors, such as pepstatin A-agarose, ATBI, ritonavir, and allosamidine. The active cleavage of PAR-2 is verified by fluorescent quenched peptide substrate [Abz-SKGRSLIGK(Dnp)D] (SEQ ID NO:37) and by analysis of stimulated eosinophils by FACS and immunoblot using anti-PAR-2 antibody (which recognizes the N-terminus of PAR-2).

Although unlikely, the involvement of TLR2 or TLR4/CD14 is examined using blocking antibodies to these molecules (eBioscience).

Epithelial cell production of cytokines. The airway epithelial cell line, BEAS-2B, is stimulated with different concentrations of recombinant proteins for 24 hours, similarly to *Alternaria* crude extract experiments in FIGS. 10 and 11. Cytokines, including IL-8 and IL-6, released into supernatant are measured by ELISA. The epithelial cells' PAR-2 is analyzed similarly to the analysis for eosinophils.

Cytokine responses and airway eosinophilia in mouse airways in vivo. Naïve mice are exposed intranasally to recombinant proteins (1 µg-100 µg/challenge) on days 0, 3, and 6 (see FIGS. 16 and 20). At 12 hours after the first challenge, on day 5, or day 8, the trachea is cannulated, and the lung is lavaged with 0.5 mL of HBSS. Total numbers of cells and differentials in BAL fluids are determined. Supernatants are collected, and the concentrations of cytokines (IL-5, IL-4, IL-13, IFN-γ) are measured by ELISA. Tissue samples of the lungs are examined histologically. Blood is collected by cardiac puncture on day 8 to quantitate IgE and IgG antibodies to recombinant proteins.

Cellular and humoral immune responses by CRS patients. PBMC are isolated from normal individuals and CRS patients by using the same criteria as described above. PBMC are incubated with serial dilutions of recombinant proteins for 24 hours (for IL-4), for 96 hours (for IL-5, IL-13, and IFN-γ), or for 168 hours for CFSE-based CD4+ T cell proliferation assay as described above. Serum concentrations of IgE, IgG, and IgG4 antibody to recombinant proteins are measured by immunoassay and western blot.

Development of *A. alternata* Knockout (KO) Mutants for Specific Immunostimulatory Proteins and Analyses of Immune Responses In Vitro and In Vivo with Whole Fungi and Fungal Products.

KO mutants are generated for each candidate immunostimulatory protein. First, the secreted products from KO *A. alternata* are used to deduce whether the absence of a specific protein significantly affects the activation of immune cells in vitro and in vivo. Second, similar experiments with whole fungus (i.e., fungal spores and fungal hyphae) are compare the immune responses triggered by KO to the wild type.

Fungal mutant generation. The LME approach is used as described above to disrupt the target genes. The LME constructs consistently produce stable transformants for diverse categories of genes. Typically, when using the LME constructs, 100% of the transformants are targeted gene disruption mutants compared to inconsistent transformation and usually less than 10% targeted gene disruption with circular plasmid disruption constructs. All mutants are subjected to molecular characterization to confirm that gene(s) are disrupted.

In vitro and in vivo assays. Wild-type and KO *Alternaria* are cultured in liquid medium. Proteins released from these fungi into supernatants are analyzed for their immunostimulatory activities in vitro with eosinophils and BEAS-2B cells and in vivo mouse airways as described above. Spores are collected from wild-type and KO *Alternaria*. These spores are cultured in vitro in HBSS medium with airway mucin and allowed to germinate. Eosinophils are added, and their responses to wild-type and KO *Alternaria* are examined as in FIG. 13.

Example 10

Inhibiting *Alternaria*-Induced Eosinophilic Degranulation

To monitor eosinophil function in response to extracts from *Alternaria*, degranulation of human eosinophils was measured by quantitating released eosinophil-derived neurotoxin (EDN) and/or MBP. In brief, freshly isolated eosinophils were suspended in HBSS with 25 mM HEPES and 0.01% gelatin at $5 \times 10^5$ cells/mL. Eosinophils and stimuli were incubated in 96-well tissue culture plates for 3 hours at 37° C. and 5% $CO^2$. Cell-free supernatants were stored at −20° C. A specific RIA quantitated eosinophil degranulation by measuring the concentration of EDN in the supernatants. The following inhibited *Alternaria*-induced eosinophilic degranulation: CV6209 (PAF receptor antagonist), heparin, EDTA, EGTA, pepstatin agarose, PAR2-inhibitory peptide, Jasplakinlide (actin inhibitor), and Lanthunum (Ca channel inhibitor). The following did not inhibit eosinophilic degranulation: Chymostatin, Chloroquine, Phosphoramidon, APSF, Calpastatin, Antipain, Bestatin, Leupeptin, Pefabloc SC, Aprotinin, Cytochalasin B, Colchitin, E64, Calpain inhibitor, SB203580 (p38 MAPK inhibitor), Genistein, Wortmannin, Ro-31-8220, Rottelrin, GF109203X, PD98059 (ERK inhibitor), Cyclosporin A, FK 506, W-7, and TLCK.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A substantially purified polypeptide comprising the 10 amino acid sequence set forth in SEQ ID NO:14.

* * * * *

UNITED STATES PATENT AND TRADEMARK OFFICE
CERTIFICATE OF CORRECTION

PATENT NO. : 7,972,611 B2
APPLICATION NO. : 12/973100
DATED : July 5, 2011
INVENTOR(S) : Hirohito Kita Page 1 of 1

It is certified that error appears in the above-identified patent and that said Letters Patent is hereby corrected as shown below:

Title Page, Item (75), Inventors, after Christopher Lawrence, please delete "Blackburg" and insert --Blacksburg-- therefor;

Title Page, Item (57), Abstract, before "methods for assessing" please delete "fungal polypeptides,";

Column 1, lines 22-25, please delete "This invention was made with government support under AI049235 awarded by the National Institute of Allergy and Infectious Disease. The government has certain rights in the invention." and insert --This invention was made with government support under AI049235 awarded by the National Institutes of Health. The government has certain rights in the invention.-- therefor.

Signed and Sealed this
Twenty-seventh Day of March, 2012

David J. Kappos
*Director of the United States Patent and Trademark Office*

SEQUENCE LISTING

```
<160> NUMBER OF SEQ ID NOS: 38

<210> SEQ ID NO 1
<211> LENGTH: 1461
<212> TYPE: DNA
<213> ORGANISM: Alternaria brassicicola

<400> SEQUENCE: 1
atgcatttcc gcggatcctc catctacttc ggcatcgttg ccctctcctc gacttcagct      60
```

```
gtccttggag ccgtcgctcc ctacggacaa tgcggtggta acggcttcca gggcgagacc    120
gagtgcgctc aaggctggtc ttgcgtcaag agcaacgact ggtacagcca gtgcatcaac    180
ggtggtggaa acgccccggc tcctcctgct gctactggcg tcgcgccggc accgtcatt     240 ccttctgccg ccctgtacc gtcgatgaac gctagcgagc ccgtcgccgc ccctgttgcg    300
gttgctcagc ctgctgccac cggcggtgcc aacggctctg ctcctgatgt tgccggaacc    360
ggtgccaacg gtgccaagtg ctcgctcgat gctgcattca gtcgcacgg caagaagtac     420 atcggtgttg ctaccgacca gggcgcactc agcaagggaa agaacaagga gatcatcgtc    480
gcaaacttcg gccaggttac tcctgagaac agcatgaagt gggatgccac cgagggtacc    540
gagggcaagt tcactctcga cggtgccaac gcgctcgtca gctttgccac ggagaacaag    600
aagctcgtcc gcggtcacac caccgtctgg cactctcagc ttcccacctg ggtctcttcc    660
atcaccgaca agactaagct cgaggaagtc atggttgctc acatcaagaa gctcatgagc    720
acctacgccg gcaaggtcta tgcttgggac gtagtcaacg agatcttcaa cgaagacggt    780
tctttccgct cttccgtctt ctacaacgtt ctcggtgaga actttgtcgc taccgctttc    840
gctactgcca aggccgccga cccagaggcc aagctctaca tcaacgacta caacctcgac    900
agccccagtt acgctaagac caaggccatg gctagcaacg tcaagaagtg ggttgccgcc    960
ggtgttccca ttgacggtat tggttcccag tcccacttgt ccggcagctg gcccatctcc   1020
gactaccccg ctgctctcaa gcttctctgc gagtctgctt ccgagtgcgc catgactgag   1080
cttgacatca agggtggtgc tgccgctgac tacaagactg ctgtcactgc ttgcttggat   1140
gtcgagaact gtgttggtgt taccgtctgg ggtgttagcg acactgactc ttggatcggc   1200
gctgctgcca ctcctctgct tttcgacggc agcttccagg ccaaggagtc ttacaacggt   1260
ctctgctccg ctcttgctta aatgcacagg gtgagaacga gggcatccga ttagatctat   1320
cagcttaaga cagacaattt ggtgcttgaa aaaggtgttt gtttcttgta ggagatggga   1380
tgaaattcta ccgtatatat atctactttg gtaagatggt aaactccatc ttccaattga   1440
tcattttatt gaaaaaaaaa a                                              1461
```

<210> SEQ ID NO 2
<211> LENGTH: 426
<212> TYPE: PRT
<213> ORGANISM: Alternaria brassicicola

<400> SEQUENCE: 2

```
Met His Phe Arg Gly Ser Ser Ile Tyr Phe Gly Ile Val Ala Leu Ser
1               5                   10                  15

Ser Thr Ser Ala Val Leu Gly Ala Val Ala Pro Tyr Gly Gln Cys Gly
            20                  25                  30

Gly Asn Gly Phe Gln Gly Glu Thr Glu Cys Ala Gln Gly Trp Ser Cys
        35                  40                  45

Val Lys Ser Asn Asp Trp Tyr Ser Gln Cys Ile Asn Gly Gly Gly Asn
    50                  55                  60

Ala Pro Ala Pro Pro Ala Ala Thr Gly Val Ala Pro Ala Pro Val Ile
65                  70                  75                  80

Pro Ser Ala Ala Pro Val Pro Ser Met Asn Ala Ser Glu Pro Val Ala
                85                  90                  95

Ala Pro Val Ala Val Ala Gln Pro Ala Ala Thr Gly Gly Ala Asn Gly
            100                 105                 110

Ser Ala Pro Asp Val Ala Gly Thr Gly Ala Asn Gly Ala Lys Cys Ser
        115                 120                 125
```

```
Leu Asp Ala Ala Phe Lys Ser His Gly Lys Lys Tyr Ile Gly Val Ala
            130                 135                 140

Thr Asp Gln Gly Ala Leu Ser Lys Gly Lys Asn Lys Glu Ile Ile Val
145                 150                 155                 160

Ala Asn Phe Gly Gln Val Thr Pro Glu Asn Ser Met Lys Trp Asp Ala
                165                 170                 175

Thr Glu Gly Thr Glu Gly Lys Phe Thr Leu Asp Gly Ala Asn Ala Leu
            180                 185                 190

Val Ser Phe Ala Thr Glu Asn Lys Lys Leu Val Arg Gly His Thr Thr
        195                 200                 205

Val Trp His Ser Gln Leu Pro Thr Trp Val Ser Ile Thr Asp Lys
    210                 215                 220

Thr Lys Leu Glu Glu Val Met Val Ala His Ile Lys Lys Leu Met Ser
225                 230                 235                 240

Thr Tyr Ala Gly Lys Val Tyr Ala Trp Asp Val Val Asn Glu Ile Phe
                245                 250                 255

Asn Glu Asp Gly Ser Phe Arg Ser Ser Val Phe Tyr Asn Val Leu Gly
            260                 265                 270

Glu Asn Phe Val Ala Thr Ala Phe Ala Thr Ala Lys Ala Ala Asp Pro
        275                 280                 285

Glu Ala Lys Leu Tyr Ile Asn Asp Tyr Asn Leu Asp Ser Pro Ser Tyr
290                 295                 300

Ala Lys Thr Lys Ala Met Ala Ser Asn Val Lys Lys Trp Val Ala Ala
305                 310                 315                 320

Gly Val Pro Ile Asp Gly Ile Gly Ser Gln Ser His Leu Ser Gly Ser
                325                 330                 335

Trp Pro Ile Ser Asp Tyr Pro Ala Ala Leu Lys Leu Leu Cys Glu Ser
            340                 345                 350

Ala Ser Glu Cys Ala Met Thr Glu Leu Asp Ile Lys Gly Gly Ala Ala
        355                 360                 365

Ala Asp Tyr Lys Thr Ala Val Thr Ala Cys Leu Asp Val Glu Asn Cys
    370                 375                 380

Val Gly Val Thr Val Trp Gly Val Ser Asp Thr Asp Ser Trp Ile Gly
385                 390                 395                 400

Ala Ala Ala Thr Pro Leu Leu Phe Asp Gly Ser Phe Gln Ala Lys Glu
                405                 410                 415

Ser Tyr Asn Gly Leu Cys Ser Ala Leu Ala
            420                 425

<210> SEQ ID NO 3
<211> LENGTH: 1350
<212> TYPE: DNA
<213> ORGANISM: Alternaria brassicicola

<400> SEQUENCE: 3
atgtctgccc ccgcccacaa gttcaaggtt gccgacatca gtcttgcggc gttcggtcgc      60
cgcgagattg agctcgccga gaatgagatg cctggtctga tggagactcg ccgcaagtat     120
gctgaggacc agccattgaa gggcgcccgc attgctggat gtctgcacat gaccatccag     180
actgccgttc tcatcgagac gctcaagtcc ctcggtgctg agctcacctg acatcctgc      240 aacatcttct ccacccagga ccacgctgcc gctgccattg ccgctgccgg cgtacctgtc     300
ttcgcctgga agggcgagac cgaggaggag tacgagtggt gccttgagca gcaactcaca     360
gctttcaagg acggcaagag cctgaacttg atccttgacg acggtggcga cctcactgcc     420
cttgtccaca agaagtaccc tgagatgctc aaggactgct acggtgtctc ggaagagacc     480
```

```
accactggtg tccaccacct ctaccgcatg ttgaagggca agggtctcct cgtccccgcc   540
atcaacgtca acgactccgt caccaagtcc aagttcgaca acttgtacgg ttgccgtgag   600
tcgctcgtcg acggcatcaa gcgtgcgacc gacgtcatga ttgctggcaa ggtcgccgtc   660
gtcgctggtt tcggtgatgt cggcaagggt tgcgcccagg ctctccacag catgggtgcc   720
cgtgtcatcg tcaccgagat tgaccccatc aacgccctcc aggctgccgt ttccggcttc   780
caggttacca ccatggagaa ggccgctcct cagggtcaga tcttcgtcac caccactggt   840
tgccgtgaca tcctgactgg cgtccacttc gaggctatgc ccaacgatgc catcgtctgc   900
aacatcggtc acttcgacat cgaaatcgac gttgcgtggc tcaagaagaa cgccaagtcc   960
gtcaccagca tcaagcccca ggtcgaccgc tacctgatga caatggccg ctacatcatc  1020 ctcctcgctg agggccgtct cgtcaacttg ggatgcgcca ctggccactc ttccttcgtc  1080
atgtcctgct ctttcaccaa ccaggtcctt gcccagatta tgctgtacaa ggcctctgac  1140
gaggagtttg caacaagta cgtcgagttc ggcaagaccg gtaagctcga tgtcggtgtc  1200
tacgttctgc ccaagattct cgacgagcaa gtcgctcttc tccacttggc acacgtcaac  1260
gttgagctct ccaagctcag cgatgtccag gccgagtacc ttggtctccc tgttgagggt  1320
cctttcaaga gcgacatcta ccgttactag                                    1350
```

<210> SEQ ID NO 4
<211> LENGTH: 449
<212> TYPE: PRT
<213> ORGANISM: Alternaria brassicicola

<400> SEQUENCE: 4

```
Met Ser Ala Pro Ala His Lys Phe Lys Val Ala Asp Ile Ser Leu Ala
1               5                   10                  15

Ala Phe Gly Arg Arg Glu Ile Glu Leu Ala Glu Asn Glu Met Pro Gly
            20                  25                  30

Leu Met Glu Thr Arg Arg Lys Tyr Ala Glu Asp Gln Pro Leu Lys Gly
        35                  40                  45

Ala Arg Ile Ala Gly Cys Leu His Met Thr Ile Gln Thr Ala Val Leu
    50                  55                  60

Ile Glu Thr Leu Lys Ser Leu Gly Ala Glu Leu Thr Trp Thr Ser Cys
65                  70                  75                  80

Asn Ile Phe Ser Thr Gln Asp His Ala Ala Ala Ile Ala Ala
                85                  90                  95

Gly Val Pro Val Phe Ala Trp Lys Gly Glu Thr Glu Glu Tyr Glu
            100                 105                 110

Trp Cys Leu Glu Gln Gln Leu Thr Ala Phe Lys Asp Gly Lys Ser Leu
        115                 120                 125

Asn Leu Ile Leu Asp Asp Gly Gly Asp Leu Thr Ala Leu Val His Lys
    130                 135                 140

Lys Tyr Pro Glu Met Leu Lys Asp Cys Tyr Gly Val Ser Glu Glu Thr
145                 150                 155                 160

Thr Thr Gly Val His His Leu Tyr Arg Met Leu Lys Gly Lys Gly Leu
                165                 170                 175

Leu Val Pro Ala Ile Asn Val Asn Asp Ser Val Thr Lys Ser Lys Phe
            180                 185                 190

Asp Asn Leu Tyr Gly Cys Arg Glu Ser Leu Val Asp Gly Ile Lys Arg
        195                 200                 205

Ala Thr Asp Val Met Ile Ala Gly Lys Val Ala Val Ala Gly Phe
    210                 215                 220
```

```
Gly Asp Val Gly Lys Gly Cys Ala Gln Ala Leu His Ser Met Gly Ala
225                 230                 235                 240

Arg Val Ile Val Thr Glu Ile Asp Pro Ile Asn Ala Leu Gln Ala Ala
            245                 250                 255

Val Ser Gly Phe Gln Val Thr Thr Met Glu Lys Ala Ala Pro Gln Gly
        260                 265                 270

Gln Ile Phe Val Thr Thr Thr Gly Cys Arg Asp Ile Leu Thr Gly Val
    275                 280                 285

His Phe Glu Ala Met Pro Asn Asp Ala Ile Val Cys Asn Ile Gly His
290                 295                 300

Phe Asp Ile Glu Ile Asp Val Ala Trp Leu Lys Lys Asn Ala Lys Ser
305                 310                 315                 320

Val Thr Ser Ile Lys Pro Gln Val Asp Arg Tyr Leu Met Asn Asn Gly
            325                 330                 335

Arg Tyr Ile Ile Leu Leu Ala Glu Gly Arg Leu Val Asn Leu Gly Cys
        340                 345                 350

Ala Thr Gly His Ser Ser Phe Val Met Ser Cys Ser Phe Thr Asn Gln
    355                 360                 365

Val Leu Ala Gln Ile Met Leu Tyr Lys Ala Ser Asp Glu Glu Phe Gly
370                 375                 380

Asn Lys Tyr Val Glu Phe Gly Lys Thr Gly Lys Leu Asp Val Gly Val
385                 390                 395                 400

Tyr Val Leu Pro Lys Ile Leu Asp Glu Gln Val Ala Leu Leu His Leu
            405                 410                 415

Ala His Val Asn Val Glu Leu Ser Lys Leu Ser Asp Val Gln Ala Glu
        420                 425                 430

Tyr Leu Gly Leu Pro Val Glu Gly Pro Phe Lys Ser Asp Ile Tyr Arg
    435                 440                 445

Tyr

<210> SEQ ID NO 5
<211> LENGTH: 840
<212> TYPE: DNA
<213> ORGANISM: Alternaria brassicicola

<400> SEQUENCE: 5
atgaagtctg tagctgtcct ccccgccatc ttggccctgg cccacgccca cgccactttc      60
caacaactct ggaagaacgg aaaggatctg gagagcacct gtgccaggtt gccaccgtcc     120
aacagccctg ttgaggacta caccagcaac gctctgcaat gcaacgtcag ccctgctcct     180
gccgagggaa agtgcgcttt cgaggccggt gacacggtaa ccatcgagat gcaccagcac     240
aacacccgtg actgcaagga ggaaggtatt ggtggtgccc actggggccc tgtcctcgca     300
tacatgtcca aggttgagga cgcagccacc gcagatggct ccagcgagtt cttcaaggtt     360
taccagaaca cctgggctaa gaacccagac gccactcagg gcgacaacga cttttggggt     420
accaaggacc tcaactacaa ctgcggaaag ctcgactttg ccattcccaa gaacattgct     480
cctggtgact acctcctccg tgccgaggcc atcgccctcc acgctgcaag cgcaggagga     540
ggagcgcaac attatatgac gtgcttccaa cttactgtca ccggcagcgg aactctggag     600
cccaagggtg tcaccttccc tgaggcgtac tccaagactg tctcggtct ggtttctcc      660 atccacgccg acctcgactc ataccctgct cctggtcccg agctcatcca agcggtactg     720
aggtcacccc tcagctcctc acctttggcg agctcgctgg tgcccctgct gccaccgcca     780
ccggtggtgc cgccgagacc ccggctgctt ccaccccgct tcgtcgctgt cttcttcacc     840
```

<210> SEQ ID NO 6
<211> LENGTH: 491
<212> TYPE: PRT
<213> ORGANISM: Alternaria brassicicola

<400> SEQUENCE: 6

```
Met His Gln His Asn Thr Arg Asp Cys Lys Glu Glu Gly Ile Gly Gly
1               5                   10                  15

Ala His Trp Gly Pro Val Leu Ala Tyr Met Ser Lys Val Glu Asp Ala
            20                  25                  30

Ala Thr Ala Asp Gly Ser Ser Glu Phe Phe Lys Val Tyr Gln Asn Thr
        35                  40                  45

Trp Ala Lys Asn Pro Asp Ala Thr Gln Gly Asp Asn Asp Phe Trp Gly
50                  55                  60

Thr Lys Asp Leu Asn Tyr Asn Cys Gly Lys Leu Asp Phe Ala Ile Pro
65                  70                  75                  80

Lys Asn Ile Ala Pro Gly Asp Tyr Leu Leu Arg Ala Glu Ala Ile Ala
                85                  90                  95

Leu His Ala Ala Ser Ala Gly Gly Ala Gln His Tyr Met Thr Cys
            100                 105                 110

Phe Gln Leu Thr Val Thr Gly Ser Gly Thr Leu Glu Pro Lys Gly Val
            115                 120                 125

Thr Phe Pro Glu Ala Tyr Ser Lys Thr Gly Leu Gly Leu Gly Phe Ser
130                 135                 140

Ile His Ala Asp Leu Asp Ser Tyr Pro Ala Pro Gly Pro Glu Leu Ile
145                 150                 155                 160

Gln Gly Gly Thr Glu Val Thr Pro Gln Leu Leu Thr Phe Gly Glu Leu
                165                 170                 175

Ala Gly Ala Pro Ala Ala Thr Ala Thr Gly Gly Ala Ala Glu Thr Pro
            180                 185                 190

Ala Ala Ser Thr Pro Ala Ser Val Ala Val Ser Ser Thr Val Ala Pro
        195                 200                 205

Ala Thr Ser Ser Ala Ala Ala Glu Ala Glu Pro Ser Ser Val Ala Pro
    210                 215                 220

Val Glu Val Ser Thr Ala Val Glu Ser Ser Val Ala Ala Ser Ser Val
225                 230                 235                 240

Ala Ala Ser Ser Val Val Ala Ser Ser Val Ala Ala Ser Ser Val Ala
                245                 250                 255

Ala Ser Ser Ala Ala Ser Ser Ala Ala Ser Ser Ala Ala Ala Ala Pro
            260                 265                 270

Ala Glu Ser Glu Val Ala Pro Thr Pro Thr Pro Glu Val Ser Ser Val
        275                 280                 285

Val Ala Pro Tyr Pro Val Ala Asn Ser Thr Ser Ser Met Leu Pro Gly
290                 295                 300

Thr Ala Ser Pro Ile Val Thr Ser Ser Ile Val Ala Ala Pro Thr Thr
305                 310                 315                 320

Met Leu Thr Ala Val Arg Pro Thr Gln Thr Ala Glu Ala Ser Gly Pro
                325                 330                 335

Ile Lys Glu Tyr Tyr Gln Cys Ser Gly Gln Gly Phe Lys Gly Thr Gly
            340                 345                 350

Glu Cys Ala Glu Gly Leu Glu Cys Arg Glu Trp Asn Ser Trp Tyr Ser
        355                 360                 365

Gln Cys Val Lys Pro Glu Ala Thr Lys Leu Gly Pro Ser Lys Gly Pro
    370                 375                 380
```

```
Met Pro Ser Ser Ala Thr Ala Ser Lys Pro Thr Ala Thr Ala Val Ala
385                 390                 395                 400

Pro Lys Pro Thr Val Glu Ala Pro Lys Pro Thr Ala Glu Thr Pro Lys
                405                 410                 415

Pro Ser Pro Ala Glu Pro Thr Ser Ala Ala Ala Ala Ala Glu Ala
            420                 425                 430

Glu Pro Thr Ser Val Glu Pro Val Ala Val Glu Pro Ser Lys Pro Ala
            435                 440                 445

Thr Ser Ser Ala Pro Ala Ala Gly Ala Gly Glu Lys Thr Tyr Thr Leu
        450                 455                 460

Glu Thr Phe Ile Ala Phe Leu Glu Gln Glu Ala Gly Ser Glu Ser Ala
465                 470                 475                 480

Ala Lys Ile Arg Arg Met Ile Glu Ala Leu Gln
                485                 490

<210> SEQ ID NO 7
<211> LENGTH: 3135
<212> TYPE: DNA
<213> ORGANISM: Alternaria brassicicola

<400> SEQUENCE: 7
```

| | | | | | |
|---|---|---|---|---|---|
| atggcaccaa | atacaggtgc | cgttgacagc | accacagtga | ggtataaaag | gaccaagtcg | 60 |
| caatgggtcc | ccgaggatgt | ccaggcagca | cttgactggt | tcagcacaac | tatcatgtcg | 120 |
| cgctcaagct | ttctacaagt | ttcaacactg | ctctcctcct | ttctggcact | gacagcaggc | 180 |
| cagacacctg | tcagttcatc | cgatggcggt | tggagcacca | ctctggctgg | cacacctacc | 240 |
| gcgtttcgct | ccgtctttac | tctccctccc | tcagtggacc | agggcgttga | gcagatcccc | 300 |
| aacatctacg | atccgcaagc | tgtcaacgcg | caggatgtct | gcccaggcta | cagggcatcc | 360 |
| ggtcttgaac | aaggccatcg | tgggctgagc | gctaccttga | cgctggctgg | agctgcctgc | 420 |
| aatgcttacg | gcaccgatat | tgaagagctg | gacctgaagg | ttgaatatca | atcaaaggga | 480 |
| aggctggctg | tcagcattgt | acccaaacat | cttgatgcta | gcaaccagtc | ccaatggatt | 540 |
| gtgccccgagg | atctcatccc | gcggccgcaa | gccgaagact | cgtctgaggg | cacagacctc | 600 |
| aaatttgact | ggggcaacga | accatccttc | tggttcagtg | tcggccgtcg | ctctacggga | 660 |
| gatgtcatct | tcaccaccca | aggcacgaag | ctcatttatg | agaaccaatt | tgttgagttt | 720 |
| gtcaataacc | tgcccgagga | ctacaacctt | tacggtctcg | agaacgtat | tcacggactt | 780 |
| cgtctgaata | caacttcac | tgccaccatc | tatgctgccg | atgttggtga | cccaatcgac | 840 |
| cgcaatctgt | acggtagtca | ccccttctac | ctagaaacac | gctactttga | aaaaggcagc | 900 |
| aatggtagca | agacgcctct | gaagcagtct | gagctccaac | agcccaacct | ggctatgaa | 960 |
| agcaaaccag | ctggttcgcc | gtacgagtcg | cgctctcacg | gtgtgtacta | ccgcaacacg | 1020 |
| cacggcatgg | atgtcgttat | gaagcctgac | catctcacat | ggagaacatt | gggaggtgca | 1080 |
| atcgatctat | tcttctacga | aggaccctct | caaccagaag | tgaccaagga | gtaccagaag | 1140 |
| tcggcgattg | gactgcctgc | catgcaacag | tactggacat | tgggcttcca | tcaatgccga | 1200 |
| tggggatacc | gtaattggac | agagacgaga | gagattgttg | agactatgag | ggccttcaac | 1260 |
| attcccatgg | aaacaatttg | gctcgacatc | gattacatgg | atcaataccg | agacttcacg | 1320 |
| cttgatcccg | tgtcgtttcc | tccatcagat | gtcaaggact | tctttgactg | gctccatggg | 1380 |
| aacaaccagc | acttcgtacc | tatcgtggat | gccgccatct | acatcccgaa | cccacagaac | 1440 |
| gctagtgacg | cttatgatac | ctacgctcgc | ggaaatgaat | ctgatgtatt | cctgaggaat | 1500 |

-continued

```
cctgatggta gtcagtacat tggcgctgtg tggcctggat acaccgtctt cccagactgg   1560
ctgtcttcca acggtgtagc atggtgggtt aaggagatgg ttgagtggta caaggaagtg   1620
ccgtacagcg gtttctgggt cgatatgact gaagtctcct cgttctgcgt cggttcctgc   1680
ggttccggta atgttacctt gaaccctgct catccaccct tctccctccc tggcgaggtg   1740
ggcaacgtca ttttcgacta tccagaaggc ttcaacatca ccaacgcaac tgaggccgct   1800
tcggcttcag ccggcgcttc gagccaggcc gcaccggcag cgcctacgga ggaggctgct   1860
acgaccacta gctacttccg atcaacgcct acacctggtg tgcgcaacgt caactaccct   1920
ccatacgtca tcaaccatgt ccaatccgga gctgatcttg ctgtccacgc agtcagtcct   1980
aatgcaacac atcagaatgg cgttgaagag tacgatgtac acaaccttta tggtcaccag   2040
atcatcaatg ccacctacca gggtcttctt caagtctttc ctggaaagcg cccgtttatc   2100
atcggacgtt ccacctttgc tggtagcgga aagtgggccg gtcactgggg tggtgacaac   2160
gcgtccaagt gggcttatat gttcttttcg atccctcagg ctctgtcgtt ctcgcttttc   2220
ggtattccca tgttcggggc cgacacttgc ggattcaacg gcaacactaa tatggaactt   2280
tgcgctcgct ggatgcagct ttccgccttc ttccccttct accgcaacca caacgtgctt   2340
tctgccatcc cgcaggagcc ctaccgctgg gacgccgtag cttctgcatc caggaccgcg   2400
atgcacatcc gatactcgct actaccatac atgtacaccc tcttcaacga cgcccacacc   2460
accggctcga ccgtcatgcg tgcgctagcg tgggaatttc ccaatgagcc tcagctcgca   2520
ggtgttgaca cacagttcat gctgggtcct aacatcctaa ttactcctgt tcttgagccc   2580
caggtcgaca ctgttaatgg agtattccct ggtatcatcg acggcgaaag ctggttcgac   2640
tggtactctg gtgagcgcgt cgaggccgag gctggcgtca acaccaccat ctctgctcct   2700
ctgggtcaca tccccgtgta cattcgcggt ggctcagtac taccgatcca agaacctggt   2760
tacaccacga ctgagtcccg caagaaccca tggggtctca tcgttgcgct ttcagcggat   2820
ggtactgctt ccggtaacct gtacgtcgat gacggcgagt ctctcgagcc agaatcgtgc   2880
ttggatgtta cgttcgctgc tatgaatgga caactgaagg ccgatgttga gggaaagttc   2940
aaggacacga acgcgcttgc caacgtgacc attctgggtg ctccttcagt tggacaggtc   3000
aagttgaatg gcgagacaat cgatgcaagc aaggtgagct acaactctac tagcagcgtc   3060
ctgaagctgt caggcttgaa cgacttgact agtggaggag cttggcaggg aagctggact   3120
ctaagctggg agtaa                                                    3135
```

<210> SEQ ID NO 8
<211> LENGTH: 1044
<212> TYPE: PRT
<213> ORGANISM: Alternaria brassicicola

<400> SEQUENCE: 8

```
Met Ala Pro Asn Thr Gly Ala Val Asp Ser Thr Thr Val Arg Tyr Lys
1               5                   10                  15

Arg Thr Lys Ser Gln Trp Val Pro Glu Asp Val Gln Ala Ala Leu Asp
                20                  25                  30

Trp Phe Ser Thr Thr Ile Met Ser Arg Ser Ser Phe Leu Gln Val Ser
            35                  40                  45

Thr Leu Leu Ser Ser Phe Leu Ala Leu Thr Ala Gly Gln Thr Pro Val
        50                  55                  60

Ser Ser Ser Asp Gly Gly Trp Ser Thr Thr Leu Ala Gly Thr Pro Thr
65                  70                  75                  80

Ala Phe Arg Ser Val Phe Thr Leu Pro Pro Ser Val Asp Gln Gly Val
```

```
                85                      90                      95
Glu Gln Ile Pro Asn Ile Tyr Asp Pro Gln Ala Val Asn Ala Gln Asp
            100                     105                     110

Val Cys Pro Gly Tyr Arg Ala Ser Gly Leu Glu Gln Gly His Arg Gly
            115                     120                     125

Leu Ser Ala Thr Leu Thr Leu Ala Gly Ala Ala Cys Asn Ala Tyr Gly
            130                     135                     140

Thr Asp Ile Glu Glu Leu Asp Leu Lys Val Tyr Gln Ser Lys Gly
145                     150                     155                 160

Arg Leu Ala Val Ser Ile Val Pro Lys His Leu Asp Ala Ser Asn Gln
                165                     170                     175

Ser Gln Trp Ile Val Pro Glu Asp Leu Ile Pro Arg Pro Gln Ala Glu
            180                     185                     190

Asp Ser Ser Glu Gly Thr Asp Leu Lys Phe Asp Trp Gly Asn Glu Pro
            195                     200                     205

Ser Phe Trp Phe Ser Val Gly Arg Arg Ser Thr Gly Asp Val Ile Phe
            210                     215                     220

Thr Thr Gln Gly Thr Lys Leu Ile Tyr Glu Asn Gln Phe Val Glu Phe
225                     230                     235                 240

Val Asn Asn Leu Pro Glu Asp Tyr Asn Leu Tyr Gly Leu Gly Glu Arg
                245                     250                     255

Ile His Gly Leu Arg Leu Asn Asn Phe Thr Ala Thr Ile Tyr Ala
            260                     265                     270

Ala Asp Val Gly Asp Pro Ile Asp Arg Asn Leu Tyr Gly Ser His Pro
            275                     280                     285

Phe Tyr Leu Glu Thr Arg Tyr Phe Glu Lys Gly Ser Asn Gly Ser Lys
            290                     295                     300

Thr Pro Leu Lys Gln Ser Glu Leu Gln Gln Pro Asn Leu Gly Tyr Glu
305                     310                     315                 320

Ser Lys Pro Ala Gly Ser Pro Tyr Glu Ser Arg Ser His Gly Val Tyr
                325                     330                     335

Tyr Arg Asn Thr His Gly Met Asp Val Val Met Lys Pro Asp His Leu
            340                     345                     350

Thr Trp Arg Thr Leu Gly Gly Ala Ile Asp Leu Phe Phe Tyr Glu Gly
            355                     360                     365

Pro Ser Gln Pro Glu Val Thr Lys Glu Tyr Gln Lys Ser Ala Ile Gly
            370                     375                     380

Leu Pro Ala Met Gln Gln Tyr Trp Thr Leu Gly Phe His Gln Cys Arg
385                     390                     395                 400

Trp Gly Tyr Arg Asn Trp Thr Glu Thr Arg Glu Ile Val Glu Thr Met
                405                     410                     415

Arg Ala Phe Asn Ile Pro Met Glu Thr Ile Trp Leu Asp Ile Asp Tyr
            420                     425                     430

Met Asp Gln Tyr Arg Asp Phe Thr Leu Asp Pro Val Ser Phe Pro Pro
            435                     440                     445

Ser Asp Val Lys Asp Phe Phe Asp Trp Leu His Gly Asn Asn Gln His
            450                     455                     460

Phe Val Pro Ile Val Asp Ala Ala Ile Tyr Ile Pro Asn Pro Gln Asn
465                     470                     475                 480

Ala Ser Asp Ala Tyr Asp Thr Tyr Ala Arg Gly Asn Glu Ser Asp Val
                485                     490                     495

Phe Leu Arg Asn Pro Asp Gly Ser Gln Tyr Ile Gly Ala Val Trp Pro
            500                     505                     510
```

```
Gly Tyr Thr Val Phe Pro Asp Trp Leu Ser Ser Asn Gly Val Ala Trp
            515                 520                 525

Trp Val Lys Glu Met Val Glu Trp Tyr Lys Glu Val Pro Tyr Ser Gly
        530                 535                 540

Phe Trp Val Asp Met Thr Glu Val Ser Ser Phe Cys Val Gly Ser Cys
545                 550                 555                 560

Gly Ser Gly Asn Val Thr Leu Asn Pro Ala His Pro Pro Phe Ser Leu
                565                 570                 575

Pro Gly Glu Val Gly Asn Val Ile Phe Asp Tyr Pro Glu Gly Phe Asn
            580                 585                 590

Ile Thr Asn Ala Thr Glu Ala Ala Ser Ala Ser Ala Gly Ala Ser Ser
        595                 600                 605

Gln Ala Ala Pro Ala Ala Pro Thr Glu Glu Ala Ala Thr Thr Thr Ser
    610                 615                 620

Tyr Phe Arg Ser Thr Pro Thr Pro Gly Val Arg Asn Val Asn Tyr Pro
625                 630                 635                 640

Pro Tyr Val Ile Asn His Val Gln Ser Gly Ala Asp Leu Ala Val His
                645                 650                 655

Ala Val Ser Pro Asn Ala Thr His Gln Asn Gly Val Glu Glu Tyr Asp
            660                 665                 670

Val His Asn Leu Tyr Gly His Gln Ile Ile Asn Ala Thr Tyr Gln Gly
        675                 680                 685

Leu Leu Gln Val Phe Pro Gly Lys Arg Pro Phe Ile Ile Gly Arg Ser
    690                 695                 700

Thr Phe Ala Gly Ser Gly Lys Trp Ala Gly His Trp Gly Gly Asp Asn
705                 710                 715                 720

Ala Ser Lys Trp Ala Tyr Met Phe Phe Ser Ile Pro Gln Ala Leu Ser
                725                 730                 735

Phe Ser Leu Phe Gly Ile Pro Met Phe Gly Ala Asp Thr Cys Gly Phe
            740                 745                 750

Asn Gly Asn Thr Asn Met Glu Leu Cys Ala Arg Trp Met Gln Leu Ser
        755                 760                 765

Ala Phe Phe Pro Phe Tyr Arg Asn His Asn Val Leu Ser Ala Ile Pro
    770                 775                 780

Gln Glu Pro Tyr Arg Trp Asp Ala Val Ala Ser Ala Ser Arg Thr Ala
785                 790                 795                 800

Met His Ile Arg Tyr Ser Leu Leu Pro Tyr Met Tyr Thr Leu Phe Asn
                805                 810                 815

Asp Ala His Thr Thr Gly Ser Thr Val Met Arg Ala Leu Ala Trp Glu
            820                 825                 830

Phe Pro Asn Glu Pro Gln Leu Ala Gly Val Asp Thr Gln Phe Met Leu
        835                 840                 845

Gly Pro Asn Ile Leu Ile Thr Pro Val Leu Glu Pro Gln Val Asp Thr
    850                 855                 860

Val Asn Gly Val Phe Pro Gly Ile Ile Asp Gly Glu Ser Trp Phe Asp
865                 870                 875                 880

Trp Tyr Ser Gly Glu Arg Val Glu Ala Glu Ala Gly Val Asn Thr Thr
                885                 890                 895

Ile Ser Ala Pro Leu Gly His Ile Pro Val Tyr Ile Arg Gly Gly Ser
            900                 905                 910

Val Leu Pro Ile Gln Glu Pro Gly Tyr Thr Thr Thr Glu Ser Arg Lys
        915                 920                 925

Asn Pro Trp Gly Leu Ile Val Ala Leu Ser Ala Asp Gly Thr Ala Ser
    930                 935                 940
```

Gly Asn Leu Tyr Val Asp Asp Gly Glu Ser Leu Glu Pro Glu Ser Cys
945                 950                 955                 960

Leu Asp Val Thr Phe Ala Ala Met Asn Gly Gln Leu Lys Ala Asp Val
            965                 970                 975

Glu Gly Lys Phe Lys Asp Thr Asn Ala Leu Ala Asn Val Thr Ile Leu
            980                 985                 990

Gly Ala Pro Ser Val Gly Gln Val Lys Leu Asn Gly Glu Thr Ile Asp
        995                 1000                1005

Ala Ser Lys Val Ser Tyr Asn Ser Thr Ser Ser Val Leu Lys Leu Ser
    1010                1015                1020

Gly Leu Asn Asp Leu Thr Ser Gly Gly Ala Trp Gln Gly Ser Trp Thr
1025                1030                1035                1040

Leu Ser Trp Glu

<210> SEQ ID NO 9
<211> LENGTH: 1869
<212> TYPE: DNA
<213> ORGANISM: Alternaria brassicicola

<400> SEQUENCE: 9

| | | |
|---|---|---|
| atgaggtaca ctgccacctt cacaggtgta ctagccatcg ccggtgtcag cgcgtggtca | 60 |
| gtatccagtc ctttccatat tgagggcaac gaggttgtcg agcatctcca tacggtacca | 120 |
| gagggatgga gagaggttgg tgctccagcg cctgagcata agctgcattt ccgcattgca | 180 |
| gtgcgctcgg ccaaccgcga tgtatttgaa aggacgctca tggaggtttc gactcctagc | 240 |
| caccctcgct acggtcagca cctaaagcga gacgaactga agcatctcat caagcctaga | 300 |
| gccgactcga ctgcaagtgt gcttacctgg ctcgagcaat ccggtatcga agcgcgagac | 360 |
| atccagaacg acggcgagtg gatcaacttt ctcgcacccg tgaagcgcgc cgagcagatg | 420 |
| atgggtacca cgttcaagac ctaccagagt caagcgcgtc cagcgctcaa gagaactcgc | 480 |
| tcgttggggt actctgtgcc cttggacgtc cgcagtcata ttgatatgat ccagcctacc | 540 |
| actcgcttcg gtgaaatccg ccccgagttc agccaagtcc ttacgcaaaa gaccgctccc | 600 |
| ttctcggtgc ttgctgtcaa tgccacgtgc aacacaagga tcacgcccga ttgtctcgca | 660 |
| gatctgtaca acttcaagga ttacaacgtt agtgacaaag ccgatgtgac aatcggggtg | 720 |
| agcggcttcc tcgagcagta cgcccggttc aacgatctcg accagttcat ccaaagattt | 780 |
| gctcccagcc ttgcgggtaa aacgttcaaa gtccagtcta tcaatggtaa gatgcagtca | 840 |
| tgttacctc gctatcttca gctaacgttc gtagacgggc cgttccctca aaactcaacg | 900 |
| gccaacagcg ttgaggctaa cctcgacatc agtatacag ctggtctggt gtcgcctaag | 960 |
| atttcaacca ctttctacac tgttccagga cgaggactgt tggtccccga ccttgaccaa | 1020 |
| cctgatctcg aggacgagga gctgcctgaa gtactgacga cgtcgtacgg tgagacggag | 1080 |
| cagagcgttc ctgcggagta tgccaagaag gtttgtgaca tgatcggcca gctcggtact | 1140 |
| cgtggtgtct cggtcatctt cgaggatgaa tccaccacag ccagcggtga tactggtcca | 1200 |
| ggctctgcct gtcagagcaa tgacggcaag aacgctaccc gtcttcaacc aatcttccca | 1260 |
| gcttcatgcc cctacgttac ttcagtcggt ggcacgtttg gagtggaacc cgaacgtgct | 1320 |
| gttgagttct cttctggtgg cttctctgat ctctggtctc gcccggcgta ccaagagaag | 1380 |
| gcagtgactg actaccttgg caaactgggc tcgcaatggc aaggtttgta caacgccaac | 1440 |
| ggacgaggt ttccagatgt cgcggctcaa ggaaagggat tcaggtcat tgataagctt | 1500 |
| ggcttgtcgt ctgttggagg aaccagcgcc tcagcgcctg tcttcgcttc ggtcattgcg | 1560 |

```
cttctgaaca acgctcgttt ggcggctggt atgccttcgc tgggcttctt gaacccttgg    1620
atctacgagc aaggctacaa gggcatgaat gatattgtcg agggaggctc cgcggatgc     1680 actggtcgct ctatctattc cgggcttccc acgcgactcg tgccttacgc ctcctggaat    1740
gcgaccgagg gctgggatcc cgtcaccggt tacggtacac ccgactttga gcagatgctt    1800
cgcctctcga ctacgccgca atacggtgcg cgtcgcgttc ggcgtggtag cctccgtgga    1860
gaggcttag                                                           1869
```

<210> SEQ ID NO 10
<211> LENGTH: 622
<212> TYPE: PRT
<213> ORGANISM: Alternaria brassicicola

<400> SEQUENCE: 10

```
Met Arg Tyr Thr Ala Thr Phe Thr Gly Val Leu Ala Ile Ala Gly Val
1               5                   10                  15

Ser Ala Trp Ser Val Ser Ser Pro Phe His Ile Glu Gly Asn Glu Val
            20                  25                  30

Val Glu His Leu His Thr Val Pro Glu Gly Trp Arg Glu Val Gly Ala
        35                  40                  45

Pro Ala Pro Glu His Lys Leu His Phe Arg Ile Ala Val Arg Ser Ala
    50                  55                  60

Asn Arg Asp Val Phe Glu Arg Thr Leu Met Glu Val Ser Thr Pro Ser
65                  70                  75                  80

His Pro Arg Tyr Gly Gln His Leu Lys Arg Asp Glu Leu Lys His Leu
                85                  90                  95

Ile Lys Pro Arg Ala Asp Ser Thr Ala Ser Val Leu Thr Trp Leu Glu
            100                 105                 110

Gln Ser Gly Ile Glu Ala Arg Asp Ile Gln Asn Asp Gly Glu Trp Ile
        115                 120                 125

Asn Phe Leu Ala Pro Val Lys Arg Ala Glu Gln Met Met Gly Thr Thr
130                 135                 140

Phe Lys Thr Tyr Gln Ser Gln Ala Arg Pro Ala Leu Lys Arg Thr Arg
145                 150                 155                 160

Ser Leu Gly Tyr Ser Val Pro Leu Asp Val Arg Ser His Ile Asp Met
                165                 170                 175

Ile Gln Pro Thr Thr Arg Phe Gly Glu Ile Arg Pro Glu Phe Ser Gln
            180                 185                 190

Val Leu Thr Gln Lys Thr Ala Pro Phe Ser Val Leu Ala Val Asn Ala
        195                 200                 205

Thr Cys Asn Thr Arg Ile Thr Pro Asp Cys Leu Ala Asp Leu Tyr Asn
    210                 215                 220

Phe Lys Asp Tyr Asn Val Ser Asp Lys Ala Asp Val Thr Ile Gly Val
225                 230                 235                 240

Ser Gly Phe Leu Glu Gln Tyr Ala Arg Phe Asn Asp Leu Asp Gln Phe
                245                 250                 255

Ile Gln Arg Phe Ala Pro Ser Leu Ala Gly Lys Thr Phe Lys Val Gln
            260                 265                 270

Ser Ile Asn Gly Lys Met Gln Ser Leu Leu Pro Arg Tyr Leu Gln Leu
        275                 280                 285

Thr Phe Val Asp Gly Pro Phe Pro Gln Asn Ser Thr Ala Asn Ser Val
    290                 295                 300

Glu Ala Asn Leu Asp Ile Gln Tyr Thr Ala Gly Leu Val Ser Pro Lys
305                 310                 315                 320
```

```
Ile Ser Thr Thr Phe Tyr Thr Val Pro Gly Arg Gly Leu Leu Val Pro
            325                 330                 335

Asp Leu Asp Gln Pro Asp Leu Glu Asp Glu Leu Pro Glu Val Leu
            340                 345                 350

Thr Thr Ser Tyr Gly Glu Thr Glu Gln Ser Val Pro Ala Glu Tyr Ala
            355                 360                 365

Lys Lys Val Cys Asp Met Ile Gly Gln Leu Gly Thr Arg Gly Val Ser
            370                 375                 380

Val Ile Phe Glu Asp Glu Ser Thr Thr Ala Ser Gly Asp Thr Gly Pro
385                 390                 395                 400

Gly Ser Ala Cys Gln Ser Asn Asp Gly Lys Asn Ala Thr Arg Leu Gln
            405                 410                 415

Pro Ile Phe Pro Ala Ser Cys Pro Tyr Val Thr Ser Val Gly Gly Thr
            420                 425                 430

Phe Gly Val Glu Pro Glu Arg Ala Val Glu Phe Ser Ser Gly Gly Phe
            435                 440                 445

Ser Asp Leu Trp Ser Arg Pro Ala Tyr Gln Glu Lys Ala Val Thr Asp
            450                 455                 460

Tyr Leu Gly Lys Leu Gly Ser Gln Trp Gln Gly Leu Tyr Asn Ala Asn
465                 470                 475                 480

Gly Arg Gly Phe Pro Asp Val Ala Ala Gln Lys Gly Phe Gln Val
            485                 490                 495

Ile Asp Lys Leu Gly Leu Ser Ser Val Gly Gly Thr Ser Ala Ser Ala
            500                 505                 510

Pro Val Phe Ala Ser Val Ile Ala Leu Leu Asn Asn Ala Arg Leu Ala
            515                 520                 525

Ala Gly Met Pro Ser Leu Gly Phe Leu Asn Pro Trp Ile Tyr Glu Gln
            530                 535                 540

Gly Tyr Lys Gly Met Asn Asp Ile Val Glu Gly Ser Arg Gly Cys
545                 550                 555                 560

Thr Gly Arg Ser Ile Tyr Ser Gly Leu Pro Thr Arg Leu Val Pro Tyr
            565                 570                 575

Ala Ser Trp Asn Ala Thr Glu Gly Trp Asp Pro Val Thr Gly Tyr Gly
            580                 585                 590

Thr Pro Asp Phe Glu Gln Met Leu Arg Leu Ser Thr Thr Pro Gln Tyr
            595                 600                 605

Gly Ala Arg Arg Val Arg Arg Gly Ser Leu Arg Gly Glu Ala
    610                 615                 620

<210> SEQ ID NO 11
<211> LENGTH: 1782
<212> TYPE: DNA
<213> ORGANISM: Alternaria brassicicola

<400> SEQUENCE: 11
atggctcctg tgctctcgtt catcgttggc tcgctgttgg ccttgcaggc cttcgccgag      60
ccattcgaaa agcttttcga tgtcccagag ggatggaagc tccaaggccc tgcatcggct     120
gcgcacacgc tcaagctcca ggtcgcgctc cagcaaggcg ataccgccgg ctttgagcag     180
accgtcatgg aaatgtccac ccctccaat gcaaagtacg gcagcacttt gagtcccac      240 gagcaaatga agcgcatgct catgcccagt gaggagaccg tttcctccgt ctcttcctgg     300
ctcaaggctg ccggtatcaa gaactttgag attgacgccg attgggtgac cttcaagaca     360
accgttggtg ttgccaacga gctcctcaga accaagttct cctggtttgt cagcgaggag     420
```

```
agtacgcctc gcaaagttct ccgcacgctc gagtactctg tgcccgacga cattgccgac    480
cacatcaacc tcgttcagcc gaccactcga ttcgctgcta ccgtgcgaa ccacgagaca    540 gagcgcgaga tcttcggtat tgcgctagcc tcttccccca acgtcactgt caactgtgat    600
gcgtccatca ctccccagtg cttgaagcag ctctacaaga ttgactacac tcccgacccc    660
aagagtggca gtaaggcagc tttcgcttcc tatctcgagg agtacgcgcg ctacagcgac    720
ctcgccctct tcgaggagaa cgtcctcccc gaggctgtgg ccagaacttt ctccgttgtt    780
caattcaacg gcggcttgaa cgaccaagcc tctgccgacg acagtggcga ggccaacttg    840
gatttgcagt acatgctcgg tcttgcccag cccctgcctg ttattgagta tagcactggt    900
ggacgtggcc catggatcgc tgacctcgac cagcctgacg aggctgacag cgccaacgag    960
ccctacctcg agttccttca gtcggtgctc aagctcccac agagcgatct tccccaggtc   1020
atctccacgt cttacggcga aacgaacaa agcgtaccca agtcttacgc tctcagcgtc   1080
tgcaacctct tcgctcaact tggtagccgt ggtgtctctg tcatcttctc atctggtgat   1140
tccggtaccg gatccgcctg ccttttccaac gacggcaaga acactaccaa gttccagcct   1200
cagtaccccg ctgcctgccc attcgtcacc tccgtcgggt caactcgcta cctcaacgag   1260
actgccactt tcttctcctc tggtggttttc tccgactact ggaagcgccc cagctaccag   1320
gatgatgccg tcaaggcata cttgcatcaa ctcggccaga gaacaagcc ctacttcaac   1380 cgccacgggc gcggattccc ggacgtctcg gcccagggct ccggttacag ggtctacgac   1440
aagggttctc tcaaggggta ccagggtact tcatgctccg ctcccgcttt cggcggtatc   1500
gtcgctctcc tcaatgacgc gcgtctgagg gccaagaagc ctgctcttgg tttcctgaac   1560
cccctgcttt actccaaccc ggatgcgctc aacgatatcg ttcttggtgg cagcacagga   1620
tgtgatggcc acgcgcgctt caatggcaag ccgaacggta gccctgttat cccgtacgcg   1680
agctggaacg ccactgcggg atgggaccca gtttccggat tgggcacgcc aaacttcccc   1740
aagttgctca aggctgctct tcccgctagg tacaaggctt ag                      1782
```

<210> SEQ ID NO 12
<211> LENGTH: 593
<212> TYPE: PRT
<213> ORGANISM: Alternaria brassicicola

<400> SEQUENCE: 12

```
Met Ala Pro Val Leu Ser Phe Ile Val Gly Ser Leu Leu Ala Leu Gln
1               5                   10                  15

Ala Phe Ala Glu Pro Phe Glu Lys Leu Phe Asp Val Pro Glu Gly Trp
            20                  25                  30

Lys Leu Gln Gly Pro Ala Ser Ala Ala His Thr Leu Lys Leu Gln Val
        35                  40                  45

Ala Leu Gln Gln Gly Asp Thr Ala Gly Phe Glu Gln Thr Val Met Glu
    50                  55                  60

Met Ser Thr Pro Ser Asn Ala Lys Tyr Gly Gln His Phe Glu Ser His
65                  70                  75                  80

Glu Gln Met Lys Arg Met Leu Met Pro Ser Glu Thr Val Ser Ser
            85                  90                  95

Val Ser Ser Trp Leu Lys Ala Ala Gly Ile Lys Asn Phe Glu Ile Asp
            100                 105                 110

Ala Asp Trp Val Thr Phe Lys Thr Thr Val Gly Val Ala Asn Glu Leu
        115                 120                 125

Leu Arg Thr Lys Phe Ser Trp Phe Val Ser Glu Glu Ser Thr Pro Arg
    130                 135                 140
```

```
Lys Val Leu Arg Thr Leu Glu Tyr Ser Val Pro Asp Ile Ala Asp
145                 150                 155                 160

His Ile Asn Leu Val Gln Pro Thr Thr Arg Phe Ala Ala Ile Arg Ala
            165                 170                 175

Asn His Glu Thr Glu Arg Glu Ile Phe Gly Ile Ala Leu Ala Ser Ser
        180                 185                 190

Pro Asn Val Thr Val Asn Cys Asp Ala Ser Ile Thr Pro Gln Cys Leu
        195                 200                 205

Lys Gln Leu Tyr Lys Ile Asp Tyr Thr Pro Asp Pro Lys Ser Gly Ser
210                 215                 220

Lys Ala Ala Phe Ala Ser Tyr Leu Glu Glu Tyr Ala Arg Tyr Ser Asp
225                 230                 235                 240

Leu Ala Leu Phe Glu Glu Asn Val Leu Pro Glu Ala Val Gly Gln Asn
                245                 250                 255

Phe Ser Val Val Gln Phe Asn Gly Gly Leu Asn Asp Gln Ala Ser Ala
            260                 265                 270

Asp Asp Ser Gly Glu Ala Asn Leu Asp Leu Gln Tyr Met Leu Gly Leu
        275                 280                 285

Ala Gln Pro Leu Pro Val Ile Glu Tyr Ser Thr Gly Gly Arg Gly Pro
290                 295                 300

Trp Ile Ala Asp Leu Asp Gln Pro Asp Glu Ala Asp Ser Ala Asn Glu
305                 310                 315                 320

Pro Tyr Leu Glu Phe Leu Gln Ser Val Leu Lys Leu Pro Gln Ser Asp
                325                 330                 335

Leu Pro Gln Val Ile Ser Thr Ser Tyr Gly Glu Asn Glu Gln Ser Val
            340                 345                 350

Pro Lys Ser Tyr Ala Leu Ser Val Cys Asn Leu Phe Ala Gln Leu Gly
        355                 360                 365

Ser Arg Gly Val Ser Val Ile Phe Ser Ser Gly Asp Ser Gly Thr Gly
370                 375                 380

Ser Ala Cys Leu Ser Asn Asp Gly Lys Asn Thr Thr Lys Phe Gln Pro
385                 390                 395                 400

Gln Tyr Pro Ala Ala Cys Pro Phe Val Thr Ser Val Gly Ser Thr Arg
                405                 410                 415

Tyr Leu Asn Glu Thr Ala Thr Phe Phe Ser Ser Gly Gly Phe Ser Asp
            420                 425                 430

Tyr Trp Lys Arg Pro Ser Tyr Gln Asp Asp Ala Val Lys Ala Tyr Leu
        435                 440                 445

His Gln Leu Gly Gln Lys Asn Lys Pro Tyr Phe Asn Arg His Gly Arg
450                 455                 460

Gly Phe Pro Asp Val Ser Ala Gln Gly Ser Gly Tyr Arg Val Tyr Asp
465                 470                 475                 480

Lys Gly Ser Leu Lys Gly Tyr Gln Gly Thr Ser Cys Ser Ala Pro Ala
                485                 490                 495

Phe Gly Gly Ile Val Ala Leu Leu Asn Asp Ala Arg Leu Arg Ala Lys
            500                 505                 510

Lys Pro Ala Leu Gly Phe Leu Asn Pro Leu Leu Tyr Ser Asn Pro Asp
        515                 520                 525

Ala Leu Asn Asp Ile Val Leu Gly Gly Ser Thr Gly Cys Asp Gly His
530                 535                 540

Ala Arg Phe Asn Gly Lys Pro Asn Gly Ser Pro Val Ile Pro Tyr Ala
545                 550                 555                 560

Ser Trp Asn Ala Thr Ala Gly Trp Asp Pro Val Ser Gly Leu Gly Thr
```

```
                565                 570                 575
Pro Asn Phe Pro Lys Leu Leu Lys Ala Ala Leu Pro Arg Tyr Lys
        580                 585                 590

Ala

<210> SEQ ID NO 13
<211> LENGTH: 1112
<212> TYPE: DNA
<213> ORGANISM: Alternaria brassicicola

<400> SEQUENCE: 13
atgtttgcca aaactactct catgagcgcg ctgctcagcg ctgcactgcc gaggtcatct     60
gggacggtcg cttcaacgac atgacctcct ctaccgaact ctccgactgg tccttctcca    120
accccgtcgg cagctaccaa tactacatcc acggtcctgg ctccgtaact gactacgtaa    180
acctcggcgc caccttcaag aaccccgccg acacagcttc caagcaaggt gtcaagatca    240
ccatcgacga gactgcgaaa tggaacggcc aaaccatgct gcgcaccgaa ctcatcccag    300
agaccaaggc cgccatcaac aagggcaaag tctactacca cttctccgtc aagacaacgg    360
ctgagaacgc cgccgaccgcc accaacgaac caagtcgc tttcttcgag agccacttca    420
ccgagttgaa gtatggcgct tctggttctt cgaacaccaa cctacaatgg cacgttggtg    480
gcgtctccaa gtgggacgtt gagctcgtag ccgatgagtg cacaacgtt gcctacgaaa    540 tcgactttga tgccggttcc gtcgcattct ggcactccac cggtgctgat gagctcaagc    600
agacagctgg tccgttcgat gctagcacct cttctaacgg tgcggactgg catcttggtg    660
tgctgaggct gccgggtaac gccgacaagg atggtgctga ggattggttc ttcagcggtg    720
ttggtagtgg agctgctggt gcggccccag aaaagcctgt tgccagtgct gctgcaccatt    780 ccaatgtcgt ttcttctgct gctcctgctg ctactacttc caaggctgct gtcgccccgg    840
tctcctccag cgctgcggct gtcgagactt ctgtcgtatc ctccactgct gctgcttctt    900
ccactgcagt ccctgctgag accccggctg tctcttctgc tgctgctatt ccagcgctg    960 ctcccgtcga ctcccgcc gcctcttcta cctctgctgt cactcccgtt gctacaccta   1020
ctgctgtggc cggtctgac gccaagctcc ccgaggagtt caccatcagc caattcgtcg   1080
cttggctcaa ggctaagact ggcaagaact aa                                1112

<210> SEQ ID NO 14
<211> LENGTH: 370
<212> TYPE: PRT
<213> ORGANISM: Alternaria brassicicola

<400> SEQUENCE: 14

Met Phe Ala Lys Thr Thr Leu Met Ser Ala Leu Leu Ser Ala Ala Ser
1               5                   10                  15

Ala Glu Val Ile Trp Asp Gly Arg Phe Asn Asp Met Thr Ser Ser Thr
            20                  25                  30

Glu Leu Ser Asp Trp Ser Phe Ser Asn Pro Val Gly Ser Tyr Gln Tyr
        35                  40                  45

Tyr Ile His Gly Pro Gly Ser Val Thr Asp Tyr Val Asn Leu Gly Ala
    50                  55                  60

Thr Phe Lys Asn Pro Ala Asp Thr Ala Ser Lys Gln Gly Val Lys Ile
65                  70                  75                  80

Thr Ile Asp Glu Thr Ala Lys Trp Asn Gly Gln Thr Met Leu Arg Thr
                85                  90                  95

Glu Leu Ile Pro Glu Thr Lys Ala Ala Ile Asn Lys Gly Lys Val Tyr
```

```
                    100                 105                 110
Tyr His Phe Ser Val Lys Thr Thr Ala Glu Asn Ala Pro Thr Ala Thr
                115                 120                 125

Asn Glu His Gln Val Ala Phe Phe Glu Ser His Phe Thr Glu Leu Lys
            130                 135                 140

Tyr Gly Ala Ser Gly Ser Ser Asn Thr Asn Leu Gln Trp His Val Gly
145                 150                 155                 160

Gly Val Ser Lys Trp Asp Val Glu Leu Val Ala Asp Glu Trp His Asn
                165                 170                 175

Val Ala Tyr Glu Ile Asp Phe Asp Ala Gly Ser Val Ala Phe Trp His
            180                 185                 190

Ser Thr Gly Ala Asp Glu Leu Lys Gln Thr Ala Gly Pro Phe Asp Ala
                195                 200                 205

Ser Thr Ser Ser Asn Gly Ala Asp Trp His Leu Gly Val Leu Arg Leu
    210                 215                 220

Pro Gly Asn Ala Asp Lys Asp Gly Ala Glu Asp Trp Phe Phe Ser Gly
225                 230                 235                 240

Val Gly Ser Gly Ala Gly Ala Ala Pro Glu Lys Pro Val Ala Ser
                245                 250                 255

Ala Ala Ala Pro Ser Asn Val Val Ser Ser Ala Ala Pro Ala Ala Thr
                260                 265                 270

Thr Ser Lys Ala Ala Val Ala Pro Val Ser Ser Ser Ala Ala Val
                275                 280                 285

Glu Thr Ser Val Val Ser Ser Thr Ala Ala Ser Ser Thr Ala Val
    290                 295                 300

Pro Ala Glu Thr Pro Ala Val Ser Ser Ala Ala Ile Ser Ser Ala
305                 310                 315                 320

Ala Pro Val Glu Thr Pro Ala Ala Ser Ser Thr Ser Ala Val Thr Pro
                325                 330                 335

Val Ala Thr Pro Thr Ala Val Ala Gly Ser Asp Ala Lys Leu Pro Glu
                340                 345                 350

Glu Phe Thr Ile Ser Gln Phe Val Ala Trp Leu Lys Ala Lys Thr Gly
            355                 360                 365

Lys Asn
    370

<210> SEQ ID NO 15
<211> LENGTH: 336
<212> TYPE: DNA
<213> ORGANISM: Alternaria brassicicola

<400> SEQUENCE: 15
atgtctacct ccgagctcgc cacctcttac gccgctctca tcctcgctga tgacggtgtc      60
gacatcactg ccgacaagct ccagtctctc atcaaggccg caaagatcga ggaggtcgag     120
cccatctgga cgaccctgtt cgccaaggct cttgagggca aggatgtcaa ggacctgcta     180
ctgaacgtcg gctcaggcgg cggcgctgcc cctgctgccg gaggcgctgc ccctgctgct     240
ggcggtgctg ctgaggccgc accagctgcc gaggagaaga aggaggagga aaggaggag      300 tcagacgagg acatgggctt cggtctcttc gactaa                              336

<210> SEQ ID NO 16
<211> LENGTH: 111
<212> TYPE: PRT
<213> ORGANISM: Alternaria brassicicola

<400> SEQUENCE: 16
```

```
Met Ser Thr Ser Glu Leu Ala Thr Ser Tyr Ala Ala Leu Ile Leu Ala
1               5                   10                  15

Asp Asp Gly Val Asp Ile Thr Ala Asp Lys Leu Gln Ser Leu Ile Lys
            20                  25                  30

Ala Ala Lys Ile Glu Glu Val Glu Pro Ile Trp Thr Thr Leu Phe Ala
            35                  40                  45

Lys Ala Leu Glu Gly Lys Asp Val Lys Asp Leu Leu Leu Asn Val Gly
50                  55                  60

Ser Gly Gly Gly Ala Ala Pro Ala Ala Gly Ala Ala Pro Ala Ala
65                  70                  75                  80

Gly Gly Ala Ala Glu Ala Ala Pro Ala Ala Glu Lys Lys Glu Glu
                85                  90                  95

Glu Lys Glu Glu Ser Asp Glu Asp Met Gly Phe Gly Leu Phe Asp
                100                 105                 110
```

<210> SEQ ID NO 17
<211> LENGTH: 654
<212> TYPE: DNA
<213> ORGANISM: Alternaria brassicicola

<400> SEQUENCE: 17

```
atggctgcac ctcagtacac cctgcctccg ctgccatatg catacaatgc attggagccg      60
cacatctcag cacagatcat ggagctgcac acagcaagc accaccagac gtatatcacc     120
aacttgaatg gtcttctcaa gactcaagcc gaagccgttt ctacctccga catcacttca     180
caggtttcga tacagcaagg catcaagttc aacgctggcg gccacatcaa ccactctctc     240
ttctggcaaa acctcgctcc tgccagctcg ggtgaggctc agagctccgc tgctcctgag     300
ctactcaaac agatcaaggc gacttgggga acgaggata agttcaagga agccttcaac      360
acagctttgc taggcatcca aggaagtggt tggggatggt tggtcaagac cgatataggc     420
aaggagcaga gattgtctat cgtgacgacc aaggaccagg atcctgttgt tggtaaaggc     480
gaagttccga tcttcggtgt tgacatgtgg gagcatgcgt actatctcca gtaccagaat     540
ggtaaggctg cttacgtcaa gaatatctgg aatgtcatta actggaagac ggcggaggag     600
cgttatctgg atcgcgcgc agatgctttc agtgtgctga gggcatccat ctaa            654
```

<210> SEQ ID NO 18
<211> LENGTH: 217
<212> TYPE: PRT
<213> ORGANISM: Alternaria brassicicola

<400> SEQUENCE: 18

```
Met Ala Ala Pro Gln Tyr Thr Leu Pro Pro Leu Pro Tyr Ala Tyr Asn
1               5                   10                  15

Ala Leu Glu Pro His Ile Ser Ala Gln Ile Met Glu Leu His His Ser
            20                  25                  30

Lys His His Gln Thr Tyr Ile Thr Asn Leu Asn Gly Leu Leu Lys Thr
        35                  40                  45

Gln Ala Glu Ala Val Ser Thr Ser Asp Ile Thr Ser Gln Val Ser Ile
50                  55                  60

Gln Gln Gly Ile Lys Phe Asn Ala Gly Gly His Ile Asn His Ser Leu
65                  70                  75                  80

Phe Trp Gln Asn Leu Ala Pro Ala Ser Ser Gly Glu Ala Gln Ser Ser
                85                  90                  95

Ala Ala Pro Glu Leu Leu Lys Gln Ile Lys Ala Thr Trp Gly Asp Glu
                100                 105                 110
```

```
Asp Lys Phe Lys Glu Ala Phe Asn Thr Ala Leu Leu Gly Ile Gln Gly
        115                 120                 125

Ser Gly Trp Gly Trp Leu Val Lys Thr Asp Ile Gly Lys Glu Gln Arg
130                 135                 140

Leu Ser Ile Val Thr Thr Lys Asp Gln Asp Pro Val Val Gly Lys Gly
145                 150                 155                 160

Glu Val Pro Ile Phe Gly Val Asp Met Trp Glu His Ala Tyr Tyr Leu
                165                 170                 175

Gln Tyr Gln Asn Gly Lys Ala Ala Tyr Val Lys Asn Ile Trp Asn Val
            180                 185                 190

Ile Asn Trp Lys Thr Ala Glu Glu Arg Tyr Leu Gly Ser Arg Ala Asp
        195                 200                 205

Ala Phe Ser Val Leu Arg Ala Ser Ile
        210                 215

<210> SEQ ID NO 19
<211> LENGTH: 771
<212> TYPE: DNA
<213> ORGANISM: Alternaria brassicicola

<400> SEQUENCE: 19
atgggcgtga tgagtgaaaa ggttgccagc tgtatcgacg agattgagga atccactctc      60
agcaccgagg gcaaggtcca agcccagact gttattacgg aagagcttaa aaagctgctc     120
aagcactgtg cgaatgcaac agattgcgtc tatacggctc tcgacttgct tcgtaactcg     180
ctgcatatca atgagtctaa tcagggccct gacatgagca tcattaaaga gctgatcgcg     240
gagaacgcgg tccggttgag cacgccacgc aagagctggt tatggggtgt cgcaaaagtc     300
gtgcttggag cagtaacgag tgcaactatc gctatcgcgg cggcgtacct ttatggtacc     360
aacgattttg gtttggcacc gcagactaac accaacagca tgcacccccca ggtcatttcc     420 ctcgtccagc gcgcccaagc ggtgaccaac ctcacaggcg aaatccactc catcaaactt     480
gagcatctag accgccgcta ccaggagctc gaaggcgcct ctgaatctca cggtctccga     540
atcgacaacc tggtcgaagc actgggtgct cccaatgcag acggcaccta ctattcatct     600
atgccgaaac ctgactgcca acctcctagc gatatcccga tgatctacgc aaaccccgat     660
cgccagattg aacgactgcg cagcgagctg cagaccatgc gtaagaatat tcatcgcatg     720
gacattcgcc tcatgaagcg tctcaataag atcgaccaac gtggtctgtg a             771

<210> SEQ ID NO 20
<211> LENGTH: 256
<212> TYPE: PRT
<213> ORGANISM: Alternaria brassicicola

<400> SEQUENCE: 20

Met Gly Val Met Ser Glu Lys Val Ala Ser Cys Ile Asp Glu Ile Glu
1               5                   10                  15

Glu Ser Thr Leu Ser Thr Glu Gly Lys Val Gln Ala Gln Thr Val Ile
            20                  25                  30

Thr Glu Glu Leu Lys Lys Leu Leu Lys His Cys Ala Asn Ala Thr Asp
        35                  40                  45

Cys Val Tyr Thr Ala Leu Asp Leu Leu Arg Asn Ser Leu His Ile Asn
    50                  55                  60

Glu Ser Asn Gln Gly Pro Asp Met Ser Ile Ile Lys Glu Leu Ile Ala
65                  70                  75                  80

Glu Asn Ala Val Arg Leu Ser Thr Pro Arg Lys Ser Trp Leu Trp Gly
```

```
                    85                  90                  95
Val Ala Lys Val Val Leu Gly Ala Val Thr Ser Ala Thr Ile Ala Ile
            100                 105                 110

Ala Ala Ala Tyr Leu Tyr Gly Thr Asn Asp Phe Gly Leu Ala Pro Gln
            115                 120                 125

Thr Asn Thr Asn Ser Met His Pro Gln Val Ile Ser Leu Val Gln Arg
        130                 135                 140

Ala Gln Ala Val Thr Asn Leu Thr Gly Glu Ile His Ser Ile Lys Leu
145                 150                 155                 160

Glu His Leu Asp Arg Arg Tyr Gln Glu Leu Glu Gly Ala Ser Glu Ser
                165                 170                 175

His Gly Leu Arg Ile Asp Asn Leu Val Glu Ala Leu Gly Ala Pro Asn
            180                 185                 190

Ala Asp Gly Thr Tyr Tyr Ser Ser Met Pro Lys Pro Asp Cys Gln Pro
            195                 200                 205

Pro Ser Asp Ile Pro Met Ile Tyr Ala Asn Pro Asp Arg Gln Ile Glu
        210                 215                 220

Arg Leu Arg Ser Glu Leu Gln Thr Met Arg Lys Asn Ile His Arg Met
225                 230                 235                 240

Asp Ile Arg Leu Met Lys Arg Leu Asn Lys Ile Asp Gln Arg Gly Leu
                245                 250                 255

<210> SEQ ID NO 21
<211> LENGTH: 1280
<212> TYPE: DNA
<213> ORGANISM: Alternaria brassicicola

<400> SEQUENCE: 21
atgacaacct tcctcctccg cgatatccgc atctttaccg gcgagggggac catcgacaaa     60 gggtatattc acgttcaaaa tggcaagata aaggctatcg ccagataag cgaggctccg     120 ctggactcag taaagacata ctctaaacca ggtcatacga ttcttccagg gttgattgac    180
tgtcacatcc atgccgacag gccgatcct gaagctctac cccaagccct gcgctttggt    240
gtgactaccg tttgcgagat gcacaacgag ctggagaacg tacaaaagct gaagaagcag    300
accatggagc ccgatactgc ttcatacaag acagcaggcc aggccgctac tattgagaat    360
gggtggccta tacccgtcat cacggcccac gacaagactc cagagactgc agcggcgatt    420
gcgaaatggc caaaactgac ggatcgggat agcgtggtgg agttcctgga tggactggg    480 agagagatgc aaccaaatta catcaaactc atgcacgaaa gcggaactat catgggacgc    540
aattttagct atccttcgtt cgaactgcaa agtacgatca ttgcagaagc caaaaaacgg    600
ggatacttga ccgtcgcgca cgctctaagt atgcgtgaca cgctcgaggt tctgaatgca    660
ggtgtcgacg gccttacgca tacgtttttc gaccagccgc caacccagga actagtagat    720
gcgtacaaaa agaacaacgc atgggtcaac ccgacacttg ttgcgatagg cagcctgacg    780
accgagggaa aagagctgca gcatcaattt gcacacgatc ccagggtgaa agggttgatc    840
aaggaagatc gtgtaggcaa catgtgcaag tgcatgggct ttgctgcaga gggagggaaa    900
gtagaatacg catatcaagg cgtgaaaggg ctgagagaag cgggcatcga catcctgtgt    960
gggagcgact ccgcgggtcc ggcagtaggg acggcatttg gtctatcgat gcatcacgaa   1020
ttgtatctcc tcgtaaataa ggtgggaatg acacctatag aggctttacg ctcagccaca   1080
agcctgaccg cgaagcgctt ccaatttagg gatcgtggtc gtctggcgga agggctcaac   1140
gccgatttgt tactggtaga aggaaatccg cttgaagaca ttgatgcgac gctaaatatc   1200
```

```
cgcggcgttt ggcgggatgg caacctttgt agcacgttgt tgaaaagctt ggagctggtg    1260
ttgagcctct attgagttga                                                1280
```

```
<210> SEQ ID NO 22
<211> LENGTH: 426
<212> TYPE: PRT
<213> ORGANISM: Alternaria brassicicola

<400> SEQUENCE: 22
```

| | | | | | | | | | | | | | | | |
|---|---|---|---|---|---|---|---|---|---|---|---|---|---|---|---|
| Met | Thr | Thr | Phe | Leu | Leu | Arg | Asp | Ile | Arg | Ile | Phe | Thr | Gly | Glu | Gly |
| 1 | | | | 5 | | | | | 10 | | | | | 15 | |
| Thr | Ile | Asp | Lys | Gly | Tyr | Ile | His | Val | Gln | Asn | Gly | Lys | Ile | Lys | Ala |
| | | | 20 | | | | | 25 | | | | | 30 | | |
| Ile | Gly | Gln | Ile | Ser | Glu | Ala | Pro | Leu | Asp | Ser | Val | Lys | Thr | Tyr | Ser |
| | | | | 35 | | | | | 40 | | | | | 45 | |
| Lys | Pro | Gly | His | Thr | Ile | Leu | Pro | Gly | Leu | Ile | Asp | Cys | His | Ile | His |
| | 50 | | | | | 55 | | | | | 60 | | | | |
| Ala | Asp | Arg | Ala | Asp | Pro | Glu | Ala | Leu | Pro | Gln | Ala | Leu | Arg | Phe | Gly |
| 65 | | | | | 70 | | | | | 75 | | | | | 80 |
| Val | Thr | Thr | Val | Cys | Glu | Met | His | Asn | Glu | Leu | Glu | Asn | Val | Gln | Lys |
| | | | | 85 | | | | | 90 | | | | | 95 | |
| Leu | Lys | Lys | Gln | Thr | Met | Glu | Pro | Asp | Thr | Ala | Ser | Tyr | Lys | Thr | Ala |
| | | | 100 | | | | | 105 | | | | | 110 | | |
| Gly | Gln | Ala | Ala | Thr | Ile | Glu | Asn | Gly | Trp | Pro | Ile | Pro | Val | Ile | Thr |
| | | | | 115 | | | | | 120 | | | | | 125 | |
| Ala | His | Asp | Lys | Thr | Pro | Glu | Thr | Ala | Ala | Ala | Ile | Ala | Lys | Trp | Pro |
| | 130 | | | | | 135 | | | | | 140 | | | | |
| Lys | Leu | Thr | Asp | Arg | Asp | Ser | Val | Val | Glu | Phe | Leu | Glu | Trp | Thr | Gly |
| 145 | | | | | 150 | | | | | 155 | | | | | 160 |
| Arg | Glu | Met | Gln | Pro | Asn | Tyr | Ile | Lys | Leu | Met | His | Glu | Ser | Gly | Thr |
| | | | | 165 | | | | | 170 | | | | | 175 | |
| Ile | Met | Gly | Arg | Asn | Phe | Ser | Tyr | Pro | Ser | Phe | Glu | Leu | Gln | Ser | Thr |
| | | | 180 | | | | | 185 | | | | | 190 | | |
| Ile | Ile | Ala | Glu | Ala | Lys | Lys | Arg | Gly | Tyr | Leu | Thr | Val | Ala | His | Ala |
| | | | | 195 | | | | | 200 | | | | | 205 | |
| Leu | Ser | Met | Arg | Asp | Thr | Leu | Glu | Val | Leu | Asn | Ala | Gly | Val | Asp | Gly |
| | 210 | | | | | 215 | | | | | 220 | | | | |
| Leu | Thr | His | Thr | Phe | Phe | Asp | Gln | Pro | Pro | Thr | Gln | Glu | Leu | Val | Asp |
| 225 | | | | | 230 | | | | | 235 | | | | | 240 |
| Ala | Tyr | Lys | Lys | Asn | Asn | Ala | Trp | Val | Asn | Pro | Thr | Leu | Val | Ala | Ile |
| | | | | 245 | | | | | 250 | | | | | 255 | |
| Gly | Ser | Leu | Thr | Thr | Glu | Gly | Lys | Glu | Leu | Gln | His | Gln | Phe | Ala | His |
| | | | 260 | | | | | 265 | | | | | 270 | | |
| Asp | Pro | Arg | Val | Lys | Gly | Leu | Ile | Lys | Glu | Asp | Arg | Val | Gly | Asn | Met |
| | | | | 275 | | | | | 280 | | | | | 285 | |
| Cys | Lys | Cys | Met | Gly | Phe | Ala | Ala | Glu | Gly | Gly | Lys | Val | Glu | Tyr | Ala |
| | 290 | | | | | 295 | | | | | 300 | | | | |
| Tyr | Gln | Gly | Val | Lys | Gly | Leu | Arg | Glu | Ala | Gly | Ile | Asp | Ile | Leu | Cys |
| 305 | | | | | 310 | | | | | 315 | | | | | 320 |
| Gly | Ser | Asp | Ser | Ala | Gly | Pro | Ala | Val | Gly | Thr | Ala | Phe | Gly | Leu | Ser |
| | | | | 325 | | | | | 330 | | | | | 335 | |
| Met | His | His | Glu | Leu | Tyr | Leu | Leu | Val | Asn | Lys | Val | Gly | Met | Thr | Pro |
| | | | 340 | | | | | 345 | | | | | 350 | | |
| Ile | Glu | Ala | Leu | Arg | Ser | Ala | Thr | Ser | Leu | Thr | Ala | Lys | Arg | Phe | Gln |
| | | | | 355 | | | | | 360 | | | | | 365 | |

Phe Arg Asp Arg Gly Arg Leu Ala Glu Gly Leu Asn Ala Asp Leu Leu
       370                 375                 380

Leu Val Glu Gly Asn Pro Leu Glu Asp Ile Asp Ala Thr Leu Asn Ile
385                 390                 395                 400

Arg Gly Val Trp Arg Asp Gly Asn Leu Cys Ser Thr Tyr Val Glu Lys
                405                 410                 415

Leu Gly Ala Gly Val Glu Pro Leu Leu Ser
            420                 425

<210> SEQ ID NO 23
<211> LENGTH: 714
<212> TYPE: DNA
<213> ORGANISM: Alternaria brassicicola

<400> SEQUENCE: 23
atgggctccg gatcgtctga tagcaccgag ttcttccaga gctgggactt gtggcagaag    60 atgactttg tactggcttg cggaattgtc gtcaccatct tcgttggcct gctcaaactc    120
tggtatgaca gaacaaggt tcgcaagtac agcaaggtcg acaagggcaa acgggcgtcg    180
acgcccgaaa tgctcgaggc gcagccagta acccaggttc aagaagacac caaagatgag    240
attccctttg gtatccgcgc aatccaaagc ggcatcgagg ttgatggcgt ctggatctcg    300
cgtaccaaca ctcctgttgg cagtagccgt gcttccatca tgagcgaaca gcttccccgc    360
aacttcaaca actcccagct cgagctgccc cagccagtcg cccagggttc aagccgcaac    420
agctcgcgcg ctcctagctc gtttgaccgt gccgtctccg ccgagcctct tccaagctac    480
gactcccgcg catcttcgcc tggccgcggg cacaaccatg agggccctcg ctgcagcaac    540
tgcaaccacc acgtctcccg caacgctgcg gccctcagcg ccctcgagtc tcccaactct    600
acccgcaact ctgctgctcc ttcgcctcct cttcaagcca aacacagcca gtctgcaagc    660
tcctcgagcc gacgcacgag tgacgagtcc gactacatgg ccattgggca agac          714

<210> SEQ ID NO 24
<211> LENGTH: 238
<212> TYPE: PRT
<213> ORGANISM: Alternaria brassicicola

<400> SEQUENCE: 24

Met Gly Ser Gly Ser Ser Asp Ser Thr Glu Phe Phe Gln Ser Trp Asp
1               5                   10                  15

Leu Trp Gln Lys Met Thr Phe Val Leu Ala Cys Gly Ile Val Val Thr
            20                  25                  30

Ile Phe Val Gly Leu Leu Lys Leu Trp Tyr Asp Lys Asn Lys Val Arg
        35                  40                  45

Lys Tyr Ser Lys Val Asp Lys Gly Lys Arg Ala Ser Thr Pro Glu Met
    50                  55                  60

Leu Glu Ala Gln Pro Val Thr Gln Val Gln Glu Asp Thr Lys Asp Glu
65                  70                  75                  80

Ile Pro Phe Gly Ile Arg Ala Ile Gln Ser Gly Ile Glu Val Asp Gly
                85                  90                  95

Val Trp Ile Ser Arg Thr Asn Thr Pro Val Gly Ser Ser Arg Ala Ser
            100                 105                 110

Ile Met Ser Glu Gln Leu Pro Arg Asn Phe Asn Ser Gln Leu Glu
        115                 120                 125

Leu Pro Gln Pro Val Ala Gln Gly Ser Ser Arg Asn Ser Ser Arg Ala
    130                 135                 140

```
Pro Ser Ser Phe Asp Arg Ala Val Ser Ala Glu Pro Leu Pro Ser Tyr
145                 150                 155                 160

Asp Ser Arg Ala Ser Pro Gly Arg Gly His Asn His Glu Gly Pro
            165                 170                 175

Arg Cys Ser Asn Cys Asn His His Val Ser Arg Asn Ala Ala Ala Leu
            180                 185                 190

Ser Ala Leu Glu Ser Pro Asn Ser Thr Arg Asn Ser Ala Ala Pro Ser
        195                 200                 205

Pro Pro Leu Gln Ala Lys His Ser Gln Ser Ala Ser Ser Ser Ser Arg
        210                 215                 220

Arg Thr Ser Asp Glu Ser Asp Tyr Met Ala Ile Gly Gln Asp
225                 230                 235

<210> SEQ ID NO 25
<211> LENGTH: 451
<212> TYPE: DNA
<213> ORGANISM: Alternaria brassicicola

<400> SEQUENCE: 25
atgtgcgtgg atgtgtgggt atgggaatgg tcggtggccg atggtgtcgt tcgcgtggtg    60
aagctccaac gcggcggcca tggacgcccg gaactagccg tcgcctcgac tggccggacc   120
ctgggtatga cgcgctggcc ccatgcccat cagatgcctc aagaggagcc cggagacggc   180
agcacccacg aaaccgaatc ccaaacgcga atgccgcccc acaaccagag cagccagagc   240
aagcgcaagc acaatcaaca cagccgtcac aaagaggtgg cggacgaggt ggcaggggac   300
gagggcaagg gcaagggcga gggcgagggc gagggcgagg ggggcaagca gacagtgaaa   360
ggccttcgca accaaatgct gccgctctcg aatttgtgcc ttcatctgta caagaagcag   420
cgcatcgagg aggaagacgt ggacgtgggg g                                   451

<210> SEQ ID NO 26
<211> LENGTH: 150
<212> TYPE: PRT
<213> ORGANISM: Alternaria brassicicola

<400> SEQUENCE: 26

Met Cys Val Asp Val Trp Val Trp Glu Trp Ser Val Ala Asp Gly Val
1               5                   10                  15

Val Arg Val Val Lys Leu Gln Arg Gly Gly His Gly Arg Pro Glu Leu
            20                  25                  30

Ala Val Ala Ser Thr Gly Arg Thr Leu Gly Met Thr Arg Trp Pro His
        35                  40                  45

Ala His Gln Met Pro Gln Glu Glu Pro Gly Asp Gly Ser Thr His Glu
    50                  55                  60

Thr Glu Ser Gln Thr Arg Met Pro Pro His Asn Gln Ser Ser Gln Ser
65                  70                  75                  80

Lys Arg Lys His Asn Gln His Ser Arg His Lys Glu Val Ala Asp Glu
                85                  90                  95

Val Ala Gly Asp Glu Gly Lys Gly Lys Gly Glu Gly Glu Gly Glu Gly
            100                 105                 110

Glu Gly Gly Lys Gln Thr Val Lys Gly Leu Arg Asn Gln Met Leu Pro
        115                 120                 125

Leu Ser Asn Leu Cys Leu His Leu Tyr Lys Lys Gln Arg Ile Glu Glu
    130                 135                 140

Glu Asp Val Asp Val Gly
145                 150
```

<210> SEQ ID NO 27
<211> LENGTH: 1023
<212> TYPE: DNA
<213> ORGANISM: Alternaria brassicicola

<400> SEQUENCE: 27

```
atggccgcca ccactacaaa tcatggcact aacacgcctc ctagcacaat gacatccgca        60
cccacaatac agcccaagtt cctgccaaac aggcatgacc taggcatcgt cgcagtcggc       120
ttcagcggcg gccagcccaa agccggcgtc gacgccgcgc ccatggccct catcgaaaat       180
ggcctcatca gcaattaga agaagatcta gaattctccg tcacctacga cggccaagtg       240
cacaactaca ccgagctcca gccctccgac gacccagact accggggcat gaagcgcccc       300
aagttcgcct cggccgtcac aaagcaagtc tctgaccaag tctacagcca cgccaagtcg       360
ggcaagctgg tcctcaccct cggcggcgac cactccatcg ccattggcac tgtttccggc       420
accgcaaagg ctattcgcga gcggctgggc aaggacatgg ccgtcatctg gtcgatgcg        480
catgctgata ttaatacgcc cgagacgagc gattcgggca acatccacgg catgcccgtg       540
tctttcttga cggggctggc gaccgaggag cgggaagatg tgtttggctg gattaaagag       600
gatcagagga ttagcacgaa gaagctagta tacattggat tgagggacat tgatagtgga       660
gagaagaaga ttctgaggca gcacgggatc aaggcgttta gcatgcatga tattgacagg       720
cacggtattg gcaaaatcat ggacatggcg ctgggttgga tcggaagcga cacgcccatc       780
catctctcct tcgacgtcga cgctctcgac cccatgtggg cgcctagcac cggtacgcct       840
gttcgcggcg gcctgacgct gcgcgagggc gacttcatcg ccgagtgcgt tgccgagact       900
ggtcagctca ttgccttgga tctggtcgag gtgaatccta gccttgatgc cgagggtgct       960
ggcgacacgg tccgcgctgg tgtttcgatt gtgaggtgcg cgcttggtga cacgcttttg      1020
tag                                                                   1023
```

<210> SEQ ID NO 28
<211> LENGTH: 340
<212> TYPE: PRT
<213> ORGANISM: Alternaria brassicicola

<400> SEQUENCE: 28

Met Ala Ala Thr Thr Thr Asn His Gly Thr Asn Thr Pro Ser Thr
1               5                   10                  15

Met Thr Ser Ala Pro Thr Ile Gln Pro Lys Phe Leu Pro Asn Arg His
            20                  25                  30

Asp Leu Gly Ile Val Ala Val Gly Phe Ser Gly Gly Gln Pro Lys Ala
        35                  40                  45

Gly Val Asp Ala Ala Pro Met Ala Leu Ile Glu Asn Gly Leu Ile Lys
    50                  55                  60

Gln Leu Glu Glu Asp Leu Glu Phe Ser Val Thr Tyr Asp Gly Gln Val
65                  70                  75                  80

His Asn Tyr Thr Glu Leu Gln Pro Ser Asp Asp Pro Asp Tyr Arg Gly
                85                  90                  95

Met Lys Arg Pro Lys Phe Ala Ser Ala Val Thr Lys Gln Val Ser Asp
            100                 105                 110

Gln Val Tyr Glu His Ala Lys Ser Gly Lys Leu Val Leu Thr Leu Gly
        115                 120                 125

Gly Asp His Ser Ile Ala Ile Gly Thr Val Ser Gly Thr Ala Lys Ala
    130                 135                 140

Ile Arg Glu Arg Leu Gly Lys Asp Met Ala Val Ile Trp Val Asp Ala

```
                145                 150                 155                 160
His Ala Asp Ile Asn Thr Pro Glu Thr Ser Asp Ser Gly Asn Ile His
                165                 170                 175

Gly Met Pro Val Ser Phe Leu Thr Gly Leu Ala Thr Glu Glu Arg Glu
            180                 185                 190

Asp Val Phe Gly Trp Ile Lys Glu Asp Gln Arg Ile Ser Thr Lys Lys
        195                 200                 205

Leu Val Tyr Ile Gly Leu Arg Asp Ile Asp Ser Gly Glu Lys Lys Ile
    210                 215                 220

Leu Arg Gln His Gly Ile Lys Ala Phe Ser Met His Asp Ile Asp Arg
225                 230                 235                 240

His Gly Ile Gly Lys Ile Met Asp Met Ala Leu Gly Trp Ile Gly Ser
                245                 250                 255

Asp Thr Pro Ile His Leu Ser Phe Asp Val Asp Ala Leu Asp Pro Met
            260                 265                 270

Trp Ala Pro Ser Thr Gly Thr Pro Val Arg Gly Gly Leu Thr Leu Arg
        275                 280                 285

Glu Gly Asp Phe Ile Ala Glu Cys Val Ala Glu Thr Gly Gln Leu Ile
    290                 295                 300

Ala Leu Asp Leu Val Glu Val Asn Pro Ser Leu Asp Ala Glu Gly Ala
305                 310                 315                 320

Gly Asp Thr Val Arg Ala Gly Val Ser Ile Val Arg Cys Ala Leu Gly
                325                 330                 335

Asp Thr Leu Leu
        340

<210> SEQ ID NO 29
<211> LENGTH: 1371
<212> TYPE: DNA
<213> ORGANISM: Alternaria brassicicola

<400> SEQUENCE: 29
atgtacagga cactcgctct cgcttccctc tcgctcttcg gagccgcccg cgctcagcag      60
gttggcaaag agacaacgga gacacacccc aagatgacat ggcagacttg cactggcacc     120
ggtggaaaga gctgcaccaa taagcagggt ccatcgtgc tcgactccaa ctggcgatgg      180
tcccacgtca ccagcggata caccaactgc ttcgacggca actcttggaa cacgaccgct     240
tgccctgatg gcagcacttg caccaagaac tgcgccatcg acggtgccga ttactctggc     300
acttacggca tcaccaccag cagcaatgct ctgactctca gttcgtcac caagggctct      360 tactctgcca acattggttc acgtacctac ctcatggaga gtgacaccaa gtaccaaatg     420
ttcaatctca tcggcaagga gttcaccttc gatgtcgatg tctccaagct gccttgcggt     480
ctgaacggtg ctctctactt tgttgaaatg gccgccgacg gtggcatgaa caagggcaac     540
aacaaggccg gtgccaagta cggaaccgga tactgcgact cccagtgccc tcacgacatc     600
aagtttatca acggtgtagc caacgtagag ggctggaacc cgtccgacaa tgaccccaac     660
gccggcgctg gtaagattgg tgcttgctgc cccgaaatgg atatctggga ggccaactcc     720
atctctactg cctacactcc ccatccctgc aagggcactg tcttcagga gtgcactgac      780 gaggtcagct gcggtgatgg cgacaaccgt tacggcggta tctgcgacaa ggacggttgc     840
gatttcaaca gctaccgcat gggtgtccgt gacttctacg gtccaggcat gaccctcgat     900
accaccaaga gatgactgt cgtcactcag ttcctcggtt ccggttccag cctctcggag      960
atcaagcgct tctacatcca gggaggaacc gtcttcaaga actccgactc cgccgtcgaa    1020
```

-continued

```
ggcgtcactg gtaactccat cactgaggaa ttctgtgacc agcaaaagac cgtcttcggt      1080
gacacatctt ctttcaagac tcttggtgga cttgatgaga tgggtgcctc gcttgctcgc      1140
ggtcacgtcc ttgtcatgtc cctttgggac gaccatgcgg tcaacatgct ttggctcgac      1200
tccacctacc ctaccgacgc tgacccagag aagcctggta tcgcccgtgg tacctgcgct      1260
accgactctg gcaagcccga ggacgtcgag gccaactcgc ccgacgcgac tgtcatcttc      1320
tccaacatca agttcggtcc catcggctcc acctttccg cacccgcata a                1371
```

<210> SEQ ID NO 30
<211> LENGTH: 456
<212> TYPE: PRT
<213> ORGANISM: Alternaria brassicicola

<400> SEQUENCE: 30

```
Met Tyr Arg Thr Leu Ala Leu Ala Ser Leu Ser Phe Gly Ala Ala
1               5                   10                  15

Arg Ala Gln Gln Val Gly Lys Glu Thr Thr Glu Thr His Pro Lys Met
            20                  25                  30

Thr Trp Gln Thr Cys Thr Gly Thr Gly Gly Lys Ser Cys Thr Asn Lys
        35                  40                  45

Gln Gly Ser Ile Val Leu Asp Ser Asn Trp Arg Trp Ser His Val Thr
    50                  55                  60

Ser Gly Tyr Thr Asn Cys Phe Asp Gly Asn Ser Trp Asn Thr Thr Ala
65                  70                  75                  80

Cys Pro Asp Gly Ser Thr Cys Thr Lys Asn Cys Ala Ile Asp Gly Ala
                85                  90                  95

Asp Tyr Ser Gly Thr Tyr Gly Ile Thr Thr Ser Ser Asn Ala Leu Thr
            100                 105                 110

Leu Lys Phe Val Thr Lys Gly Ser Tyr Ser Ala Asn Ile Gly Ser Arg
        115                 120                 125

Thr Tyr Leu Met Glu Ser Asp Thr Lys Tyr Gln Met Phe Asn Leu Ile
    130                 135                 140

Gly Lys Glu Phe Thr Phe Asp Val Asp Val Ser Lys Leu Pro Cys Gly
145                 150                 155                 160

Leu Asn Gly Ala Leu Tyr Phe Val Glu Met Ala Ala Asp Gly Gly Met
                165                 170                 175

Asn Lys Gly Asn Asn Lys Ala Gly Ala Lys Tyr Gly Thr Gly Tyr Cys
            180                 185                 190

Asp Ser Gln Cys Pro His Asp Ile Lys Phe Ile Asn Gly Val Ala Asn
        195                 200                 205

Val Glu Gly Trp Asn Pro Ser Asp Asn Asp Pro Asn Ala Gly Ala Gly
    210                 215                 220

Lys Ile Gly Ala Cys Cys Pro Glu Met Asp Ile Trp Glu Ala Asn Ser
225                 230                 235                 240

Ile Ser Thr Ala Tyr Thr Pro His Pro Cys Lys Gly Thr Gly Leu Gln
                245                 250                 255

Glu Cys Thr Asp Glu Val Ser Cys Gly Asp Gly Asp Asn Arg Tyr Gly
            260                 265                 270

Gly Ile Cys Asp Lys Asp Gly Cys Asp Phe Asn Ser Tyr Arg Met Gly
        275                 280                 285

Val Arg Asp Phe Tyr Gly Pro Gly Met Thr Leu Asp Thr Thr Lys Lys
    290                 295                 300

Met Thr Val Val Thr Gln Phe Leu Gly Ser Gly Ser Ser Leu Ser Glu
305                 310                 315                 320
```

```
Ile Lys Arg Phe Tyr Ile Gln Gly Gly Thr Val Phe Lys Asn Ser Asp
                325                 330                 335

Ser Ala Val Glu Gly Val Thr Gly Asn Ser Ile Thr Glu Glu Phe Cys
            340                 345                 350

Asp Gln Gln Lys Thr Val Phe Gly Asp Thr Ser Ser Phe Lys Thr Leu
        355                 360                 365

Gly Gly Leu Asp Glu Met Gly Ala Ser Leu Ala Arg Gly His Val Leu
    370                 375                 380

Val Met Ser Leu Trp Asp Asp His Ala Val Asn Met Leu Trp Leu Asp
385                 390                 395                 400

Ser Thr Tyr Pro Thr Asp Ala Asp Pro Glu Lys Pro Gly Ile Ala Arg
                405                 410                 415

Gly Thr Cys Ala Thr Asp Ser Gly Lys Pro Glu Asp Val Glu Ala Asn
            420                 425                 430

Ser Pro Asp Ala Thr Val Ile Phe Ser Asn Ile Lys Phe Gly Pro Ile
        435                 440                 445

Gly Ser Thr Phe Ser Ala Pro Ala
    450                 455

<210> SEQ ID NO 31
<211> LENGTH: 1203
<212> TYPE: DNA
<213> ORGANISM: Alternaria brassicicola

<400> SEQUENCE: 31
atgctctcca acctccttct cactgctgcg cttgcagtag gcgtggctca ggccctgcct      60
caagcgacaa gtgtctcgag gactacatct accgcccgtg caacgaccac tgccccatca     120
gcaactggaa accccttcgc tggcaaggat ttctatgcca acccatacta ctcgtccgag     180
gtttacaccc tagccatgcc ctcgcttgct gcgtctctga agcccgctgc ttctgccgtg     240
gccaaagtcg gttcattcgt atggatggac acaatggcca aggtgcccac catggacacg     300
tatctggcag acatcaaagc caagaatgcc gcaggtgcaa agctgatggg tacctttgtc     360
gtctacgacc tgcccgaccg cgactgcgct gcccttgcct ccaacggcga gctcaagatc     420
gacgacggtg gtgtagagaa gtacaagacc cagtacatcg acaagattgc cgctattatt     480
aaggcgtacc tgacattaa gatcaacctc gccattgagc ccgactcgtt ggccaacatg     540
gtcaccaaca tgggcgtaca aaagtgctcg cgcgccgctc cctactacaa agagcttacc     600
gcgtacgctc tcaagacgct caatttcccc aacgtcgaca tgtacctcga cggtggccac     660
gctggctggc ttggctggga cgccaacatt ggtccagccg caaaactcta cgccgaagtc     720
tacaaggccg ctggctcgcc ccgcgccgtc cgtggtatcg tcaccaacgt cagcaactac     780
aacgccttcc gcatcggcac ttgccctgcc atcacccaag gaaacaagaa ctgcgacgaa     840
gagcgcttca tcgacgcttt cgctcctctt ctccgcgccg aaggcttccc tgcccacttc     900
atcgtcgaca ctggacgtag cggtaagcag cctactgacc agcaggcctg gggagactgg     960
tgcaacgttt cgggtgctgg ctttggtatt cgtcctacta ccaacaccaa caatgcgctt    1020
gtcgatgctt ttgtctgggt caagcctggt ggcgagtctg atggtacttc tgaccaatct    1080
gctgctcgct acgacggctt ctgcggcaag gcctccgctt tgaagcctgc gcccgaggct    1140
ggtacttggt ccaggcata ctttgagatg ttgttaaaga acgccaaccc cgctcttgca    1200
taa                                                                  1203

<210> SEQ ID NO 32
<211> LENGTH: 400
```

```
<212> TYPE: PRT
<213> ORGANISM: Alternaria brassicicola

<400> SEQUENCE: 32

Met Leu Ser Asn Leu Leu Thr Ala Ala Leu Ala Val Gly Val Ala
1               5                   10                  15

Gln Ala Leu Pro Gln Ala Thr Ser Val Ser Arg Thr Ser Thr Ala
                20                  25                  30

Arg Ala Thr Thr Thr Ala Pro Ser Ala Thr Gly Asn Pro Phe Ala Gly
            35                  40                  45

Lys Asp Phe Tyr Ala Asn Pro Tyr Tyr Ser Ser Glu Val Tyr Thr Leu
    50                  55                  60

Ala Met Pro Ser Leu Ala Ala Ser Leu Lys Pro Ala Ala Ser Ala Val
65                  70                  75                  80

Ala Lys Val Gly Ser Phe Val Trp Met Asp Thr Met Ala Lys Val Pro
                85                  90                  95

Thr Met Asp Thr Tyr Leu Ala Asp Ile Lys Ala Lys Asn Ala Ala Gly
                100                 105                 110

Ala Lys Leu Met Gly Thr Phe Val Val Tyr Asp Leu Pro Asp Arg Asp
            115                 120                 125

Cys Ala Ala Leu Ala Ser Asn Gly Glu Leu Lys Ile Asp Asp Gly Gly
130                 135                 140

Val Glu Lys Tyr Lys Thr Gln Tyr Ile Asp Lys Ile Ala Ala Ile Ile
145                 150                 155                 160

Lys Ala Tyr Pro Asp Ile Lys Ile Asn Leu Ala Ile Glu Pro Asp Ser
                165                 170                 175

Leu Ala Asn Met Val Thr Asn Met Gly Val Gln Lys Cys Ser Arg Ala
            180                 185                 190

Ala Pro Tyr Tyr Lys Glu Leu Thr Ala Tyr Ala Leu Lys Thr Leu Asn
        195                 200                 205

Phe Pro Asn Val Asp Met Tyr Leu Asp Gly Gly His Ala Gly Trp Leu
210                 215                 220

Gly Trp Asp Ala Asn Ile Gly Pro Ala Ala Lys Leu Tyr Ala Glu Val
225                 230                 235                 240

Tyr Lys Ala Ala Gly Ser Pro Arg Ala Val Arg Gly Ile Val Thr Asn
                245                 250                 255

Val Ser Asn Tyr Asn Ala Phe Arg Ile Gly Thr Cys Pro Ala Ile Thr
            260                 265                 270

Gln Gly Asn Lys Asn Cys Asp Glu Glu Arg Phe Ile Asp Ala Phe Ala
        275                 280                 285

Pro Leu Leu Arg Ala Glu Gly Phe Pro Ala His Phe Ile Val Asp Thr
290                 295                 300

Gly Arg Ser Gly Lys Gln Pro Thr Asp Gln Gln Ala Trp Gly Asp Trp
305                 310                 315                 320

Cys Asn Val Ser Gly Ala Gly Phe Gly Ile Arg Pro Thr Thr Asn Thr
                325                 330                 335

Asn Asn Ala Leu Val Asp Ala Phe Val Trp Val Lys Pro Gly Gly Glu
            340                 345                 350

Ser Asp Gly Thr Ser Asp Gln Ser Ala Ala Arg Tyr Asp Gly Phe Cys
        355                 360                 365

Gly Lys Ala Ser Ala Leu Lys Pro Ala Pro Glu Ala Gly Thr Trp Phe
        370                 375                 380

Gln Ala Tyr Phe Glu Met Leu Leu Lys Asn Ala Asn Pro Ala Leu Ala
385                 390                 395                 400
```

<210> SEQ ID NO 33
<211> LENGTH: 2667
<212> TYPE: DNA
<213> ORGANISM: Alternaria brassicicola

<400> SEQUENCE: 33

| | | | | | |
|---|---|---|---|---|---|
| atgaagacaa | cttctttcgt | tcaagcggct | tcgctgctat | ccactctttt | cgctcctctc | 60 |
| gctcttgcgc | aggagaagtt | tacccacgaa | ggtaccggga | ttgagttctg | gcgccaggta | 120 |
| gtcagtgact | cccagactgc | aggaggcttc | gagtggggct | gggtattgcc | agcagagccc | 180 |
| actggagcca | acgacgaata | catcggttac | attaaaggtt | cgctggaagc | gaacagacag | 240 |
| ggatggtccg | gtgtcagcca | cgctggtggc | atggctaact | ctcttttgct | cgttgcatgg | 300 |
| ccggaaactg | atgctgtcaa | gaccaagttt | gtctgggcag | gtggctatat | tgctcctgaa | 360 |
| gactacactg | gcaacgcgac | tttgagccag | atctttcact | cagtcaccga | cacacacttc | 420 |
| gagatcgtgt | accgatgcga | gcactgctgg | gtctggaatc | agggtggtgc | tgaaggctcc | 480 |
| caactcccca | ccagcgaagt | caatgttatc | ggctgggccc | agcataacaa | aatctacgac | 540 |
| ggcacttggg | tcttccacaa | caagggacag | tccctgtttg | gtgctcctac | ggtggatgca | 600 |
| aggaacgcga | agtactccga | ctatgtcaaa | ctggcaggag | gccagccatc | tggtgcacct | 660 |
| acaccaacct | tgtccggcca | gccgtcagcc | acacccactc | ccactgcacc | ggtaaagtgc | 720 |
| accggatccc | cagccccttc | aggttccttt | gactacatcg | tcattggtgg | tggtgctgga | 780 |
| ggtatcccca | tggcggacag | gctttccgag | tctggcaaga | gcgttctcat | gctcgagaag | 840 |
| ggcccgccgt | ccctcgctcg | ttttggcgga | aagatgggcc | ctgaatgggc | taccaccaac | 900 |
| aatttgactc | ggttcgacat | ccctggtctc | tgcaaccaga | tctgggttga | ctctgcaggt | 960 |
| gttgcttgca | ccgatatcga | ccaaatggct | ggctgtgtcc | ttggtggagg | tactgccgtc | 1020 |
| aatgctgcgc | tttggtggaa | gccggtagac | atcgatttcg | actaccaatt | ccccgctggc | 1080 |
| tggaaatcag | cggacgtgaa | gggcgcgatc | gaccgtgtgt | tcaagcgcat | ccctggtact | 1140 |
| gataccccctt | ccgtggacgg | caagcgttac | aagcaggaag | gctttgatgt | cctatccggt | 1200 |
| gcgcttggtg | cggatggctg | gaagagcgtc | gtcgcgaacg | accaacagaa | ccagaagaat | 1260 |
| cgcacatact | ctcactctcc | gttcatgtat | gacaacggtc | aaaggcaagg | acctctcggt | 1320 |
| acttacatgg | tttctgcgct | ggaaaggaag | aacttcaagc | tctggacgaa | caccatggct | 1380 |
| cgacgcatcg | tccgcactgg | cggaacggct | accggtgttg | agcttgagag | cggtgtcggt | 1440 |
| ggtactggtt | actgcggtac | cgtcaacctc | aaccctggag | gccgtgttat | tgtctccggt | 1500 |
| ggagctttcg | gatcgtcaaa | ggttctcttc | cgcagcggca | ttggaccaaa | ggatcagctg | 1560 |
| aacatcgtga | agaacagcgc | tctcgatggc | tcgacaatga | ttggagagtc | tgactggatt | 1620 |
| aacctccccg | tcggccaaaa | cttgaacgac | cacgtcaaca | ccgatcttgt | tatcaggcac | 1680 |
| cccaacatct | cttcctacaa | cttttacgag | gcgtgggatg | cccccatcga | ggctgacaaa | 1740 |
| gacctgtacc | ttggcaagcg | ttctggtatc | cttgcccagt | ctgcacccaa | catcggcccc | 1800 |
| cttgcttggg | aagtgattac | tggaagtgac | ggcattgacc | gatcgatcca | gtggactgct | 1860 |
| cgtgttgaag | gccccggcgc | caacgatact | caccacctca | ccatcagcca | gtacctcggt | 1920 |
| cacggctcta | cttcgcgtgg | tgcgcttttcc | atcaacggtg | ctctcaacgt | gtatgtcagc | 1980 |
| aaatcaccct | acctacagaa | cgaggccgac | actggtgtgg | ttgtcgcagg | tatcaagagc | 2040 |
| atgatgaagg | ccatccagaa | gaacccagcc | atcgagttcc | aagtaccgcc | tgccaatatg | 2100 |
| acagttgagg | catacgttgc | cagcctcccc | aagacccccag | ctgcccgtcg | cgccaaccac | 2160 |

```
tggatcggta ccgccaagat cggaaccgac agcggtctca cgggtggaac ctctgtggtg    2220
gacctgaaca ctcaggtgta tggaacgcag aacatccacg tagtcgacgc ttcgctcttc    2280
cctggtcaaa ttttcaccaa ccctacatcc tacatcatcg tactcgcaga acatgccgct    2340
gctaagattc tcgcacttag tgcaagcagt ggaggtggta agccttcgtc gtccgctttg    2400
tcgtccgcag tctccgctaa acccactacc tcgaaggcac caactgagtc gtcaaccgta    2460
tccgtggagc gtccatcgac accagccaag tcttcggcta agtcgactac tatcaagaca    2520
tctgcagcac cagcacctac tcctaccagg gtgtcgaagg cctgggaacg atgcggtggt    2580
aaaggctaca ctggcccaac agcttgtgtc agtgggcaca gtgcgcagt gagcaatgag     2640 tactactctc agtgcatccc taactaa                                        2667
```

<210> SEQ ID NO 34
<211> LENGTH: 888
<212> TYPE: PRT
<213> ORGANISM: Alternaria brassicicola

<400> SEQUENCE: 34

```
Met Lys Thr Thr Ser Phe Val Gln Ala Ala Ser Leu Leu Ser Thr Leu
1               5                   10                  15

Phe Ala Pro Leu Ala Leu Ala Gln Glu Lys Phe Thr His Glu Gly Thr
            20                  25                  30

Gly Ile Glu Phe Trp Arg Gln Val Ser Asp Ser Gln Thr Ala Gly
        35                  40                  45

Gly Phe Glu Trp Gly Trp Val Leu Pro Ala Glu Pro Thr Gly Ala Asn
    50                  55                  60

Asp Glu Tyr Ile Gly Tyr Ile Lys Gly Ser Leu Glu Ala Asn Arg Gln
65                  70                  75                  80

Gly Trp Ser Gly Val Ser His Ala Gly Gly Met Ala Asn Ser Leu Leu
                85                  90                  95

Leu Val Ala Trp Pro Glu Thr Asp Ala Val Lys Thr Lys Phe Val Trp
            100                 105                 110

Ala Gly Gly Tyr Ile Ala Pro Glu Asp Tyr Thr Gly Asn Ala Thr Leu
        115                 120                 125

Ser Gln Ile Phe His Ser Val Thr Asp Thr His Phe Glu Ile Val Tyr
    130                 135                 140

Arg Cys Glu His Cys Trp Val Trp Asn Gln Gly Gly Ala Glu Gly Ser
145                 150                 155                 160

Gln Leu Pro Thr Ser Glu Val Asn Val Ile Gly Trp Ala Gln His Asn
                165                 170                 175

Lys Ile Tyr Asp Gly Thr Trp Val Phe His Asn Lys Gly Gln Ser Leu
            180                 185                 190

Phe Gly Ala Pro Thr Val Asp Ala Arg Asn Ala Lys Tyr Ser Asp Tyr
        195                 200                 205

Val Lys Leu Ala Gly Gly Gln Pro Ser Gly Ala Pro Thr Pro Thr Leu
    210                 215                 220

Ser Gly Gln Pro Ser Ala Thr Pro Thr Pro Thr Ala Pro Val Lys Cys
225                 230                 235                 240

Thr Gly Ser Pro Ala Pro Ser Gly Ser Phe Asp Tyr Ile Val Ile Gly
                245                 250                 255

Gly Gly Ala Gly Gly Ile Pro Met Ala Asp Arg Leu Ser Glu Ser Gly
            260                 265                 270

Lys Ser Val Leu Met Leu Glu Lys Gly Pro Pro Ser Leu Ala Arg Phe
        275                 280                 285
```

```
Gly Gly Lys Met Gly Pro Glu Trp Ala Thr Thr Asn Asn Leu Thr Arg
            290             295                 300
Phe Asp Ile Pro Gly Leu Cys Asn Gln Ile Trp Val Asp Ser Ala Gly
305                 310                 315                 320
Val Ala Cys Thr Asp Ile Asp Gln Met Ala Gly Cys Val Leu Gly Gly
                325                 330                 335
Gly Thr Ala Val Asn Ala Ala Leu Trp Trp Lys Pro Val Asp Ile Asp
                340                 345                 350
Phe Asp Tyr Gln Phe Pro Ala Gly Trp Lys Ser Ala Asp Val Lys Gly
            355                 360                 365
Ala Ile Asp Arg Val Phe Lys Arg Ile Pro Gly Thr Asp Thr Pro Ser
370                 375                 380
Val Asp Gly Lys Arg Tyr Lys Gln Glu Gly Phe Asp Val Leu Ser Gly
385                 390                 395                 400
Ala Leu Gly Ala Asp Gly Trp Lys Ser Val Ala Asn Asp Gln Gln
                405                 410                 415
Asn Gln Lys Asn Arg Thr Tyr Ser His Ser Pro Phe Met Tyr Asp Asn
                420                 425                 430
Gly Gln Arg Gln Gly Pro Leu Gly Thr Tyr Met Val Ser Ala Leu Glu
            435                 440                 445
Arg Lys Asn Phe Lys Leu Trp Thr Asn Thr Met Ala Arg Arg Ile Val
450                 455                 460
Arg Thr Gly Gly Thr Ala Thr Gly Val Glu Leu Glu Ser Gly Val Gly
465                 470                 475                 480
Gly Thr Gly Tyr Cys Gly Thr Val Asn Leu Asn Pro Gly Gly Arg Val
                485                 490                 495
Ile Val Ser Gly Gly Ala Phe Gly Ser Ser Lys Val Leu Phe Arg Ser
                500                 505                 510
Gly Ile Gly Pro Lys Asp Gln Leu Asn Ile Val Lys Asn Ser Ala Leu
            515                 520                 525
Asp Gly Ser Thr Met Ile Gly Glu Ser Asp Trp Ile Asn Leu Pro Val
            530                 535                 540
Gly Gln Asn Leu Asn Asp His Val Asn Thr Asp Leu Val Ile Arg His
545                 550                 555                 560
Pro Asn Ile Ser Ser Tyr Asn Phe Tyr Glu Ala Trp Asp Ala Pro Ile
                565                 570                 575
Glu Ala Asp Lys Asp Leu Tyr Leu Gly Lys Arg Ser Gly Ile Leu Ala
                580                 585                 590
Gln Ser Ala Pro Asn Ile Gly Pro Leu Ala Trp Glu Val Ile Thr Gly
            595                 600                 605
Ser Asp Gly Ile Asp Arg Ser Ile Gln Trp Thr Ala Arg Val Glu Gly
            610                 615                 620
Pro Gly Ala Asn Asp Thr His His Leu Thr Ile Ser Gln Tyr Leu Gly
625                 630                 635                 640
His Gly Ser Thr Ser Arg Gly Ala Leu Ser Ile Asn Gly Ala Leu Asn
                645                 650                 655
Val Tyr Val Ser Lys Ser Pro Tyr Leu Gln Asn Glu Ala Asp Thr Gly
                660                 665                 670
Val Val Val Ala Gly Ile Lys Ser Met Met Lys Ala Ile Gln Lys Asn
                675                 680                 685
Pro Ala Ile Glu Phe Gln Val Pro Ala Asn Met Thr Val Glu Ala
            690                 695                 700
Tyr Val Ala Ser Leu Pro Lys Thr Pro Ala Ala Arg Arg Ala Asn His
705                 710                 715                 720
```

```
Trp Ile Gly Thr Ala Lys Ile Gly Thr Asp Ser Gly Leu Thr Gly Gly
                725                 730                 735

Thr Ser Val Val Asp Leu Asn Thr Gln Val Tyr Gly Thr Gln Asn Ile
            740                 745                 750

His Val Val Asp Ala Ser Leu Phe Pro Gly Gln Ile Phe Thr Asn Pro
        755                 760                 765

Thr Ser Tyr Ile Ile Val Leu Ala Glu His Ala Ala Lys Ile Leu
    770                 775                 780

Ala Leu Ser Ala Ser Ser Gly Gly Gly Lys Pro Ser Ser Ser Ala Leu
785                 790                 795                 800

Ser Ser Ala Val Ser Ala Lys Pro Thr Thr Ser Lys Ala Pro Thr Glu
                805                 810                 815

Ser Ser Thr Val Ser Val Glu Arg Pro Ser Thr Pro Ala Lys Ser Ser
            820                 825                 830

Ala Lys Ser Thr Thr Ile Lys Thr Ser Ala Ala Pro Ala Pro Thr Pro
        835                 840                 845

Thr Arg Val Ser Lys Ala Trp Glu Arg Cys Gly Lys Gly Tyr Thr
    850                 855                 860

Gly Pro Thr Ala Cys Val Ser Gly His Lys Cys Ala Val Ser Asn Glu
865                 870                 875                 880

Tyr Tyr Ser Gln Cys Ile Pro Asn
                885

<210> SEQ ID NO 35
<211> LENGTH: 6
<212> TYPE: PRT
<213> ORGANISM: Artificial Sequence
<220> FEATURE:
<223> OTHER INFORMATION: Synthetically generated oligonucleotide

<400> SEQUENCE: 35

Leu Ser Ile Gly Lys Val
1               5

<210> SEQ ID NO 36
<211> LENGTH: 6
<212> TYPE: PRT
<213> ORGANISM: Artificial Sequence
<220> FEATURE:
<223> OTHER INFORMATION: Synthetically generated oligonucleotide

<400> SEQUENCE: 36

Gly Leu Ile Val Lys Ser
1               5

<210> SEQ ID NO 37
<211> LENGTH: 9
<212> TYPE: PRT
<213> ORGANISM: Artificial Sequence
<220> FEATURE:
<223> OTHER INFORMATION: Synthetically generated oligonucleotide

<400> SEQUENCE: 37

Ser Lys Gly Arg Ser Leu Ile Gly Lys
1               5

<210> SEQ ID NO 38
<211> LENGTH: 6
<212> TYPE: PRT
<213> ORGANISM: Artificial Sequence
<220> FEATURE:
<223> OTHER INFORMATION: Synthetically generated oligonucleotide
```

```
<400> SEQUENCE: 38

Ser Leu Ile Gly Lys Val
1               5
```